United States Patent
Padkær et al.

(10) Patent No.: US 8,222,376 B2
(45) Date of Patent: Jul. 17, 2012

(54) KIR-BINDING AGENTS AND METHODS OF USE THEREOF

(75) Inventors: Søren Berg Padkær, Værløse (DK); Peter Reumert Wagtmann, Rungsted Kyst (DK); Pieter Spee, Allerød (DK); Stefan Zahn, Ballerup (DK); Kristian Kjærgaard, Ballerup (DK)

(73) Assignees: Novo Nordisk A/S, Bagsvaerd (DK); Inmate Pharma S.A.S., Marseilles (FR)

( * ) Notice: Subject to any disclaimer, the term of this patent is extended or adjusted under 35 U.S.C. 154(b) by 832 days.

(21) Appl. No.: 11/813,402

(22) PCT Filed: Jan. 6, 2006

(86) PCT No.: PCT/EP2006/050073
§ 371 (c)(1),
(2), (4) Date: Jun. 6, 2008

(87) PCT Pub. No.: WO2006/072626
PCT Pub. Date: Jul. 13, 2006

(65) Prior Publication Data
US 2008/0305117 A1    Dec. 11, 2008

Related U.S. Application Data

(60) Provisional application No. 60/642,626, filed on Jan. 10, 2005.

(30) Foreign Application Priority Data

Jan. 6, 2005 (DK) .................. 2005 00021

(51) Int. Cl.
*C07K 16/00* (2006.01)
*C12P 21/08* (2006.01)
*A61K 39/395* (2006.01)

(52) U.S. Cl. ................ 530/388.73; 424/153.1
(58) Field of Classification Search .................. None
See application file for complete search history.

(56) References Cited

U.S. PATENT DOCUMENTS

| | | | |
|---|---|---|---|
| 4,816,567 A | | 3/1989 | Cabilly et al. |
| 5,539,094 A | | 7/1996 | Reed et al. |
| 5,583,034 A | | 12/1996 | Green et al. |
| 5,650,491 A | | 7/1997 | Reed et al. |
| 5,660,827 A | | 8/1997 | Thorpe et al. |
| 5,808,028 A | * | 9/1998 | Long et al. .............. 536/23.5 |
| 6,524,583 B1 | | 2/2003 | Thorpe et al. |
| 2005/0003172 A1 | * | 1/2005 | Wheeler et al. ........... 428/210 |

FOREIGN PATENT DOCUMENTS

| | | |
|---|---|---|
| WO | WO 9816551 | 4/1998 |
| WO | WO98/49292 | 11/1998 |
| WO | WO00/02583 | 1/2000 |
| WO | WO 00/26671 | 5/2000 |
| WO | WO00/50081 | 8/2000 |
| WO | WO2005/003168 | 1/2005 |
| WO | WO2005/003172 | 1/2005 |
| WO | WO 2005003172 A2 * | 1/2005 |
| WO | WO2005/009465 | 2/2005 |
| WO | WO2005/060375 | 7/2005 |
| WO | WO2006/003179 | 1/2006 |

OTHER PUBLICATIONS

Ponte et al., 1999, PNAS, vol. 96: 5674-5679.*
Moretta et al., 2004, Cur Opin. Immunol. vol. 16: 626-633.*
Fan et al., 2001. Nat. Immunol. vol. 2: 452-460.*
Boyington et al, Nature. vol. 405: 537-543.*
Shin, J.S. et al., Monoclonal Antibodies with Various Reactivity to p58 Killer Inhibitory Receptors, Hybridoma, vol. 18, No. 6, 1999, pp. 521-527.
Watzl, C. et al., Homogenous Expression of Killer Cell Immunoglobulin-like Receptors (KIR) on Polyclonal Natural Killer Cells Detected by a Monoclonal Antibody to KIR2D, Tissue Antigens, vol. 56, pp. 240-247, 2000.
Moretta, A. et al., A Novel Surface Antigen Expressed by a Subset of Human CD3CD16+Natural Killer Cells, Role in Cell Activation and Regulation of Cytolytic Function,Journal of Experimental Medicine, vol. 171, Mar. 1990, pp. 695-714.
Pascal, V. et al., Comparative Analysis of NK Cell Subset Distribution in Normal and Lymphoproliferative Disease of Granular Lymphocyte Conditions, Eur. J. Immunol., 2004, vol. 34, pp. 2930-2940.
Dorothee, G. et al., Functional and Molecular Characterization of a KIR3DL2/p140 Expressing Tumor-Specific Cytotoxic T Lymphocyte Clone Infiltrating a Human Lung Carcinoma, Oncogene, 2003, vol. 22, pp. 7192-7198.
Epling-Burnette, P.K. et al., Dysregulated NK Receptor Expression in Patients with Lymphoproliferative Disease of Granular Lymphocytes, Blood, 2004, vol. 103, No. 9, pp. 3431-3439.
Lee, N. et al., HLA-E is a Major Ligand for the Natural Killer Inhibitory Receptor CD94/NKG2A, Proc. Natl. Acad. Sci. USA, 1998, vol. 95, pp. 5199-5204.

(Continued)

*Primary Examiner* — Amy Juedes
(74) *Attorney, Agent, or Firm* — Hunton & Williams LLP

(57) ABSTRACT

The present invention relates to agents and methods that are capable of augmenting NK-mediated killing of target cells by reducing inhibitory KIR signalling without reducing the binding of KIR to HLA-C. As described herein, transduction of negative signaling via KIR, 5 upon binding of KIR to its HLA class I ligand, can involve a ligand-binding induced, conformational reorientation of the KIR molecules allowing interactions to form between adjacent KIRs in specific domains, leading to accelerated clustering. Methods and agents such as mono-clonal antibodies for reducing KIR-mediated inhibition of NK cell cytotoxicity without reducing or blocking HLA-binding by, e.g., reducing or blocking dimerization of KIR, are provided.

30 Claims, 16 Drawing Sheets

OTHER PUBLICATIONS

Wagtmann, N. et al., Killer Cell Inhibitory Receptors Specific for HLA-C and HLA-B Identified by Direct Binding and by Functional Transfer, Immunity, vol. 3, pp. 801-809, 1995.
Spaggiari, G. M. et al., Soluble HLA Class I Induces NK Cell Apoptosis Upon the Engagement of Killer-Activating HLA Class I Receptors Through FasL-Fas Interaction, Blood, 2002, vol. 100, No. 12, pp. 4098-4107.
Spaggiari, G. M. et al., Soluble HLA Class I Molecules Induce Natural Killer Cell Apoptosis Through the Engagement of CD8: Evidence for a Negative Regulation Exerted by Members of the Inhibitory Receptor Superfamily, Blood, 2002, vol. 99, No. 5, pp. 1706-1714.
Lanier, L. L., NK Cell Recognition, Annu. Rev. Immunol., 2005, vol. 23, pp. 225-274.
Karre, K. et al., Selective Rejection of H-2-Deficient Lymphoma Variants Suggests Alternative Immune Defence Strategy, Nature, 1986, vol. 319, pp. 675-678.
Faure, M. et al. Spontaneous Clustering and Tyrosine Phosphorylation of NK Cell Inhibitory Receptor Induced Ligand Binding, The Journal of Immunology, 2003, vol. 170, pp. 6107-6114.
Moretta, A. et al. Function and Specificity of Human Natural Killer Cell Receptors, European Jouronal of Immunogenetics, 1997, vol. 24, pp. 455-468.
Valiante, N. M. et al., Killer Cell Receptors: Keeping Pace with MHC Class I Evolution, Immunological Reviews, 1997 vol. 155, pp. 155-164.
Lanier, L. L., NK Cell Receptors, Annu. Rev. Immunol., 1998, vol. 16, pp. 359-393.
Ruggeri, L. et al., Effectiveness of Donor Natural Killer Cell Alloreactivity in Mismatched Hematopoietic Transplants, Science, 2002, vol. 295, pp. 2097-2100.
Moretta, M. et al., P58 Molecules as Putative Receptors for Major Histocompatibility Complex (MHC) Class I Molecules in Human Natural Killer (NK) Cells. Anti-p58 Antibodies Reconstitute Lysis of MHC Class I-protected Cells in NK Clones Displaying Different Specificities, J. Exp. Med., 1993, vol. 178, pp. 597-604.
Shin, J.S. et al., Monoclonal Antibodies with Various Reactivity to p58 Killer Inhibitory Receptors, Hybridoma, 1999, vol. 18, No. 6, pp. 521-527.
Fan, Q. R. et al., Cobalt-mediated Dimerization of the Human Natural Killer Cell Inhibitory Receptor, J. Biol. Chem., 2000, vol. 275, No. 31, pp. 23700-23706.
Moretta, A. et al., Identification ofFour Subsets of Human CD3⁻CD16⁺Natural Killer (NK) Cells by the Expression of Clonally Distributed Functional Surface Molecules: Correlation Between Subset Assignment of NK Clones and Ability to Mediate Specific Alloantigen Recognition, J. Exp. Med., 1990, vol. 172, pp. 1589-1598.
Ohlen, C. et al., Studies of Sublines Selected for Loss of HLA Expression From an EBV-Transformed Lymphoblastoid Cell Line— Changes in Sensitivity to Cytotoxic T Cells Activated by Allstimulation and Natural Killer Cells Activated by IFN or IL-2[1], J. Immunol., 1989, vol. 142, No. 9, pp. 3336-3341.
Wagtmann, N. et al., Molecular Clones of the p58 NK Cell Receptor Reveal Immunoglobulin-Related Molecules with Diversity in Both the Extra- and Intracellular Domains, Immunity, 1995, vol. 2, pp. 439-449.
Junghans, R. P., XP-002309299, 2003.

Kawauchi, Y. et al., XP-002309300, Yamanouchi Pharm Co. Ltd., 1997.
Yuhan Corp, XP-002309301, 2002.
Warren, H.S. et al., Functional Analysis of CD158b Monoclonal Antibodies Recognizing the Killer Ig-like Receptors KIR2DS2, KIR2DL2 and KIR2DL3, Tissue Antigens, 2000, vol. 55, Supl. 1, pp. 80-81.
Koh, C. Y. et al., NK Inhibitory-Receptor Blockade for Purging of Leukemia: Effects on Hematopoietic Reconstitution, Biology of Blood and Marrow Transplantation, 2002, vol. 8, No. 1, pp. 17-25.
Farag, S. S. et al., Natural Killer Cell Receptors: New Biology and Insights Into the Graft-Versus-Leukemia Effect, Blood, 2002, vol. 100, No. 6, pp. 1935-1947.
Barten, R. et al., Divergent and Convergent Evolution of NK-Cell Receptors, Trends in Immunology, 2001, vol. 22, No. 1, pp. 52-57.
Moretta, A. et al., Activating Receptors and Coreceptors Involved in Human Natural Killer Cell-Mediated Cytolysis, Annu. Rev. Immunol., 2001, vol. 19, pp. 197-223.
Moretta A. et al., Receptors for HLA Class-I Molecules in Human Natural Killer Cells, Annu. Rev. Immunol., 1996, vol. 14, pp. 619-648.
Poggi, A. et al., p40, A Novel Surface Molecule Involved in the Regulation of the Non-Major Histocompatibility Complex-Restricted Cytolytic Activity in Humans, Eur. J. Immunol., 1995, vol. 25, pp. 369-376.
Biassoni, R. Human CD3[31] CD16⁺Natural Killer Cells Express the hGATA=3 T Cell Transcription Factor and an Unrearranged 2.3-kb TcR δ Transcript, Eur. J. Immunol., 1993, vol. 23, pp. 1083-1087.
Boyington, J. C. et al., Crystal Structure of an NK Cell Immunoglobulin-like Receptorin Complex with its Class I MHC Ligand, Nature, 2000, vol. 405, pp. 537-543.
Fan, Q. R. et al. Crystal Structure of the Human Natural Killer Cell Inhibitory Receptor KIR2DL1-HLA-Cw4 Complex, Nature Immunology, 2001, vol. 5, No. 2, pp. 452-460.
Gauthier, L. et al., μ-Surrogate Light Chain Physicochemical Interactions of the Human PreB Cell Receptor: Implications for $V_H$ Repertoire Selection and Cell Signaling at the PreB Cell Stage, J. Immunol., 1999, vol. 162, pp. 41-50.
Colonna, M. et al., Cloning of Immunoglobulin-Superfamily Members Associated with HLA-C and HLA-B Recognition by Human Natural Killer Cells, Science, 1995, vol. 268, pp. 405-408.
Maenaka K. et al., Crystal Structure of the Human p58 Killer Cell Inhibitory Receptor (KIR2DL3) Specific for HLA-Cw3-related MHC Class I, Structure, 1999, vol. 7, No. 4, pp. 391-398.
Pende, D. et al., Identification and Molecular Characterization of NKp30, a Novel Triggering Receptor Involved in Natural Cytotoxicity Mediated by Human Natural Killer Cells, J. Exp. Med., 1999, vol. 190, No. 10, pp. 1505-1516.
Saulquin, X. et al. Crystal Structure of the Human Natural Killer Cell Activating Receptor KIR2DS2 (CD158j), J. Exp. Med., 2003, vol. 197, No. 7, pp. 933-938.
Saunal, H. et al., Mapping of Viral Conformational Epitopes Using Biosensor Measurements, J. Immunol. Method, 1995, vol. 183, pp. 33-41.

* cited by examiner

FIGURE 2A

```
              -2        -1         0         1         2
        3210987654321098765432112345678901234567890123 4567
2DL1    --MSLLVVSMACVGFFLLQGAWPHEGVHRKPSLLAHPGPLVKSEETVILQ
2DL2    --MSLMVVSMACVGFFLLQGAWPHEGVHRKPSLLAHPGRLVKSEETVILQ
2DL3    --MSLMVVSMVCVGFFLLQGAWPHEGVHRKPSLLAHPGPLVKSEETVILQ
2DL4    MSMSPTVIILACLGFFLDQSVWAHVGGQDKPFCSAWPSAVVPQGGHVTLR
2DS1    --MSLTVVSMACVGFFLLQGAWPHEGVHRKPSLLAHPGRLVKSEETVILQ
2DS2    --MSLMVVSMACVGFFLLQGAWPHEGVHRKPSLLAHPGPLVKSEETVILQ
2DS3    --MSLMVISMACVGFFWLQGAWPHEGFRRKPSLLAHPGRLVKSEETVILQ
2DS4    --MSLMVIIMACVGFFLLQGAWPQEGVHRKPSFLALPGHLVKSEETVILQ
2DS5    --MLLMVISMACVAFFLLQGAWPHEGFRRKPSLLAHPGPLVKSEETVILQ
           *    *:  :.*:.**   *..*.: *  : **    * *. :*  .   * *:
DOM1                          11   11
DOM2
```

FIGURE 2B

```
              3         4         5         6         7
        8901234567890123456789012345678901234567890123 4567
2DL1    CWSDVMFEHFLLHREGMFNDTLRLIGEHHDGVSKANFSISRMTQDLAGTY
2DL2    CWSDVRFEHFLLHREGKFKDTLHLIGEHHDGVSKANFSIGPMMQDLAGTY
2DL3    CWSDVRFQHFLLHREGKFKDTLHLIGEHHDGVSKANFSIGPMMQDLAGTY
2DL4    CHYRRGFNIFTLYKKDGVP-----VPELYNRIFWNSFLISPLTPAHAGTY
2DS1    CWSDVMFEHFLLHREGMFNDTLRLIGEHHDGVSKANFSISRMRQDLAGTY
2DS2    CWSDVRFEHFLLHREGKYKDTLHLIGEHHDGVSKANFSIGPMMQDLAGTY
2DS3    CWSDVMFEHFLLHREGTFNDTLRLIGEHIDGVSKANFSIGRMRQDLAGTY
2DS4    CWSDVMFEHFLLHREGKFNNTLHLIGEHHDGVSKANFSIGPMMPVLAGTY
2DS5    CWSDVMFEHFLLHREGTFNHTLRLIGEHIDGVSKGNFSIGRMTQDLAGTY
         *      *: * *:::.        : *   : :    .* *. :    ****
DOM1       111111              1       111
DOM2
```

FIGURE 2C

```
              8         9        10        11        12
      890123456789012345678901234567890123456789012345 67
2DL1  RCYGSVTHSPYQVSAPSDPLDIVIIGLYEKPSLSAQPGPTVLAGENVTLS
2DL2  RCYGSVTHSPYQLSAPSDPLDIVITGLYEKPSLSAQPGPTVLAGESVTLS
2DL3  RCYGSVTHSPYQLSAPSDPLDIVITGLYEKPSLSAQPGPTVLAGESVTLS
2DL4  RCRGFHPHSPTEWSAPSNPLVIMVTGLYEKPSLTARPGPTVRTGENVTLS
2DS1  RCYGSVTHSPYQLSAPSDPLDIVIIGLYEKPSLSAQPGPTVLAGENVTLS
2DS2  RCYGSVTHSPYQLSAPSDPLDIVITGLYEKPSLSAQPGPTVLAGESVTLS
2DS3  RCYGSVPHSPYQFSAPSDPLDIVITGLYEKPSLSAQPGPTVLAGESVTLS
2DS4  RCYGSVPHSPYQLSAPSDPLDMVIIGLYEKPSLSAQPGPTVQAGENVTLS
2DS5  RCYGSVTHSPYQLSAPSDPLDIVITGLYEKPSLPAQPGPTVLAGESVTLS
      ** *  .***  : ****:**  :::  ********.*:***** :**.****
DOM1          1111    1111
DOM2                                    22222222         2 2
```

FIGURE 2D

```
              13        14        15        16        17
      890123456789012345678901234567890123456789012345 67
2DL1  CSSRSSYDMYHLSREGEAHERRLPAGPKVNGTFQADFPLGPATHGGTYRC
2DL2  CSSRSSYDMYHLSREGEAHECRFSAGPKVNGTFQADFPLGPATHGGTYRC
2DL3  CSSRSSYDMYHLSREGEAHERRFSAGPKVNGTFQADFPLGPATHGGTYRC
2DL4  CSSQSSFDIYHLSREGEAHELRLPAVPSINGTFQADFPLGPATHGETYRC
2DS1  CSSRSSYDMYHLSREGEAHERRLPAGTKVNGTFQANFPLGPATHGGTYRC
2DS2  CSSRSSYDMYHLSREGEAHERRFSAGPKVNGTFQADFPLGPATHGGTYRC
2DS3  CSSWSSYDMYHLSTEGEAHERRFSAGPKVNGTFQADFPLGPATQGGTYRC
2DS4  CSSRSSYDMYHLSREGEAHERRLPAVRSINGTFQADFPLGPATHGGTYRC
2DS5  CSSRSSYDMYHLSREGEAHERRLPAGPKVNRTFQADSPLDPATHGGAYRC
      *** **:*:**** ****** *:.*   .:* ****: **.***:* :***
DOM1
DOM2  2 2                          22222 222
```

FIGURE 2E

```
               18        19        20        21        22
      8901234567890123456789012345678901234567890123 4567
2DL1  FGSFHDSPYEWSKSSDPLLVSVTGNPSNSWPSPTEPSSKTGNPRHLHILI
2DL2  FGSFRDSPYEWSNSSDPLLVSVIGNPSNSWPSPTEPSSKTGNPRHLHILI
2DL3  FGSFRDSPYEWSNSSDPLLVSVTGNPSNSWPSPTEPSSETGNPRHLVLI
2DL4  FGSFHGSPYEWSDASDPLPVSVTGNPSSSWPSPTEPSFKTGIARHLHAVI
2DS1  FGSFRDSPYEWSKSSDPLLVSVTGNPSNSWPSPTEPSSETGNPRHLHVLI
2DS2  FGSFRDSPYEWSNSSDPLLVSVTGNPSNSWPSPTEPSSKTGNPRHLHVLI
2DS3  FGSFHDSPYEWSKSSDPLLVSVTGNPSNSWPSPTEPSSKTGNPRHLHVLI
2DS4  FGSFRDAPYEWSNSSDPLLVSVTGNPSNSWPSPTEPSSKTGNPRHLHVLI
2DS5  FGSFRDSPYEWSKSSDPLLVSVTGNSSNSWPSPTEPSSETGNPRHLHVLI
      ****:..:*****.:****  *** **.*.*********.:**..****.:*
DOM1
DOM2                     222222222
```

FIGURE 2F

```
               23        24        25        26        27
      890123456789012345678901234567890123456789012 34567
2DL1  GTSVVIILF-ILLFFLLHRWCSNKKNAAVMDQESAGNRTANSEDSDEQDP
2DL2  GTSVVIILFILL-FFLLHRWCSNKKNAAVMDQESAGNRTANSEDSDEQDP
2DL3  GTSVVIILFILLLFFLLHRWCCNKKNAVVMDQEPAGNRTVNREDSDEQDP
2DL4  RYSVAIILFTILPFFLLHRWCSKKKDAAVMNQEPAGHRTVNREDSDEQDP
2DS1  GTSVVKIPFTILLFFLLHRWCSDKKNAAVMDQEPAGNRTVNSEDSDEQDH
2DS2  GTSVVKIPFTILLFFLLHRWCSNKKNAAVMDQEPAGNRTVNSEDSDEQDH
2DS3  GTSVVKLPFTILLFFLLHRWCSDKKNASVMDQGPAGNRTVNREDSDEQDH
2DS4  GTSVVKIPFTILLFFLLHRWCSDKKNAAVMDQEPAGNRTVNSEDSDEQDH
2DS5  GTSVVKLPFTILLFFLLHRWCSNKKNASVMDQGPAGNRTVNREDSDEQDH
          **.: * :* ********..**:* **:* .**:**.* *******
DOM1
DOM2
```

FIGURE 2G

```
            28         29         30         31         32
     8901234567890123456789012345678901234567890123 4567
2DL1 QEVTYTQLNHCVFTQRKITRPSQRPKTPPTDIIVYTELPNAESRSKVVSC
2DL2 QEVTYTQLNHCVFTQRKITRPSQRPKTPPTDIIVYAELPNAESRSKVVSC
2DL3 QEVTYAQLNHCVFTQRKITRPSQRPKTPPTDIIVYTELPNAEP-------
2DL4 QEVTYAQLDHCIFTQRKITGPSQRSKRPSTDTSVCIELPNAEPRALSPAH
2DS1 QEVSYA--------------------------------------------
2DS2 QEVSYA--------------------------------------------
2DS3 QEVSYA--------------------------------------------
2DS4 QEVSYA--------------------------------------------
2DS5 QEVSYA--------------------------------------------
     ***:*:

DOM1
DOM2
```

FIGURE 2H

```
             33         34         35
     890123456789012345678901234567 89
2DL1 P---------------------------------
2DL2 P---------------------------------
2DL3 ----------------------------------
2DL4 EHHSQALMGSSRETTALSQTQLASSHVPAAGI
2DS1 ----------------------------------
2DS2 ----------------------------------
2DS3 ----------------------------------
2DS4 ----------------------------------
2DS5 ----------------------------------

DOM1
DOM2
```

FIGURE 3A

```
         -2        -1         0         1         2
         10987654321098765432112345678901234567890123456789
3DL1     MSLMVVSMACVGLFLVQRAGPHMGGQDKPFLSAWPSAVVPRGGHVTLRCH
3DL2     MSLTVVSMACVGFFLLQGAWPLMGGQDKPFLSARPSTVVPRGGHVALQCH
3DL3     MSLMVVSMACVGFFLLEGPWPHVGGQDKPFLSAWPGTVVSEGQHVTLQCR
3DS1     MSLMVVSMACVGLFLVQRAGPHMGGQDKPFLSAWPSAVVPRGGHVTLRCH
2DL1     MSLLVVSMACVGFFLLQGAWPHEG--------------------------
         ***.********:**::.*  *
DOM1                                11
DOM2
```

FIGURE 3B

```
          3         4         5         6         7
         01234567890123456789012345678901234567890123456789
3DL1     YRHRFNNFMLYKEDRIHIPIFHGRIFQESFNMSPVTTAHAGNYTCRGSHP
3DL2     YRRGFNNFMLYKEDRSHVPIFHGRIFQESFIMGPVTPAHAGTYRCRGSRP
3DL3     SRLGFNEFSLSKEDGMPVPELYNRIFRNSFLMGPVTPAHAGTYRCCSSHP
3DS1     YRHRFNNFMLYKEDRIHVPIFHGRIFQEGFNMSPVTTAHAGNYTCRGSHP
2DL1     --------------------------------------------------

DOM1
DOM2
```

FIGURE 3C

```
               8         9         10        11        12
               0123456789012345678901234567890123456789012345678 9
3DL1   HSPTGWSAPSNPVVIMVTGNHRKPSLLAHPGPLVKSGERVILQCWSDIMF
3DL2   HSLTGWSAPSNPLVIMVTGNHRKPSLLAHPGPLLKSGETVILQCWSDVMF
3DL3   HSPTGWSAPSNPVVIMVTGVHRKPSLLAHPGPLVKSGETVILQCWSDVRF
3DS1   HSPTGWSAPSNPMVIMVTGNHRKPSLLAHPGPLVKSGERVILQCWSDIMF
2DL1   -------------------VHRKPSLLAHPGPLVKSEETVILQCWSDVMF
                          *************:** * ********: *
DOM1                        11                        1111
DOM2
```

FIGURE 3D

```
               13        14        15        16        17
               0123456789012345678901234567890123456789012345678 9
3DL1   EHFFLHKEGISKDPSRLVGQIHDGVSKANFSIGPMMLALAGTYRCYGSVT
3DL2   EHFFLHREGISEDPSRLVGQIHDGVSKANFSIGPLMPVLAGTYRCYGSVP
3DL3   ERFLLHREGITEDPLRLIGQLHDAGSQVNYSMGPMTPALAGTYRCFGSVT
3DS1   EHFFLHKEWISKDPSRLVGQIHDGVSKANFSIGSMMRALAGTYRCYGSVT
2DL1   EHFLLHREGMFNDTLRLIGEHHDGVSKANFSISRMTQDLAGTYRCYGSVT
       *:*:**:*  :  :*. **:*: **. *:.*:*:. :   *******:***.
DOM1   11              1       111                       11
DOM2
```

FIGURE 3E

```
            18        19        20        21        22
      0123456789012345678901234567890123456789012345678 9
3DL1  HTPYQLSAPSDPLDIVVTGPYEKPSLSAQPGPKVQAGESVTLSCSSRSSY
3DL2  HSPYQLSAPSDPLDIVITGLYEKPSLSAQPGPTVQAGENVTLSCSSWSSY
3DL3  HLPYELSAPSDPLDIVVVGLYGKPSLSAQPGPTVQAGENVTLSCSSRSLF
3DS1  HTPYQLSAPSDPLDIVVTGLYEKPSLSAQPGPKVQAGESVTLSCSSRSSY
2DL1  HSPYQVSAPSDPLDIVIIGLYEKPSLSAQPGPTVLAGENVTLSCSSRSSY
      * **::**********:  *  * **********.* ***.******* * :
DOM1  11   1111
DOM2                              22222222       2 2 2 2
```

FIGURE 3F

```
            23        24        25        26        27
      0123456789012345678901234567890123456789012345678 9
3DL1  DMYHLSREGGAHERRLPAVRKVNRTFQADFPLGPATHGGTYRCFGSFRHS
3DL2  DIYHLSREGEAHERRLRAVPKVNRTFQADFPLGPATHGGTYRCFGSFRAL
3DL3  DIYHLSREAEAGELRLTAVLRVNGTFQANFPLGPVTHGGNYRCFGSFRAL
3DS1  DMYHLSREGGAHERRLPAVRKVNRTFQADFPLGPATHGGTYRCFGSFRHS
2DL1  DMYHLSREGEAHERRLPAGPKVNGTFQADFPLGPATHGGTYRCFGSFHDS
      *:******. * * ** *  :** ****:*****.****.*******:
DOM1
DOM2                           22222 222
```

FIGURE 3G

```
            28        29        30        31        32
     0123456789012345678901234567890123456789012345678901234567890123456789
3DL1 PYEWSDPSDPLLVSVTGNPSSSWPSPTEPSSKSGNPRHLHILIGTSVVII
3DL2 PCVWSNSSDPLLVSVTGNPSSSWPSPTEPSSKSGICRHLHVLIGTSVVIF
3DL3 PHAWSDPSDPLPVSVTGNS----------------RYLHALIGTSVVII
3DS1 PYEWSDPSDPLLVSVTGNPSSSWPSPTEPSSKSGNLRHLHILIGTSVVKI
2DL1 PYEWSKSSDPLLVSVTGNPSNSWPSPTEPSSKTGNPRHLHILIGTSVVII
     *  **..**** ******.              *:** ******* :
DOM1
DOM2           222222222
```

FIGURE 3H

```
            33        34        35        36        37
     0123456789012345678901234567890123456789012345678901234567890123456789
3DL1 LFILLLFFLLHLWCSNKKNAAVMDQEPAGNRTANSEDSDEQDPEEVTYAQ
3DL2 LFILLLFFLLYRWCSNKKNAAVMDQEPAGDRTVNRQDSDEQDPQEVTYAQ
3DL3 PFAILLFFLLHRWCANKKNAVVMDQEPAGNRTVNREDSDEQDPQEVTYAQ
3DS1 PFTILLFFLLHRWCSNKKNAAVMDQEPAGNRSE-----------------
2DL1 LFILL-FFLLHRWCSNKKNAAVMDQESAGNRTANSEDSDEQDPQEVTYTQ
     * :* ****: **:*****.*****.**:*:
DOM1
DOM2
```

FIGURE 3I

```
              38        39        40        41        42
     0123456789012345678901234567890123456789012345678 9
3DL1 LDHCVFTQRKITRPSQRPKTPPTDTILYTELPNAKPRSKVVSCP------
3DL2 LDHCVFIQRKISRPSQRPKTPLTDTSVYTELPNAEPRSKVVSCPRAPQSG
3DL3 LNHCVFTQRKITRPSQRPKTPPTDTSV-----------------------
3DS1 -------QRGF---------------------------------------
2DL1 LNHCVFTQRKITRPSQRPKTPPTDIIVYTELPNAESRSKVVSCP------
           **  :

DOM1
DOM2
```

YTS

YTS-2DL1

1-26F117

FIGURE 7
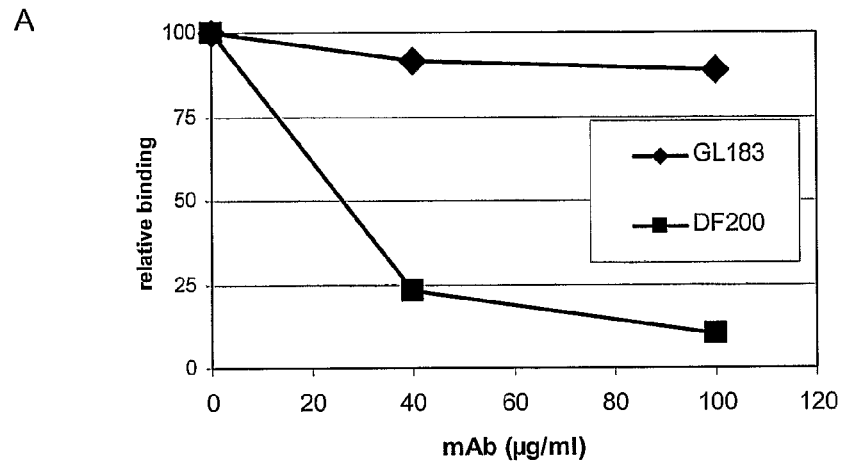
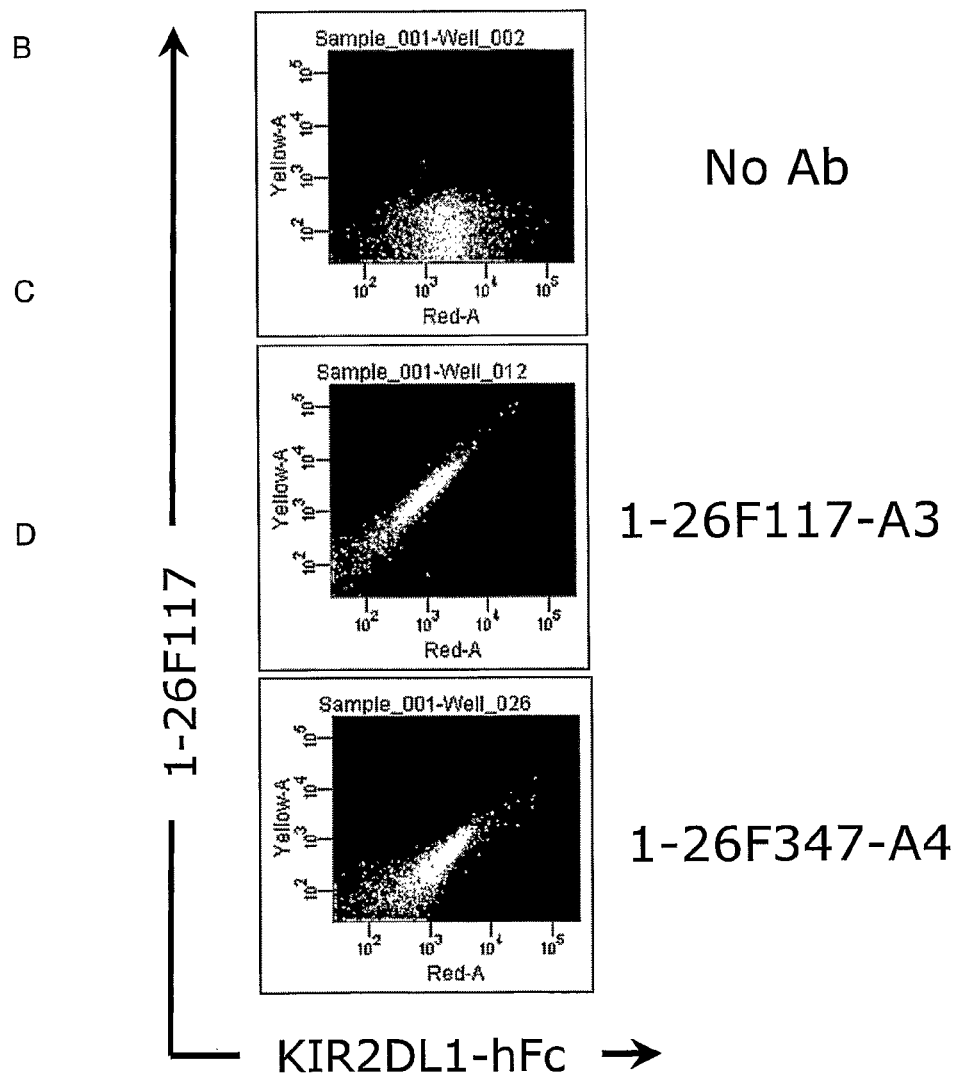

KIR-BINDING AGENTS AND METHODS OF USE THEREOF

CROSS-REFERENCE TO RELATED APPLICATIONS

This application is a 35 U.S.C. §371 national stage application of International Patent Application PCT/EP2006/050073 published as WO 2006/072626, filed Jan. 6, 2006, which claimed priority of Danish Patent Application PA 2005 00021, filed Jan. 6, 2005; this application further claims priority under 35 U.S.C. §119 of U.S. Provisional Application 60/642,626, filed Jan. 10, 2005.

FIELD OF THE INVENTION

The present invention relates to agents and methods that are capable of augmenting NK-mediated killing of target cells by reducing inhibitory KIR signalling. Further, the present invention relates to the use of such agents for the preparation of medicaments as well as methods of producing antibodies and hybridomas and transfected cell lines producing these antibodies.

BACKGROUND OF THE INVENTION

Natural killer (NK) cells are a sub-population of lymphocytes, involved in immunity and in the host immune surveillance system.

NK cells are mononuclear cell that develop in the bone marrow from lymphoid progenitors, and morphological features and biological properties typically include the expression of the cluster determinants (CDs) CD16, CD56, and/or CD57; the absence of the alpha/beta or gamma/delta TCR complex on the cell surface; the ability to bind to and kill target cells that fail to express "self" major histocompatibility complex (MHC)/human leukocyte antigen (HLA) proteins; and the ability to kill tumor cells or other diseased cells that express ligands for activating NK receptors. NK cells are characterized by their ability to bind and kill several types of tumor cell lines without the need for prior immunization or activation. NK cells can also release soluble proteins and cytokines that exert a regulatory effect on the immune system; and can undergo multiple rounds of cell division and produce daughter cells with similar biologic properties as the parent cell. Upon activation by interferons and/or cytokines, NK cells mediate the lysis of tumor cells and of cells infected with intracellular pathogens by mechanisms that require direct, physical contacts between the NK cell and the target cell. Lysis of target cells involves the release of cytotoxic granules from the NK cell onto the surface of the bound target, and effector proteins such as perforin and granzyme B that penetrate the target plasma membrane and induce apoptosis or programmed cell death. Normal, healthy cells are protected from lysis by NK cells.

Based on their biological properties, various therapeutic and vaccine strategies have been proposed in the art that rely on a modulation of NK cells. However, NK cell activity is regulated by a complex mechanism that involves both stimulating and inhibitory signals.

Briefly, the lytic activity of NK cells is regulated by various cell surface receptors that transduce either positive or negative intracellular signals upon interaction with ligands on the target cell. The balance between positive and negative signals transmitted via these receptors determines whether or not a target cell is lysed (killed) by a NK cell. NK cell stimulatory signals can be mediated by Natural Cytotoxicity Receptors (NCR) such as NKp30, NKp44, and NKp46; as well as CD94/NKG2C receptors, NKG2D receptors, certain activating Killer Ig-like Receptors (KIRs), and other activating NK receptors (Lanier, Annual Review of Immunology 2005; 23:225-74). NK cell inhibitory signals can be mediated by receptors like Ly49, CD94/NKG2A, as well as certain inhibitory KIRs, which recognize major histocompatibility complex (MHC) class I-molecules (Kärre et al., Nature 1986; 319:675-8; Öhlén et al, Science 1989; 246:666-8). These inhibitory receptors bind to polymorphic determinants of MHC class I molecules (including HLA class I) present on other cells and inhibit NK cell-mediated lysis.

KIRs have been characterized in humans and non-human primates, and are polymorphic type 1 trans-membrane molecules present on certain subsets of lymphocytes, including NK cells and some T cells. KIRs interact with determinants in the alpha 1 and 2 domains of the MHC class I molecules and, as described above, distinct KIRs are either stimulatory or inhibitory for NK cells.

The nomenclature for KIRs is based upon the number of extracellular domains (KIR2D and KIR3D having two and three extracellular Ig-domains, respectively) and whether the cytoplasmic tail is long (KIR2DL or KIR3DL) or short (KIR2DS or KIR3DS). The presence or absence of a given KIR is variable from one NK cell to another within the NK population present in a single individual. Among humans, there is also a relatively high level of polymorphism of KIR genes, with certain KIR genes being present in some, but not all individuals. The expression of KIR alleles on NK cells is stochastically regulated, meaning that, in a given individual, a given lymphocyte may express one, two, or more different KIRs, depending on the genotype of the individual. The NK cells of a single individual typically express different combinations of KIRs, providing a repertoire of NK cells with different specificities for MHC class I molecules.

Certain KIR gene products cause stimulation of lymphocyte activity when bound to an appropriate ligand. The activating KIRs all have a short cytoplasmic tail with a charged transmembrane residue that associates with an adapter molecule having an Immunoreceptor Tyrosine-based Activation Motifs (ITAMs) which transduce stimulatory signals to the NK cell. By contrast, inhibitory KIRs have a long cytoplasmic tail containing Immunoreceptor Tyrosine-based Inhibitory Motif (ITIM), which transduce inhibitory signals to the NK cell upon engagement of their MHC class I ligands. It has been reported that mixing NK cells with insect cells expressing HLA-C was sufficient to induce clustering of KIR, and phosphorylation of KIR and SHP-1 (Faure et al., J Immunol 2003; 170:6107-6114). It has also been reported that KIR2DL1 dimerized in the presence of Co(2+), and that replacement of the amino-terminal H is residue by Ala abolished the ability of KIR2DL1 to bind Co(2+) (Fan et al., J. Biol. Chem. 2000. 98:1734).

The known inhibitory KIRs include members of the KIR2DL and KIR3DL subfamilies. Inhibitory KIRs having two Ig domains (KIR2DL) recognize HLA-C allotypes: KIR2DL2 (formerly designated p58.2) and the closely related, allelic gene product KIR2DL3 both recognize "group 1" HLA-C allotypes (including HLA-Cw1, -3, -7, and -8), whereas KIR2DL1 (p58.1) recognizes "group 2" HLA-C allotypes (such as HLA-Cw2, -4, -5, and -6). The recognition by KIR2DL1 is dictated by the presence of a Lys residue at position 80 of HLA-C alleles. KIR2DL2 and KIR2DL3 recognition is dictated by the presence of an Asn residue at position 80 in HLA-C. Importantly, the great majority of HLA-C alleles have either an Asn or a Lys residue at position 80. Therefore, KIR2DL1, -2, and -3 collectively recognize essentially all HLA-C allotypes found in humans. One KIR with three Ig domains, KIR3DL1 (p70), recognizes an epitope shared by HLA-Bw4 alleles. Finally, KIR3DL2 (p140), existing constitutively as a disulfide-bonded homodimer of molecules with three Ig domains, recognizes HLA-A3 and -A1.

Although multiple inhibitory KIRs and/or other MHC class I-specific inhibitory receptors (Moretta et al, Eur J. Immunogenet. 1997; 24(6):455-68; Valiante et al, Immunol Rev 1997; 155:155-64; Lanier, Annu Rev Immunol 1998; 16:359-93) may be co-expressed by NK cells, in any given individual's NK repertoire there are cells that express only a single KIR, and thus are inhibited only by specific MHC class I alleles (or alleles belonging to the same group of MHC class I allotypes). Human MHC class I molecules often are referred to as Human Histocompatibility Antigen (HLA) class I.

NK cell populations or clones that are KIR-ligand mismatched with respect to their targets, i.e., that express KIRs which do not recognize any HLA molecule of a host, have been shown to mediate potent, life-saving anti-tumor responses after allogeneic bone-marrow transplantation in leukemia patients (Ruggeri et al., Science 2002, 295:2097-2100). The underlying mechanism is believed to be that HLA mismatched hematopoietic transplantation leads to the expansion of donor-derived NK cells expressing KIR which do not recognize any HLA ligands in the recipient, and thus are not inhibited via KIR. These allogeneic NK clones exert potent anti-tumor activity. This response is very strong in patients diagnosed with acute myeloid leukaemia (AML), and treated with KIR-MHC mismatched haplo-identical transplants. One way of reproducing this effect by pharmacological treatment of a patient would be to administer reagents that block the KIR/HLA interaction to activate the patient's endogenous NK cells.

Certain monoclonal antibodies specific for KIR2DL1 have been shown to block the interaction of KIR2DL1 with "group 2" HLA-C allotypes, such as HLA-Cw4 (Moretta et al., J Exp Med 1993; 178:597-604), and to promote NK-mediated lysis of target cells that express those HLA-C allotypes. Monoclonal antibodies against KIR2DL2/3 that block the interaction of KIR2DL2/3 with HLA-Cw3 or similar allotypes have also been described (Moretta et al., J Exp Med 1993; 178: 597-604). Watzl et al. (Tissue Antigens 2000; 56:240-247) produced cross-reacting murine antibodies recognizing multiple isotypes of KIRs, but those antibodies did not potentiate the lytic activity of NK cells. Further, Spaggiari et al. (Blood 2002; 99:1706-1714 and Blood 2002; 100:4098-4107) carried out experiments utilizing murine mono-clonal antibodies against various KIRs. One of those antibodies, NKVSF1 (also known as Pan2D), was reported to recognize a common epitope of KIR2DL1 (CD158a), KIR2DL2 (CD158b) and KIR2DS4 (p50.3). Shin et al. (Hybridoma 1999; 18:521-7) also reported the production of two monoclonal antibodies, denoted A210 and A803g, capable of binding to all of KIR2DL1, KIR2DL3, and KIR2DS4. None of A210 and A803g interfered with the binding between KIR and HLA-C or was capable of blocking inhibitory KIR-signalling.

WO2005003172, WO2005003168, and WO2005009465 describe KIR2DL1 and KIR2DL2/3 cross-reactive antibodies such as, e.g., DF200, 1-7F9, 1-4F1, 1-6F5, and 1-6F1, and that DF200 and 1-7F9 enhance NK cell cytotoxicity.

WO0050081 describes a method for desensitizing, e.g., a B cell or NK cell receptor by contacting it with a regulatory compound that inhibits association with a transducer component.

WO0002583 describes methods of treating, e.g., psoriasis by blocking binding of an NK-T cell receptor to an MHC molecule.

WO9849292 and WO2005060375 relate generally to KIR or other NK cell receptors, and antibodies thereto.

However, previous efforts to isolate agents, such as antibodies, capable of neutralizing KIR-mediated inhibition of NK cell cytotoxicity have focused on blocking the interaction of KIR with its corresponding HLA molecule such as, e.g., HLA-C. A need still exists for alternative targets for therapeutic agents capable of activating NK-cells.

The present invention provides such novel targets, as well as novel agents binding such targets, and novel methods of use thereof.

SUMMARY OF THE INVENTION

The present invention is based, in part, on the discovery of novel agents that bind determinants of one or more human inhibitory KIRs, and cause potentiation of NK cells expressing at least one of those KIR gene products by a novel mechanism that does not involve blocking the binding between KIR and its HLA-C ligand. In one embodiment, the agents reduce KIR-mediated inhibition of NK-cell cytotoxicity by reducing or blocking dimerization of KIR, which, in turn, cause potentiation of NK cell activity.

Accordingly, in one aspect, the present invention provides an agent that binds or interacts with an extracellular portion of an inhibitory human Killer IgG-like Receptor (KIR), wherein the agent reduces KIR-mediated inhibition of NK cell cytotoxicity without detectably reducing binding between the KIR and an HLA class I-ligand of the KIR. In one embodiment, the agent reduces KIR-mediated inhibition of NK cell cytotoxicity by reducing or blocking clustering of KIR. In another embodiment, the agent also or alternatively reduces KIRmediated inhibition of NK cell cytotoxicity by reducing or blocking dimerization of KIR.

In one embodiment, the agent reduces or blocks interaction between interaction sites associated with Domain 1. The interaction site associated with Domain 1 may comprise at least one amino acid residue corresponding to, e.g., one of residues 1-92 of SEQ ID NO:14. For example, the interaction site associated with Domain 1 can comprise at least one amino acid residue corresponding to H1, E2, H5, R6, D31, V32, M33, F34, E35, H36, H50, D57, G58, V59, V83, T84, H85, S86, Q89, L90, S91, or A92.

In another embodiment, the agent reduces or blocks interaction between interaction sites associated with Domain 2. The interaction site associated with Domain 2 may comprise at least one amino acid residue corresponding to, e.g., one of residues 108-200 of SEQ ID NO:14. For example, the interaction site associated with Domain 2 can comprise at least one amino acid residue corresponding to P108, S109, L110, S111, A112, Q113, P114, L114, G115, T125, S127, S129, R131, K155, V156, N157, G158, T159, Q161, A162, D163, S192, D193, P194, L195, L196, V197, S198, V199 or T200. For example, the interaction site associated with Domain 2 of KIR2DL1 can comprises amino acid residues L110, S111, A112, Q113, P/L114 (indicating that residue 114 can be P or L), and L195.

In any of the above embodiments, the agent provided by the invention may, for example, reduce or block at least one of homodimerization, heterodimerization, or both, among members of the KIR family. For example, the agent may reduce or block homodimerization of KIR2DL1.

The agent may be any suitable compound such as, for example, an antibody or a fragment thereof. The antibody fragment can be selected from, e.g., a Fab fragment, a Fab' fragment, a Fab'-SH fragment, a F(ab')2 fragment, an Fv fragment, a diabody, a single-chain antibody fragment, and a multispecific antibody. The antibody can be, for example, a human, a humanized or a chimeric antibody, or the antibody fragment derived from such an antibody.

In one embodiment, the agent is a cross-reactive KIR-binding agent, such as, e.g., a cross-reactive anti-KIR antibody or a fragment thereof. The agent may, for example, bind to each of KIR2DL1 and KIR2DL3. In one embodiment, the agent may, for example, be an antibody or antibody fragment competing with an antibody comprising a VH sequence of SEQ ID NO:17 and a VL sequence of SEQ ID NO:18 in binding to at least one of KIR2DL1 and KIR2DL3. For example, the agent can be an antibody or antibody fragment comprising a VH sequence of SEQ ID NO:17 and a VL sequence of SEQ ID NO:18. In an alternative embodiment, the agent may be an antibody or antibody fragment competing with an antibody comprising a VH sequence of SEQ ID NO:21 and a VL sequence of SEQ ID NO:18 in binding to at least one of KIR2DL1 and KIR2DL3. For example, the agent can be an antibody or antibody fragment comprising a VH sequence of SEQ ID NO:21 and a VL sequence of SEQ ID NO:18.

In another aspect, the invention provides for the use of an agent according to the invention as a medicament.

In another aspect, the invention provides for a pharmaceutical composition comprising an agent according to the invention in an amount effective to detectably potentiate NK cell cytotoxicity in a patient, and one or more pharmaceutically acceptable carriers or diluents. In one embodiment, the pharmaceutical formulation further comprises a therapeutic agent selected from an immunomodulatory agent, a hormonal agent, a chemotherapeutic agent, an anti-angiogenic agent, an apoptotic agent, and an antibody that blocks HLA-binding to an inhibitory KIR receptor.

In another aspect, the invention provides for a method of reducing KIR-mediated inhibition of NK cell cytotoxicity by contacting an NK cell with an effective amount of an agent according to the invention. The agent may, for example, reduce or block dimerization of KIR. The agent may also be a monoclonal anti-KIR antibody or a fragment thereof. IN one embodiment, the agent competes with an antibody comprising a VH sequence of SEQ ID NO:17 and a VL sequence of SEQ ID NO:18 in binding to at least one of KIR2DL1 and KIR2DL3. In another embodiment, the agent competes with an antibody comprising a VH sequence of SEQ ID NO:21 and a VL sequence of SEQ ID NO:18 in binding to at least one of KIR2DL1 and KIR2DL3.

In another aspect, the invention provides for the use of an agent according to the invention for the preparation of a medicament for treatment of a cancer, an infectious disease, a viral infection, or an immune disorder. In one embodiment, the medicament is for treating a cancer. In this embodiment, the cancer may, for example, be selected from Acute and Chronic Myeloid Leukemia (AML and CML), Acute Lymphoid Leukemia (ALL), Myelodysplastic syndrome, Non-Hodgkins Lymphoma (NHL), Multiple Myeloma, Renal Cell Carcinoma, Malignant Melanoma, and Colorectal Cancer. In an alternative embodiment, the medicament is for treating a viral infection is caused by a virus selected from Human Immunodeficiency Virus (HIV), Hepatitis C Virus (HCV), and Ebola virus.

In another aspect, the invention provides for a method for the treatment of cancer, the method comprising administering to a subject suffering from cancer an effective amount of an agent according to the invention. The agent can be, for example, a human, humanized, or chimeric cross-reactive monoclonal anti-KIR antibody or fragment thereof. In one embodiment, the agent competes with an antibody comprising a VH sequence of SEQ ID NO:17 and a VL sequence of SEQ ID NO:18 in binding to at least one of KIR2DL1 and KIR2DL3. In another embodiment, the agent competes with an antibody comprising a VH sequence of SEQ ID NO:21 and a VL sequence of SEQ ID NO:18 in binding to at least one of KIR2DL1 and KIR2DL3. The method may further comprising administering a therapeutic agent selected from an immunomodulatory agent, a hormonal agent, a chemotherapeutic agent, an anti-angiogenic agent, an apoptotic agent, and an antibody that blocks HLA-binding to an inhibitory KIR receptor.

In another aspect, the invention provides an agent capable of neutralizing KIR mediated inhibition of NK cell cytotoxicity by: a) producing a pool of candidate agents; b) selecting any candidate agent that binds or interacts with the extracellular portion of an inhibitory KIR; and c) selecting any candidate agent from step b) that is capable of neutralizing KIR-mediated inhibition of NK cell cytotoxicity without reducing binding between the inhibitory KIR and an HLA class I-ligand of the KIR; wherein the order of steps b) and c) are optionally reversed. In one embodiment, the method further comprises a step of selecting a cross-reactive KIR-binding agent. The agent may be, for example, a monoclonal antibody or fragment thereof.

In another aspect, the invention provides for a method for producing an antibody or an antibody fragment that is capable of reducing KIR-mediated inhibition of NK cell cytotoxicity, comprising the steps of: a) immunizing a non-human animal with an immunogenic composition comprising at least an extracellular portion of a KIR; b) preparing antibodies from the immunized animal, wherein the antibodies bind the KIR; c) selecting any antibody from (b) that is capable of neutralizing KIR-mediated inhibition of NK cell cytotoxicity without reducing binding between the inhibitory KIR and an HLA class I-ligand of the KIR; and d) optionally preparing a fragment of the antibody.

In another aspect, the invention provides for an isolated antibody or antibody fragment competing with an antibody comprising a VH sequence of SEQ ID NO:17 and a VL sequence of SEQ ID NO:18 in binding to at least one of KIR2DL1 and KIR2DL3. In one embodiment, the antibody or antibody fragment binds to the same KIR2DL1 epitope as an antibody comprising a VH sequence of SEQ ID NO:17 and a VL sequence of SEQ ID NO:18 in binding to at least one of KIR2DL1 and KIR2DL3. In another embodiment, the antibody or antibody fragment comprises a CDR H1 region corresponding to residues 31-35 of SEQ ID NO:17, a CDR H2 corresponding to residues 50-66 of SEQ ID NO:17, a CDR H3 corresponding to residues 99-108 of SEQ ID NO:17; a CDR L1 corresponding to residues 24-34 of SEQ ID NO:18; a CDR L2 corresponding to residues 50-56 of SEQ ID NO:18, and a CDR L3 corresponding to residues 89-97 of SEQ ID NO:18. In another embodiment, the antibody or antibody fragment comprises a VH sequence of SEQ ID NO:17 and a VL sequence of SEQ ID NO:18.

In another aspect, the invention provides for an isolated antibody or antibody fragment competing with an antibody comprising a VH sequence of SEQ ID NO:21 and a VL sequence of SEQ ID NO:18 in binding to at least one of KIR2DL1 and KIR2DL3. In one embodiment, the antibody or antibody fragment binds to the same KIR2DL1 epitope as an anti-body comprising a VH sequence of SEQ ID NO:21 and a VL sequence of SEQ ID NO:18 in binding to at least one of KIR2DL1 and KIR2DL3. In another embodiment, the antibody or antibody fragment comprises a CDR H1 region corresponding to residues 31-35 of SEQ ID NO:21, a CDR H2 corresponding to residues 50-66 of SEQ ID NO:21, a CDR H3 corresponding to residues 98-103 of SEQ ID NO:21; a CDR L1 corresponding to residues 24-34 of SEQ ID NO:18; a CDR L2 corresponding to residues 50-56 of SEQ ID NO:18, and a CDR L3 corresponding to residues 89-97 of SEQ ID NO:18. In another embodiment, the antibody or antibody fragment comprises a VH sequence of SEQ ID NO:21 and a VL sequence of SEQ ID NO:18.

The invention also provides for a nucleotide sequence encoding the antibody or antibody fragment according to any of the preceding aspects, an expression vector comprising such a nucleotide sequence, a host cell transfected with such a vector, and a method of producing an antibody comprising culturing such a host cell under conditions suitable for expression of the antibody.

These and other aspects of the invention are described in the following sections.

DESCRIPTION OF THE DRAWINGS

FIGS. 2A-2H show alignment of KIR2DL1 (SEQ ID NO:1), 2DL2 (SEQ ID NO:2), 2DL3 (SEQ ID NO:3), 2DL4 (SEQ ID NO:4), 2DS1 (SEQ ID NO:5), 2DS2 (SEQ ID NO:6), 2DS3 (SEQ ID NO:7), 2DS4 (SEQ ID NO:8), and 2DS5 (SEQ ID NO:9) sequences with indication of the corresponding residues of the interaction sites associated with Domain1 and Domain2.

FIGS. 3A to 3I show alignment of 3DL1 (SEQ ID NO:10), 3DL2 (SEQ ID NO:11), 3DL3 (SEQ ID NO:12), 3DS1 (SEQ ID NO:13), and 2DL1 (SEQ ID NO:1), with indication of the corresponding residues of the interaction sites associated with Domain1 and Domain 2.

FIG. 7 shows the results of a competition assay testing binding of KIR2DL 1 to HLA-Cw4 in the presence of various anti-KIR mAbs. KIR2DL1-hFc (20 µg/ml final concentration) was pre-incubated in the presence or absence of supernatants of sub-cloned anti-KIR hybridomas, or in the presence of control antibodies. The binding of KIR2DL1-hFc to HLA-Cw4 on LCL 721.221-Cw4 cells was then studied using flow-cytometry (FACSarray). In the presence of a mAb interfering with KIR-HLA binding, less KIR2DL1-hFc binds to LCL 72L221-Cw4 cells in comparison with KIR2DL1-hFc binding in the absence of mAb, resulting in a shift to the left on the X-axis in the dot-plot. (A) When pre-incubated with DF200, KIR2DL1-hFc binding to HLA-Cw4 was competed in a DF200-dose-dependent fashion, whereas KIR2DL1-hFc-binding was not competed with the KIR2DL2-specific mAb GL183 (controls). When pre-incubated with 1-26F117-A3 (B) or 1-26F117-A4 (C), KIR2DL1-hFc was not prevented from binding to HLA-Cw4. Instead, LCL 721.221-Cw4 cells were bound by KIR2DL1-hFc/1-26F117-A3 or KIR2DL1-hFc/1-26F117-A4 complexes, as indicated by double-positive staining of LCL 721.221-Cw4 in the dot-plots, confirming that HLA-Cw4 and 1-26F117-A3, or HLA-Cw4 and 1-26F117-A4, can bind simultaneously to KIR2DL1. (D) Control (no mAb).

DEFINITIONS

Figure 1A:
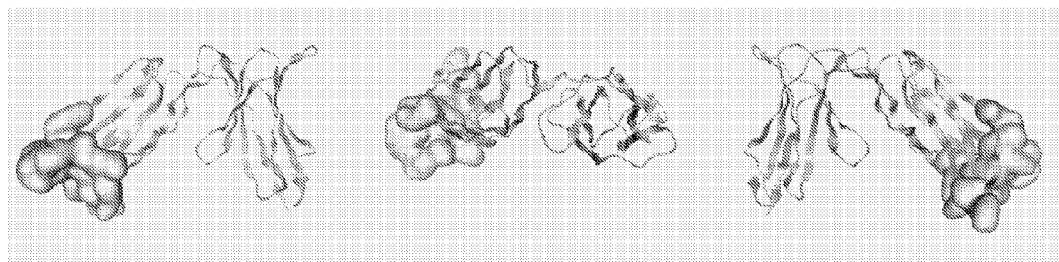
FIG. 1A illustrates the location of the interaction site associated with Domain 1 on the structure of KIR2DL1 (1 NKR.pdb) with views from the front (D1 left, D2 right), top (D1 left D2 right) and back (D2 left, D1 right) respectively.

An "agent" according to the present invention comprises small molecules, polypeptides, proteins, antibodies or antibody fragments. Small molecules, in the context of the present invention, mean in one embodiment chemicals with molecular weight smaller than 1000 Daltons, particularly smaller than 800 Daltons, more particularly smaller than 500 Daltons.

The term "polypeptide" is not meant herein to refer to a specific length of the encoded product and, therefore, encompasses peptides, oligopeptides, and proteins. The polypeptide may also be a naturally occurring allelic or engineered variant of a polypeptide, as well as proteins in general.

The term "antibody", as used herein, is intended to refer to immunoglobulin molecules that have the ability to specifically bind to an antigen (e.g., KIR). Unless otherwise indicated or clearly contradicted by context, the term "antibody"

includes, but is not limited to, full-length antibodies, antibody fragments, and antibody derivatives; monoclonal and polyclonal antibodies; human and non-human antibodies; as well as humanized and chimeric forms of non-human antibodies.

The term "antibody fragment", as used herein, means a molecule comprising one or more fragments of an antibody which retains the ability to specifically bind to an antigen (e.g., KIR). Examples of binding fragments encompassed within the term "antibody fragment" include (i) a Fab fragment, a monovalent fragment consisting of the VL, VH, CL and CH I domains; (ii) F(ab)$_2$ and F(ab')2 fragments, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), (vi) single chain Fv (scFv) (see e.g., Bird et al. (1988) Science 242:423-426: and Huston et al. (1988) Proc. Natl. Acad. Sci. USA 85:5879-5883); (vii) diabodies, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123); and (viii) monovalent antibodies comprising one of the heavy chain-light chain pairs (antibodies of some IgG subclasses such as, e.g., IgG4, are known to spontaneously "split" into two monovalent fragments).

The term "antibody derivative" as used herein, is intended to designate a variant of a full-length antibody or antibody fragment which retains the ability of the parent molecule to specifically bind to an antigen (e.g., KIR), in which one or more of the amino acids of the parent molecule have been chemically modified, e.g., by alkylation, PEGylation, acylation, ester formation or amide formation or the like. This includes, but is not limited to, PEGylated antibodies, cysteine-PEGylated antibodies, and variants thereof.

In the context of the present invention, "binds" or "interacts" or "reacts" means any binding of an agent (e.g. an antibody) to its determinant (e.g. an epitope) with a dissociation constant Kd lower than $10^{-4}$ M. The terms "binds", "interacts" or "reacts", or "binding", or "interacting", or "reacting" are used where appropriate interchangeably with the terms "specifically bind", "specifically interact" or "specifically reacts". The interactions include hydrogen bonds, hydrophobic bonds, and ion bonds.

Within the context of this invention, the term "agent that binds" a determinant designates an agent that binds to said determinant with specificity and/or affinity. An antibody that binds said determinant designates an antibody that binds with specificity and/or affinity The term "reducing or blocking dimerization" should be understood as the process of interfering or preventing or diminishing the dimerization of KIR receptors at the surface of cells.

"Dimerization" of KIR as used herein comprises both heterodimerization, meaning dimerization between two different members of the KIR family, and homodimerization, meaning the formation of dimers of two identical KIR family members.

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

Within the context of this invention a "determinant" designates a site of interaction or binding that is shared by several gene products of the human KIR gene family.

The term "epitope" is defined as an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with an antibody or a receptor (such as, e.g., a T lymphocyte receptor). Epitopes can be linear or conformational/structural.

The term "linear epitope" is defined as an epitope composed of amino acid residues that are contiguous on the linear sequence of amino acids (primary structure).

The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used inter-changeably with 'structural'.

The term "antibody binding peptide" is defined as a peptide that binds with sufficiently high affinity to antibodies.

The term "immunogen" is a substance that is able to induce a humoral antibody and/or cell-mediated immune response rather than inducing immunological tolerance. The term 'immunogen' is sometimes used interchangeably with 'antigen', yet the term specifies the ability to stimulate an immune response as well as to react with the products of it, e.g. antibody. By contrast, 'antigen' is reserved by some to mean a substance that reacts with antibody. The principal immunogens are proteins and polysaccharides, free or attached to microorganisms.

The term "immunogenic" means a capacity to induce humoral antibody and/or cell-mediated immune responsiveness.

As used herein, a "Killer Ig-like Receptor" or "KIR", refers to a protein or polypeptide encoded by a gene that is a member of the KIR gene family or by a cDNA prepared from such a gene. A detailed review of the KIR gene family, including the nomenclature of KIR genes and KIR gene products, and Genbank accession numbers for exemplary KIRs, is provided in "The KIR Gene Cluster" by M. Carrington and P. Norman, available at the NCBI web-site called "Bookshelf" (accessible via the World-Wide Web (WWW) address ncbi.nlm.nih.gov/books). The sequences of human KIR genes and cDNAs, as well as their protein products, are available in public databases, including GenBank. Non-limiting exemplary GenBank entries of human genes belonging to the human KIR gene family have the following accession numbers: KIR2DL1: Genbank accession number U24076, NM_014218, AAR16197, or L41267; KIR2DL2: Genbank accession number U24075 or L76669; KIR2DL3: Genbank accession number U24074 or L41268; KIR2DL4: Genbank accession number X97229; KIR2DS1: Genbank accession number X89892; KIR2DS2: Genbank accession number L76667; KIR2DS3: Genbank accession number NM_012312 or L76670 (splice variant); KIR3DL1: Genbank accession number L41269; and KIR2DS4: Genbank accession number AAR26325.

A KIR may comprise from 1 to 3 extracellular domains, and may have a long (i.e., more than 40 amino acids) or short (i.e., less than 40 amino acids) cytoplasmic tail. As previously described herein, these features determine the nomenclature of a KIR. Exemplary KIR2DL1, KIR2DL2, and KIR2DL3 proteins comprise the following respective amino acid sequences, representing their extracellular domains:

KIR2DL1 extracellular domain:
(SEQ ID NO: 14)
HEGVHRKPSLLAHPGXLVKSEETVILQCWSDVMFEHFLLHREGMFNDTLR

LIGEHHDGVSKANFSISRMTQDLAGTYRCYGSVTHSPYQVSAPSDPLDIV

IIGLYEKPSLSAQXGPTVLAGENVTLSCSSRSSYDMYHLSREGEAHERRL

PAGPKVNGTFQADFPLGPATHGGTYRCFGSFHDSPYEWSKSSDPLLVSVT

GNPSNSWPSPTEPSSKTGNPRHLH, where "X" at position 16 is P or R, and where "X" at position 114 is P or L, representing allelic variants.

KIR2DL2 extracellular domain:
(SEQ ID NO: 15)
HEGVHRKPSLLAHPGRLVKSEETVILQCWSDVRFEHFLLHREGKFKDTLH

LIGEHHDGVSKANFSIGPMMQDLAGTYRCYGSVTHSPYQLSAPSDPLDIV

ITGLYEKPSLSAQPGPTVLAGESVTLSCSSRSSYDMYHLSREGEAHECRF

SAGPKVNGTFQADFPLGPATHGGTYRCFGSFRDSPYEWSNSSDPLLVSVI

GNPSNSWPSPTEPSSKTGNPRHLH

KIR2DL3 extracellular domain:
(SEQ ID NO: 16)
HEGVHRKPSLLAHPGPLVKSEETVILQCWSDVRFQHFLLHREGKFKDTLH

LIGEHHDGVSKANFSIGPMMQDLAGTYRCYGSVTHSPYQLSAPSDPLDIV

ITGLYEKPSLSAQPGPTVLAGESVTLSCSSRSSYDMYHLSREGEAHERRF

SAGPKVNGTFQADFPLGPATHGGTYRCFGSFRDSPYEWSNSSDPLLVSVT

GNPSNSWPSPTEPSSETGNPRHLH.

The term "KIR2DL" refers to a KIR molecule which is a KIR2DL1, KIR2DL2, KIR2DL3, or KIR2DL4 molecule.

The term "KIR2DL2/3" refers to either or both of the KIR2DL2 and KIR2DL3 receptors. These two receptors have a very high homology, they are allelic forms of the same gene, and are considered by the art to be functionally similar.

Unless otherwise specified, the term "MHC" encompasses MHC molecules in all mammals, whereas an "HLA" molecule refers to a human MHC molecule.

A "cross-reactive" KIR-binding agent is an agent that binds to more than one KIR molecule. For example, a "cross-reactive anti-KIR antibody" is an antibody that specifically binds more than one KIR molecule.

"Specific binding" or "specificity" refers to the ability of an antibody or other agent to detectably bind an epitope presented on an antigen while having relatively little detectable reactivity with other proteins or structures (such as other proteins presented on NK cells, or on other cell types). Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific antigen versus non-specific binding to other irrelevant molecules. A KIR-binding antibody specific for a human KIR can sometimes exhibit specific binding to similar KIRs of other species.

The phrase that a first antibody binds "substantially" or "at least partially" the same epitope as a second antibody means that the epitope binding site for the first antibody comprises at least 10%, 20%, 30%, 40%, 50%, 60%, 70%, 80%, 90%, or more of the amino acid residues on the antigen that constitutes the epitope binding site of the second antibody.

The ability of an anti-KIR antibody to "block" the binding of a KIR molecule to an HLA molecule means that the antibody, in an assay using soluble or cell-surface associated KIR and HLA molecules, can detectably reduce the binding of a KIR-molecule to an HLA molecule in a dose-dependent fashion, where the KIR molecule detectably binds to the HLA molecule in the absence of the antibody. Exemplary assays for determining whether an anti-KIR antibody is capable of such blocking are provided in the Examples.

The ability of an agent to "reduce KIR-mediated inhibition of NK cell cytotoxicity" or "potentiate NK cell cytotoxicity" means that an NK cell expressing a KIR, when contacted with the antibody, is more capable of lysing target cells that express on their surface a particular MHC or HLA class I (which is a ligand for said KIR) in the presence of the agent as compared to a control. The "reduction of inhibition" or "potentiation" means any detectable increase in NK cell cytotoxicity, including at least 5%, at least 10%, at least 20%, at least 40%, at least 70%, at least 100%, at least 500%, at least 1000%, or higher, or, for example, about 50-100%, about 100-500%, or about 100-2000% higher, or at least about 1.5-fold, at least about 2-fold, at least about 3-fold, at least about 5-fold, at least about 10, or at least about 20-fold higher, as compared to a control. This can be measured in an appropriate assay, e.g., a cytotoxicity assay where a higher number of target cells are lysed by NK cells in the presence of the agent than in the absence of the agent (i.e., the control). For example, the agent's ability to detectably increase specific lysis can be tested by, e.g., a classical chromium release test of cytotoxicity, compared with the level of specific lysis obtained without antibody when an NK cell population expressing a given KIR is put in contact with target cells expressing the cognate MHC class I molecule (recognized by the KIR expressed on NK cell). Alternatively, the term "reduce KIR mediated inhibition" means that in a chromium assay with an NK cell clone expressing one or several KIRs, and a target cell expressing only one HLA allotype recognized by one of the KIR of the NK clone and no other HLA class I molecule recognized by the other KIRs on the NK clone, the level of cytotoxicity obtained with the antibody should be at least 60% preferably at least 70%, or more of the cytotoxicity obtained with a control antibody that blocks the interactions between KIR and HLA-C, such as the anti-KIR mAbs GL183 or EB6 (available from Immunotech, France).

The term "treatment" is meant to include both the prevention and minimization of the referenced disease, disorder, or condition. Accordingly, "treatment" refers to both prophylactic and therapeutic administration of an agent or composition comprising an agent unless otherwise indicated or clearly contradicted by context. However, therapeutic administration of the agent or composition comprising the agent and prophylactic administration of the agent or composition comprising the agent can separately be considered unique aspects of the invention. For example, "treatment" of a patient in whom no symptoms or clinically relevant manifestations of a disease or disorder have been identified is preventive therapy.

The term "effective amount" refers to an amount which, when delivered in appropriate dosages and for appropriate periods of time, is sufficient to achieve a desired result, such as, e.g., detectably and/or substantially reduce inhibition of KIR-mediated NK cell cytotoxicity, or detectably and/or substantially reduce KIR dimerization. Depending on the intended use, an "effective amount" may also be a "therapeutically effective amount", "prophylactically effective amount", "physiologically effective amount", or a combination thereof. A "therapeutically effective amount" refers to an amount of an agent or composition effective, when delivered in appropriate dosages and for appropriate periods of time, to achieve a desired therapeutic result in a patient or other host (e.g., the inducement, promotion, and/or enhancement of a physiological response associated with reducing one or more aspects of the disorder, such as reducing cancer progression, reducing viral disease symptoms, increasing the likelihood of survival over a period of time (e.g., 18-60 months after initial treatment), reducing the spread of cancer cell-associated growths, and/or reducing the likelihood of recurrence of tumor growth). A therapeutically effective amount may vary according to factors such as the disease state, age, sex, and weight of the individual, and the ability of the composition to elicit a desired response in the individual. A therapeutically effective amount is also one in which any toxic or detrimental effects of the administered composition are outweighed by the therapeutically beneficial effects. A "prophylactically effective amount" refers to an amount effective, at dosages and for periods of time necessary, to achieve a desired prophylactic result (e.g., a reduction in the likelihood of developing a disorder, a reduction in the intensity or spread of a disorder, an increase in the likelihood of survival during an imminent disorder, a delay in the onset of a disease condition, a decrease in the spread of an imminent condition as compared to in similar patients not receiving the prophylactic regimen, etc.). Typically, because a prophylactic dose is used in subjects prior to or at an earlier stage of disease, the prophylactically effective amount will be less than the therapeutically effective amount. A "physiologically effective" amount refers to an amount that is sufficient to induce, promote, and/or enhance the desired physiological effect(s).

The term "substantially identical" in the context of two amino acid sequences means that the sequences, when optimally aligned, such as by the programs GAP or BESTFIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions (further described elsewhere herein). Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA, applying default or recommended parameters. A program in GCG Version 6.1, FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

An "isolated" agent typically refers to an agent that is not associated with significant amounts (e.g., more than about 1%, more than about 2%, more than about 3%, or more than about 5%) of extraneous and undesirable biological molecules (such as, e.g., non-KIR binding biological molecules, e.g., antibodies) contained within a cell, cell culture, chemical media, or animal in which the molecule in question is produced. An "isolated" agent can also refer to an agent that has passed through such a stage of purity due to human intervention (whether automatic, manual, or both) for a significant amount of time (e.g., at least about 10 minutes, at least about 20 minutes, at least an hour, or longer).

DESCRIPTION OF THE INVENTION

This invention is based, in part, on the discovery of antibodies capable of reducing KIR-mediated inhibition of NK cell cytotoxicity without blocking the binding of KIR to its HLA-ligand, and the finding that transduction of negative signaling via KIR, upon binding of KIR to its HLA class I ligand, involves a ligand-binding induced, conformational reorientation of the KIR molecule; allowing interactions to form between adjacent KIRs in specific domains, leading to accelerate clustering. Although it was previously known that ligand-binding leads to signaling via KIR, no mechanisms had been described that could fully explain how ligand-binding, occurring to the extracellular part of KIR on the outside of the cell, could be transmitted to the cytoplasmic tail of KIR and lead to intracellular signaling only when ligand is bound, but not when there is no ligand-binding. Also, while clustering of some types of receptors have been described in the literature, it is believed that, prior to the present invention, it was not known that dimerization or clustering of an NK cell inhibitory receptor such as KIR could be reduced or blocked by use of added agents. The discovery of sites on KIR that allow dimerization of KIR molecules can now provide at explanation for this, and allow the development and identification of therapeutic agents that would prevent inhibitory signaling via KIR, by targeting these and other sites not associated with HLA-binding.

As described in the examples, it has now been discovered that the initiation and propagation of inhibitory signaling via KIR requires that two or more KIR come into close proximity of one another, i.e., dimerize. Without being limited to theory, the process of dimerization is presumably initiated when KIR engages MHC class I ligands on target cells. This may bring KIR receptors into close proximity of one another, allowing the initiation of inhibitory signaling by mechanisms that involve phosphorylation of certain tyrosine residues in the cytoplasmic tail of KIRs. Although the precise events that allow ligand-binding to induce dimerization of KIR are not clear in molecular details, it has been reported that clustering of KIR (bringing several KIR molecules into proximity of one another) is sufficient to induce inhibitory signaling (Faure et al., supra). By interfering with this process of dimerization, or clustering, or bringing into proximity, it has now been found that one can prevent the initiation and propagation of inhibitory signaling. Previously, it has only been known that it was possible to reduce KIR-signaling by preventing KIR from binding to its MHC class I ligand. Described herein are novel agents that prevent initiation of inhibitory signaling without interfering with KIR's interactions with HLA class I, but instead modulate KIR signaling downstream of ligand-binding, by, e.g., preventing or reducing the dimerization and/or subsequent clustering of KIR. The advantage of these new agents, compared to those that block ligand binding, is that they do not prevent KIR-class I interactions from contributing to the adhesion of NK cells to target cells, thereby augmenting the positive activation of NK by target cells. A further advantage is that the epitopes of these mAbs, and the KIR dimerizations-sites, are more conserved among members of the KIR family, than are the ligand-binding domains, and hence, it may be easier to obtain mAbs that cross-react among various members of the KIR family. Antibodies that prevent negative signaling via multiple KIR are advantageous for therapeutic purposes because they induce lysis by larger proportions of NK cells.

As described in the Examples, one such agent identified is murine IgG1 mono-clonal antibody 1-26F117-A3. This antibody is cross-reactive, binding to at least KIR2DL1 and KIR2DL3; potentiates NK cell cytotoxicity; and does not reduce binding of KIR2DL1 to HLA-C. The amino acid sequences of the VH and VL regions of 1-26F117-A3 have been determined as follows:

```
VH region (SEQ ID NO: 17):
EVQLQQSGPELVKPGASVKISCKASDYSFTGYFMNWVMQSQEKSLEWIGR

INPFNGDAFYNQKFKGKATLTVDKSSNTAHMELRSLTSEDSAVYYCARLD

YRGYFFDYWGQGTTLTVSS

VL region (SEQ ID NO: 18):
DIVMTQSQKFMSTTVGDRVSITCKASQSVGSAVGWYQQKPGQSPKLLIYS

ASTRYTGVPDRFTGSGSGTDFTLTITNMQSDDLADYFCHQYSRYPLSFGS

GTKLEMKR.
```

The CDRs of the VH and VL regions of 1-26F117-A3 have been determined as follows:

```
CDR H1: GYFMN
(residues 31-35 of SEQ ID NO: 17)

CDR H2: RINPFNGDAFYNQKFKG
(residues 50-66 of SEQ ID NO: 17)

CDR H3: LDYRGYFFDY
(residues 99-108 of SEQ ID NO: 17).

CDR L1: KASQSVGSAVG
(residues 24-34 of SEQ ID NO: 18)

CDR L2: SASTRYT
```

-continued
(residues 50-56 of SEQ ID NO: 18)

CDR L3: HQYSRYPLS
(residues 89-97 of SEQ ID NO: 18).

The cDNA sequences of the VL and VH regions of 1-26F117-A3 have been determined as follows:

```
VH region (SEQ ID NO: 19):
gaggttcagctgcagcagtctggacctgagctggtgaagcctggggcttc agtgaagatatcctgtaaggcttctgattactcafttactggctacttta tgaactgggtgatgcagagccaagaaaagagccttgagtggattggacgt attaatcctttcaatggtgatgctttctacaaccagaagttcaagggcaa ggccacattgactgtggacaaatcctctaacacagcccacatggagctcc ggagcctgacatctgaggactctgcagtctattattgtgcaagattggat taccgcggctacttcfttgactactggggccaaggcaccacgctcacagt ctcatca.

VL region (SEQ ID NO: 20):
gacattgtgatgacccagtctcaaaaattcatgtccacaacagtaggaga cagggtcagcatcacctgcaaggccagtcagagtgtgggtagcgctgtag gctggtatcaacagaaaccaggacaatctcctaaactactgatttactca gcatccactcggtacactggagtccctgatcgcttcacaggcagtggatc tgggacagatttcactctcaccattaccaatatgcagtctgatgacctgg cagattatttctgtcaccaatatagcagatatcctctctcgttcggctcg gggacaaagttggaaatgaaacgg.
```

Another such agent identified is murine IgG1 monoclonal antibody 1-26F117-A4. As described in the Examples, this antibody potentiates NK cell cytotoxicity; and does not reduce binding of KIR2DL1 to HLA-C. The amino acid sequences of the VH and VL regions of 1-26F117-A4 have been determined as follows:

```
VH region (SEQ ID NO: 21):
QVQLKESGPGLVAPSQSLSITCTVSGFSLTDYGVSWVRQPPGKGLEWLGL

IWGDGRTNYHSALISRLSISKDNSKSQVFLKLNSLQIDDTATYYCARRGA

MDYWGQGTSVTVSS
```

The VL sequence was identical to the VL sequence of 1-26F117-A3; (SEQ ID NO:18).

The CDRs of the VH and VL regions of 1-26F117-A4 have been determined as follows:

```
CDR H1: DYGVS
(residues 31-35 of SEQ ID NO: 21)

CDR H2: LIWGDGRTNYHSALISR
(residues 50-66 of SEQ ID NO: 21)

CDR H3: RGAMDY
(residues 98-103 of SEQ ID NO: 21)

CDR L1: KASQSVGSAVG
(residues 24-34 of SEQ ID NO: 18)

CDR L2: SASTRYT
(residues 50-56 of SEQ ID NO: 18)
```

CDR L3: HQYSRYPLS
(residues 89-97 of SEQ ID NO: 18).

The cDNA sequences of the VL and VH regions of 1-26F117 have been determined as follows:

VH region (SEQ ID NO: 22):
caggtgcagctgaaggagtcaggacctggcctggtggcgccctcacagag cctgtccatcacatgcactgtctcagggttctcactaaccgactatggtg taagctgggttcgccagcctccaggaaagggtctggagtggctgggacta atatggggtgacgggcgcacaaattatcattcagctctcatatccagact gagcatcagcaaggataactccaagagccaagttttcttaaaactgaaca gtctgcaaattgatgacacagccacatactactgtgccagaaggggtgct atggactactggggtcaaggaacctcggtcaccgtctcctca.

VL region (SEQ ID NO: 23):
gacattgtgatgacccagtctcaaaaattcatgtccacaacagtaggaga cagggtcagcatcacctgcaaggccagtcagagtgtgggtagcgctgtag gctggtatcaacagaaaccaggacaatctcctaaactactgatttactca gcatccactcggtacactggagtccctgatcgcttcacaggcagtggatc tgggacagatttcactctcaccattaccaatatgcagtctgatgacctgg ctgattatttctgtcaccaatatagcagatatcctctctcgttcggctcg gggacaaagttggaaatgaaacgg.

Accordingly, in one aspect, the invention relates to KIR-binding agents, including small molecules, polypeptides, and antibodies (including antibody fragments or derivatives) which are capable of reducing KIR-mediated inhibition of NK cell cytotoxicity without interfering with KIR-binding to HLA, as well as to pharmaceutical compositions comprising such agents, alone or in combination with other active agents. In one embodiment, the agent is a cross-reactive anti-KIR antibody, binding, e.g., to KIR2DL1 and KIR2DL2 and/or KIR2DL3. In another embodiment, the agent is an antibody capable reducing KIR2DL-mediated inhibition of NK cell cytotoxicity.

In another aspect, the invention relates to methods of using such agents, including antibodies, to enhance KIR-mediated NK cell cytotoxicity, to enhance NK cell-mediated killing of target cells, and to treat cancer or viral diseases. In one embodiment, the method is a method of enhancing KIR2DL-mediated, or KIR2DL1- and KIR2DL2/3-mediated, NK cell cytotoxicity. In another embodiment, the method is a method of enhancing cytotoxicity by NK cells expressing KIR2DL1-receptors, or KIR2DL2/3 receptors, or populations of NK cells expressing either or both KIR2DL1- and KIR2DL2/3, such as in human individuals.

In another aspect, the invention relates to methods of producing and/or identifying such agents, including antibodies, by producing and screening a library of anti-KIR binding antibodies or other agents, and selecting those that (a) KIR-mediated inhibition of NK cell cytotoxicity, and (b) do not reduce KIR-binding to HLA, where steps (a) and (b) can optionally be reversed. In one embodiment, step (a) comprises selecting agents that reduce KIR2DL-mediated-, or KIR2DL1- and KIR2DL2/3-mediated inhibition of NK cell cytotoxicity. Suitable assays for carrying out such methods are described herein, particularly in the Examples. In one aspect of the invention, the same or similar methods are used to prepare and identify hybridomas producing antibodies of the invention.

In another aspect, the invention relates to antibodies or other agents which compete with 1-26F117-A3 and/or 1-26F117-A4 in binding to at least one of KIR2DL1 and KIR2DL3.

In another aspect, the invention relates to antibodies or other agents which compete with an antibody comprising VH and VL sequences consisting essentially of the VH and VL sequences of 1-26F117-A3 or 1-26F117-A4 in binding to at least one of KIR2DL1 and KIR2DL3.

In exemplary embodiments, the agent is an antibody such as a full-length murine, human, humanized, or chimeric antibody; or a fragment or derivative thereof. In one embodiment, the antibody binds the same epitope as 1-26F117. In another embodiment, the antibody binds substantially the same epitope as 1-26F117. In another embodiment, the agent is a monoclonal antibody that binds an epitope on KIR2DL1 and/or KIR2DL3 that is recognized by monoclonal antibody 1-26F117-A3 and/or 1-26F117-A4, or by a monoclonal antibody comprising a VH sequence of SEQ ID NO:17 and a VL sequence of SEQ ID NO:18, or by a monoclonal antibody comprising a VH sequence of SEQ ID NO:21 and a VL sequence of SEQ ID NO:18. In another embodiment, the antibody, including a fragment or derivative thereof, comprises the same or substantially identical VH and/or VL regions as 1-26F117-A3 or 1-26F117-A4. In another embodiment, the antibody, including a fragment or derivative thereof, comprises a VH region that has at least 95%, at least 98%, or at least 99% sequence identity to SEQ ID NO:17 or SEQ ID NO:21. In another embodiment, the antibody, including a fragment or derivative thereof, comprises a VL region that has at least 95%, at least 98%, or at least 99% sequence identity to SEQ ID NO:18. In another embodiment, the antibody, including a fragment or derivative thereof, comprises the same or substantially identical CDR H1, H2, H3, L1, L2, and L3 regions as 1-26F117-A3 or 1-26F117-A4. In a particular embodiment, the antibody comprises a VH sequence of SEQ ID NO:17, a VL sequence of SEQ ID NO:18, as well as the sequence for murine IgG1 constant heavy chain region (GenBank accession No. D78344, hereby specifically incorporated by reference in its entirety) and the sequence for murine IgG1 constant light chain region (GenBank accession No. V00807, hereby specifically incorporated by reference in its entirety). In another embodiment, the antibody comprises VH and VL sequences consisting essentially of the VH and VL sequences of SEQ ID NO:17 and SEQ ID NO:18, respectively. In another particular embodiment, the antibody comprises a VH sequence of SEQ ID NO:21, a VL sequence of SEQ ID NO:18, as well as the sequence for murine IgG1 constant heavy chain region (GenBank accession No. D78344, hereby specifically incorporated by reference in its entirety) and the sequence for murine IgG1 constant light chain region (GenBank accession No. V00807, hereby specifically incorporated by reference in its entirety). In another embodiment, the antibody comprises VH and VL sequences consisting essentially of the VH and VL sequences of SEQ ID NO:21 and SEQ ID NO: 18, respectively. In another embodiment, the antibody is an isolated antibody. Methods of preparing and identifying such antibodies are described herein. The invention also relates to nucleotide sequences encoding such antibodies, expression vectors comprising such sequences, host cells comprising such vectors, and methods of producing such antibodies from such host cells.

In another aspect the invention relates to an agent that binds or interacts with a determinant present on a human KIR gene product, wherein said agent is capable of reducing KIR-mediated inhibition of NK cell cytotoxicity by reducing or blocking dimerization of KIR.

In another aspect the present invention relates to a method of reducing KIRmediated inhibition of NK cell cytotoxicity by reducing or blocking dimerization of KIR.

In another aspect the present invention relates to the agent according to the invention for use as a medicament.

In another aspect the present invention relates to a use of the agent according to the invention, for the preparation of a medicament for treatment of cancer, infectious disease, viral infections, or immune disorders.

In another aspect the present invention relates to a hybridoma comprising a B-cell from a non-human mammalian host that has been immunized with an antigen that comprises a determinant present on a human KIR polypeptide, fused to an immortalized cell, wherein said hybridoma produces a monoclonal antibody that binds a determinant present on a human KIR polypeptide, and wherein said antibody is capable of neutralizing KIR-mediated inhibition of NK cell cytotoxicity on a population of NK cells expressing said human KIR polypeptide product by reducing or blocking dimerization of KIR.

In another aspect the present invention relates to a method of isolating an agent capable of neutralizing KIR mediated inhibition of NK cell cytotoxicity by:

a) providing the agent; and b) testing dimerization of KIR in the presence of the agent under conditions conducive for dimerization (such as the presence of target cells expressing HLA-C or other KIR-ligands);

c) selecting the agent from (b) that are capable of neutralizing KIR-mediated inhibition of NK cell cytotoxicity, wherein the order of steps (c) and (d) is optionally reversed.

In another aspect the present invention relates to a method for producing an anti-body or an antibody fragment that binds a determinant on a human KIR receptor gene product, wherein said antibody is capable of reducing KIR-mediated inhibition of NK cell cytotoxicity, comprising the steps of:

a) immunizing a non-human animal with an immunogen comprising a KIR polypeptide;

b) preparing antibodies from said immunized animal, wherein said antibodies bind said KIR polypeptide;

c) selecting antibodies that block dimerization of KIR;

d) selecting antibodies from (c) that are capable of neutralizing KIR-mediated inhibition of NK cell cytotoxicity, wherein the order of steps (c) and (d) is optionally reversed.

In another aspect the present invention relates to a pharmaceutical composition comprising an agent according to the invention, and one or more pharmaceutically acceptable carriers or diluents.

In a particular embodiment the agent is a monoclonal antibody, or a derivative or fragment thereof.

In a particular embodiment, the agents of this invention are agents, such as monoclonal antibodies, or small molecules, or peptides, or proteins, which bind to one of the determinants on KIR, thereby preventing or reducing inhibitory signaling.

In a particular embodiment the KIR gene product is an inhibitory KIR gene product. Some KIR gene products are inhibitory in nature. All confirmed inhibitory KIRs have a long cytoplasmic tail, and display in their intracytoplasmic portion one or several amino acid motifs that recruit phosphatases responsible for inhibitory signaling. Distinct KIR interact with different subsets of HLA class I antigens. The known inhibitory KIR receptors include members of the KIR2DL and KIR3DL subfamilies.

In a particular embodiment the determinant is an epitope, and more particularly a conformational epitope.

In a particular embodiment the agent is an antibody.
Reducing Inhibitory KIR Signalling The antibodies of this invention are able to neutralize the KIR-mediated inhibition of NK cell cytotoxicity; particularly inhibition mediated by KIR2DL receptors and more particularly at least both the KIR2DL1 and KIR2DL2/3 inhibition. These antibodies thus "reduce" or "block" dimerization in the sense that they block, at least partially, the inhibitory signaling pathway mediated by KIR receptors. More importantly, this inhibitory activity is displayed with respect to several types of inhibitory KIR receptors, particularly several KIR2DL receptor gene products, and more particularly at least KIR2DL1, KIR2DL2, and KIR2DL3 so that these antibodies may be used in various subjects with high efficacy. Inhibition of KIRmediated inhibition of NK cell cytotoxicity can be assessed by various assays or tests, such as binding or cellular assays. An exemplary method for testing whether a mAb meets the criteria of the present invention, i.e., has (1) the ability to reduce KIR-mediated inhibitory signaling, (2) without blocking KIR-HLA class I interactions, is as follows (see also the Examples):

(1) The ability of an agent to reduce KIR-mediated signalling can be tested in a standard 4-hour in vitro cytotoxicity assay using NK cells that express KIR2DL1, and target cells that express HLA-Cw4. Such NK cells do not kill targets that express HLA-Cw4 because KIR2DL1 recognizes HLA-Cw4, leading to dimerization of KIR, which in turn leads to initiation and propagation of inhibitory signalling that prevents NK-mediated cytolysis. The in vitro cytotoxicity assay is carried out by standard methods that are well known in the art, as described for example in Coligan et al., eds., Current Protocols in Immunology, Greene Publishing Assoc. and Wiley Interscience, N.Y., (1992, 1993). The target cells are labeled with $^{51}$Cr prior to addition of NK cells, and then the killing is estimated as proportional to the release of $^{51}$Cr from the cells to the medium, as a result of killing. Addition of an agent that pre-vents dimerization of KIR, or agents that prevent KIR from binding to HLA-Cw4, results in prevention of the initiation and propagation of inhibitory signalling via KIR. Therefore addition of such agents results in increases in NK-mediated killing of the target cells. Thus, this step identifies agents that prevent KIR-induced negative signalling by, e.g., blocking ligand binding or preventing dimerization of KIR, or other molecular events involved in transducing the signal from outside the cell to inside the cell, indicating the KIR has bound a ligand. In a particular $^{51}$Cr-release cytotoxicity assay, KIR2DL1-expressing YTS effector-cells (YTS-2DL1) can kill LCL 721.221-Cw3 target cells, but not LCL 721.221-Cw4 cells. In contrast, YTS effector-cells that lack KIRs (YTS) kill both cell-lines efficiently. Thus, YTS-2DL1 effector cells cannot kill LCL 721.221-Cw4 cells due to HLA-Cw4-induced inhibitory signalling via KIR2DL1. When YTS-2DL1 cells are pre-incubated with blocking anti-KIR mAbs or mAbs according to the present invention in such a $^{51}$Cr-release cytotoxicity assay, LCL 721.221-Cw4 cells are killed in an anti-KIR mAb-concentration-dependent fashion.

(2) To determine whether an agent block KIR interactions with HLA class I, the following test is performed: The cell line 721.221 transfected with HLA-Cw4 (Litwin et al. Journal of Experimental Medicine. 1993. Vol 178, pages 1321-1336) is incubated with 10 ug/ml of a soluble KIR2DL1-Fc fusion protein (produced and purified as described in Wagtmann et al. Immunity. 1995. Vol 3, pages 801-809), for 30 min at 4° C., in the presence or absence of increasing concentrations of a test anti-KIR mAb. The cells are washed, and then incubated with a secondary antibody that recognizes the Fc part of the KIR-Fc fusion protein, washed again, and analyzed on a flow cytometer (FACScalibur, Beckton Dickinson), by standard methods. In the absence of anti-KIR mAbs, the KIR-Fc protein binds well to 721.221-Cw4 cells. In the presence of an anti-KIR mAb that blocks KIR binding to HLA-C, there is a reduced binding of KIR-Fc to the cells, and such mAbs are designated "blocking mAbs". If the anti-KIR mAb does not lead to a reduction in binding of the KIR-Fc protein to cells, then the anti-KIR mAb is designated a "non-blocking" mAb.

If an anti-KIR mAb induces killing of target cells expressing HLA-C by NK cells expressing KIR (by experiment no 1 above) and it does not block binding of KIR to HLA-C (in experiment 2 above), then the mAb is an antibody of the invention, preventing inhibitory KIR signalling by, e.g., reducing dimerization, without preventing KIR from binding to HLA-C.

The antibodies of this invention may reduce, e.g., partially or fully neutralize, the KIR-mediated inhibition of NK cell cytotoxicity. For example, preferred antibodies of this invention are able to induce the lysis of matched or HLA compatible or autologous target cell population, i.e., cell population that would not be effectively lysed by NK cells in the absence of said antibody. Accordingly, the antibodies of this invention may also be defined as facilitating, potentiating, or promoting NK cell cytotoxic activity, both in vitro and in vivo.

Upon immunization and production of antibodies, particular selection steps may be performed to isolate antibodies of the invention. Once identified as monoclonal antibodies capable of binding to KIR polypeptides, the antibodies are selected for their capability to reduce KIR-mediated inhibition of NK cell cytotoxicity without reducing HLA-binding, and/or their capability to block dimerization of KIR. This selection can be performed as described herein.

In a specific aspect, the invention also relates to methods of producing an antibody or an antibody fragment that binds a determinant on a human KIR receptor gene product, wherein said antibody is capable of reducing KIR-mediated inhibition of NK cell cytotoxicity, comprising the steps of:

(a) immunizing a non-human mammal with an immunogen comprising a KIR polypeptide;

(b) preparing antibodies from said immunized animal, wherein said antibodies bind said KIR polypeptide, (c) selecting antibodies of (b) that are capable of reducing KIR-mediated inhibition of NK cell cytotoxicity, and (d) selecting antibodies of (c) that do not reduce KIR-binding to HLA-C, wherein the order of steps (c) and (d) optionally can be reversed.

In one embodiment, the antibodies prepared in step (b) are monoclonal antibodies. Thus, the term "preparing antibodies from said immunized animal," as used herein, includes obtaining B-cells from an immunized animal and using those B cells to produce a hybridoma that expresses antibodies, as well as obtaining antibodies directly from the serum of an immunized animal. In another embodiment, the antibodies selected in step (c) cause at least a 10% augmentation or reduction of inhibition in NK cytotoxicity mediated by NK cells displaying at least one KIR recognized by the antibody, preferably at least a 40 or 50%, or more preferably at least a 70% augmentation in NK cytotoxicity, as measured in a standard chromium release assay towards a target cell expressing cognate HLA class I molecule.

According to another embodiment, the invention provides a hybridoma comprising a B cell from a non-human host, wherein said B cell produces an antibody that binds a determinant present on a human KIR receptor gene product, e.g. a human inhibitory KIR receptor gene product, and is capable of reducing the inhibitory activity of said receptors. The hybridoma according to this invention is created as described herein by the fusion of splenocytes from the immunized non-human mammal with an immortal cell line. Hybridomas produced by this fusion are screened for the presence of such an antibody. Particularly, the hybridoma produces an antibody that does not block KIR-binding to HLA-C, and/or recognizes a determinant present on domain 1 or domain 2 or homologous domains as described above, and cause potentiation of NK cell cytotoxicity.

In separate aspects, the agents of the invention compete with 1-26F117-A3 and/or 1-26F117-A4 and/or other antibodies or the invention in binding to KIR2DL1 or KIR2DL3, and/or bind the same or substantially the same KIR2DL1 and/or KIR2DL3 epitope. Such agents can be identified using various methods known in the art. For example, the identification of one or more antibodies that competes with an antibody of the invention such as, e.g., 1-26F117-A3 and/or 1-26F117-A4, can be determined using known screening assays in which antibody competition can be assessed. A number of such assays are routinely practiced and well known in the art (see, e.g., U.S. Pat. No. 5,660,827, which is specifically incorporated herein by reference). For example, where the test antibodies to be examined are obtained from different source animals, or are even of a different Ig isotype, a simple competition assay may be employed in which the control antibody (1-26F117-A3 or 1-26F117-A4, for example) is mixed with the test antibody and then applied to a sample containing either or both KIR2DL1 and/or KIR2DL3. Protocols based on, e.g., ELISAs, radioimmunoassays, Western blotting, and the use of BIACORE analysis are suitable for use in such simple competition studies.

In certain embodiments, one would pre-mix the control antibody with varying amounts of the test antibody (e.g., in ratios of about 1:1, 1:2, 1:10 or about 1:100) for a period of time prior to applying to the KIR antigen sample. Alternatively, the control and varying amounts of test antibody can simply be added separately and admixed during exposure to the KIR antigen sample. As long as one can distinguish bound from free antibodies (e.g., by using separation or washing techniques to eliminate un-bound antibodies) and control antibody from the test antibody (e.g., by using species specific or isotype specific secondary antibodies or by specifically labelling the control antibody with a detectable label) one will be able to determine if the test antibody reduce the binding of the control antibody to the different KIR2DL antigens, indicating that the test antibody recognizes substantially the same epitope as the control. The binding of the (labeled) control antibody in the presence of a completely irrelevant antibody (that does not bind KIR) can serve as the control high value. The control low value can be obtained by incubating the labeled control antibody with the same but unlabelled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of a 1-26F117 control antibody to one or both of KIR2DL1 and KIR2DL3 antigens by at least about 50%, such as at least about 60%, or more preferably at least about 70% (e.g., about 65-100%), at any ratio of 1-26F117 to test antibody between about 1:1 or 1:10 and about 1:100 is considered to be an antibody that competes with the 1-26F117 control antibody.

Competition can also be assessed by, for example, flow cytometry. In such a test, cells bearing a given KIR can be incubated first with a control antibody (1-26F117-A3 or 1-26F117-A4, for example), and then with the test antibody labeled with a fluorochrome or biotin. The antibody is said to compete with control antibody if the binding obtained upon pre-incubation with saturating amount of control antibody is about 80%, preferably about 50%, about 40% or less (e.g., about 30%) of the binding (as measured by mean of fluorescence) obtained by the test antibody without preincubation with control antibody. Alternatively, an antibody is said to compete with the control antibody if the binding obtained with a labeled control antibody (by a fluorochrome or biotin) on cells preincubated with saturating amount of test antibody is about 80%, preferably about 50%, about 40%, or less (e.g., about 30%) of the binding obtained without preincubation with the test antibody.

A simple competition assay in which a test antibody is pre-adsorbed and applied at saturating concentration to a surface onto which either KIR2DL1 or KIR2DL2/3, or both, are immobilized also may be advantageously employed. The surface in the simple competition assay is preferably a BIACORE chip (or other media suitable for surface plasmon resonance analysis). The binding of a control antibody (e.g., 1-26F117-A3 or 1-26F117-A4) to the KIR-coated surface is measured. This binding to the KIR-containing surface of the control antibody alone is compared with the binding of the control antibody in the presence of a test antibody. A significant reduction in binding to the KIR2DL1 and KIR2DL2/3-containing surface by the control antibody in the presence of a test antibody indicates that the test antibody recognizes substantially the same epitope as the control antibody such that the test antibody "competes" with the control antibody. Any test antibody that reduces the binding of control antibody to both of KIR2DL1 and KIR2DL2/3 antigens by at least about 20% or more, at least about 40%, at least about 50%, at least about 70%, or more, can be considered to be an antibody that competes with the control antibody. Preferably, such test antibody will reduce the binding of the control antibody to each of at least the KIR2DL1, 2, and 3 antigens by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for KIR2DL1 and KIR2DL2/3 antigens is bound to the KIR2DL1 and KIR2DL2/3-containing surface first, as it will be expected that the decrease in binding seen for the second antibody (assuming the antibodies are competing) will be of greater magnitude. Further examples of such assays are provided in the Examples herein, and in e.g., Saunal and Regenmortel, (1995) J. Immunol. Methods 183: 33-41, the disclosure of which is incorporated herein by reference.

Determination of whether an antibody or other agent binds to the same or substantially the same epitope region as an antibody of the invention, e.g., 1-26F117-A3 or 1-26F11.7-A4, can be carried out using methods known to the person skilled in the art. In an example of epitope mapping/characterization methods, an epitope region for an anti-KIR antibody may be determined by epitope "foot-printing" using chemical modification of the exposed amines/carboxyls in the KIR2DL 1 or KIR2DL2/3 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an anti-body, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering Res Found Workshop. 2004; (44):149-67; Huang et al, Journal of Molecular Biology, Vol. 281 (1) pp. 61-67 (1998); and Saito and Patterson, Methods. 1996 June; 9(3):516-24.

Epitope mapping/characterization also can be performed using mass spectrometry methods. See, e.g., Downward, J Mass Spectrom. 2000 April; 35(4):493-503 and Kiselar and Downard, Anal Chem. 1999 May 1; 71 (9):1792-801.

Protease digestion techniques also can be useful in the context of epitope mapping and identification. Antigenic determinant-relevant regions/sequences can be determined by protease digestion, e.g. by using trypsin in a ratio of about 1:50 to KIR2DL1 or KIR2DL2/3 o/n digestion at 37° C. and pH 7-8, followed by mass spectrometry (MS) analysis for peptide identification. The peptides protected from trypsin cleavage by the anti-KIR antibody can subsequently be identified by comparison of samples subjected to trypsin digestion and samples incubated with antibody and then subjected to digestion by e.g. trypsin (thereby revealing a foot print for the antibody). Other enzymes like chymotrypsin, pepsin, etc., also or alternatively can be used in a similar epitope characterization methods. Moreover, enzymatic digestion can provide a quick method for analyzing whether a potential antigenic determinant sequence is within a region of the KIR2DL1 in the context of a KIR-binding agent. If the polypeptide is not surface exposed, it is most likely not relevant in terms of immunogenicity/antigenicity. See, e.g., Manca, Ann Ist Super Sanita. 1991; 27(1):15-9 for a discussion of similar techniques.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant resuction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "foot-printing". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kröger et al., Biosensors and Bioelectronics 2002; 17:937-944.

It should also be noted that an antibody binding the same or substantially the same epitope as an antibody of the invention can be identified in one or more of the exemplary competition assays described herein.

Prevention of KIR Dimerization

According to the present invention, one way to prevent inhibition of NK cell cytotoxicity without interfering with KIR-binding to HLA-C is to prevent KIR dimerization. In one aspect, another way to prevent inhibition of NK cell cytotoxicity without interfering with KIR-binding to HLA-C is to prevent KIR clustering.

As described in Example 1, using different molecular modeling approaches, including "the conserved site approach", "protein-protein docking approach" and "crystal packing approach", all described below, it was discovered that there are sites on KIR which permit two KIRs to interact with one another. One such site, defined herein as an "interaction site associated with Domain 1", is located in Domain 1 of KIR, corresponding to residues 1-101 of the extracellular portion of KIR2DL1 (SEQ ID NO:14). This site comprises a number of adjacent amino acid residues in the folded polypeptide. The amino acids that make up this site can be bound by an agent of the present invention. The amino acids in an interaction site in one KIR molecule can interact with amino acids in the identical site in an adjacent KIR. Therefore, KIR-KIR dimerization involves interactions between amino acids in "interaction site associated with Domain 1" in one KIR and amino acids in "interaction site associated with Domain 1" in another KIR. This other KIR can be of the same type, such as KIR2DL1-KIR2DL1 interactions. However, since the "interaction site associated with Domain 1" is conserved in most or all other KIR, the interactions can also be between different KIR, such as KIR2DL1-KIR2DL2, or KIR2DL1-KIR2DS3, or other interactions.

In addition to an interaction site in Domain 1 of KIR, a distinct interaction site in Domain 2 was also identified, which was termed "interaction site associated with Domain 2". Domain 2 of KIR corresponds to residues 105-200 of the extracellular portion of KIR2DL1 (SEQ ID NO:14). Two KIRs may dimerize by interactions between amino acids in "interaction site associated with Domain 2" in one KIR and amino acids in "interaction site associated with Domain 2" of another KIR. The amino acids within an "interaction site associated with Domain 2" are conserved in most or all other KIR; therefore dimerization may be between two KIR of the same type (such as KIR2DL2-KIR2DL2, or KIR2DL3-KIR2DL3) or between different types of KIR (such as KIR2DL1-KIR2DL2, or KIR2DL1-KIR2DS4).

The invention thus provides agents and related methods for preventing KIR dimerization, where an agent will bind a KIR determinant within an interaction sites associated with Domain 1 or 2 and thereby inhibit or reduce dimerization of KIR by interfering with the interaction between the amino acids comprised in the interaction site associated with Domain 1 or 2. The determinant can be comprised in the said interaction site associated with Domain 1 or 2, however, the determinant could also be adjacent to the interaction site and still affect the dimerization. In one embodiment the determinant is an epitope, particularly a structural epitope.

Particularly, the determinant can be shared by at least two members of the KIR2DL receptor group. More particularly, the determinant can be shared by at least KIR2DL1 and KIR2DL2 and -3. Certain antibodies of this invention may, in addition to recognizing multiple gene products of KIR2DL, also recognize determinants present on other inhibitory KIRs, such as gene products of the KIR3DL receptor group. Furthermore, antibodies of this invention may crossreact with activating KIRs, including but not limited to KIR2DS1, or KIR2DS2 or KIR2DS3. The determinant or epitope may represent a peptide fragment or a conformational epitope shared by said members of the KIR family.

Interaction sites according to the invention associated with either Domain 1 or Domain 2 of KIR are present in the folded polypeptide as adjacent amino acid residues and are thus a conformational interaction site. The specific residues and their positions are given in the examples and reproduced below. In one embodiment of the invention the said determinant is a conformational epitope adjacent to or comprised in the interaction site associated with Domain 1 or 2.

According to the above, in one aspect of the invention, dimerization of KIR is reduced or blocked by inhibition of interaction between two interaction sites associated with Domain 1.

In another aspect, dimerization of KIR is reduced or blocked by inhibition of interaction between two interaction sites associated with Domain 2.

In another aspect, the invention provides methods of producing an antibody or an antibody fragment that binds a determinant on a human KIR receptor gene product, wherein said antibody is capable of reducing KIR-mediated inhibition of NK cell cytotoxicity, comprising the steps of:

(a) immunizing a non-human mammal with an immunogen comprising a KIR polypeptide;

(b) preparing antibodies from said immunized animal, wherein said antibodies bind said KIR polypeptide, (c) selecting antibodies of (b) that block dimerization of KIR gene products, and (d) selecting antibodies of (c) that are capable of reducing KIR-mediated inhibition of NK cell cytotoxicity, wherein the order of steps (c) and (d) optionally can be reversed.

In one embodiment, the antibodies prepared in step (b) are monoclonal antibodies. Thus, the term "preparing antibodies from said immunized animal," as used herein, includes obtaining B-cells from an immunized animal and using those B cells to produce a hybridoma that expresses antibodies, as well as obtaining antibodies directly from the serum of an immunized animal. In another embodiment, the antibodies selected in step (c) are those that bind to a determinant according to the invention, more particularly those that bind to the interaction sites associated with Domain 1 or Domain 2 of the invention, and block dimerization of KIR. In yet another embodiment, the antibodies selected in step (d) cause at least a 10% augmentation or reduction of inhibition in NK cytotoxicity mediated by NK cells displaying at least one KIR recognized by the antibody, preferably at least a 40 or 50%, or more preferably at least a 70% augmentation in NK cytotoxicity, as measured in a standard chromium release assay towards a target cell expressing cognate HLA class I molecule.

According to another embodiment, the invention provides a hybridoma comprising a B cell from a non-human host, wherein said B cell produces an antibody that binds a determinant present on a human KIR receptor gene product, e.g. a human inhibitory KIR receptor gene product, and is capable of reducing the inhibitory activity of said receptors. The hybridoma according to this invention is created as described herein by the fusion of splenocytes from the immunized non-human mammal with an immortal cell line. Hybridomas produced by this fusion are screened for the presence of such an antibody. Particularly, the hybridoma produces an antibody that recognizes a determinant present on Domain 1 or Domain 2 or homologous domains as described above, and cause potentiation of NK cells by reducing or blocking dimerization of KIR.

Methods known in the art can be used to test whether an agent reduces KIRmediated inhibition by blocking KIR dimerization or clustering, with simple modification. For example, the Fluorescence Resonance Energy Transfer (FRET)-based method described by Faure et al. (J. Immunol. 2003; 170:6107-14) can be adapted to the following assay to detect whether an agent of the invention reduces or blocks KIR dimerization and/or clustering. In this assay, the NK cell line YTS-2DL1, which expressed KIR2DL1, is incubated with target cells expressing recombinant HLA-Cw4 molecules, that are ligands of KIR2DL1. The transfected HLA-Cw4 molecules contain at their C-terminus a Green Fluorescent Protein (GFP) or a Yellow Fluorescent Protein (YFP), that emit green or yellow light, respectively, when excited with a 454-nm laser. Cells co-transfected with both the Cw4-GFP and Cw4-YFP constructs are mixed with YTS-2DL1 NK cells, incubated for 20 min at 37° C., and cell conjugates fixed. FRET analysis is then performed by exiting at 454-nm, and simultaneously recording spectral fluorescent images on a confocal laser scanning microscope. By photobleaching the YFP signal, one can obtain a measure of fluorescence from the GFP protein, which will emit light at different wavelengths depending on its proximity to YFP, i.e., when fluorescence is transferred from YFP to GFP (FRET signal). When HLA-Cw4 molecules are evenly distributed on the surface of transfected cells in the resting state, very few HLA-Cw4 molecules come into such close proximity (less than 100 Å) as is required for generating a FRET signal, where fluorescence is transferred from YFP to GFP. However, in the presence of YTS-2DL1 cells, HLA-Cw4 molecules come into close proximity as detectable by fluorescence transfer from YFP to GFP (Faure et al. J. Immunol. 2003; 170:6107-14). Since the stoichiometry of KIR-HLA class I binding is 1:1 (Fan et al. Proc. Natl. Acad. Sci. USA. 1996; 93:7178), close proximity, or clustering, or dimerization of HLA-Cw4, as revealed by FRET, implies similarly close proximity of KIR. By performing this assay in the presence or absence of anti-KIR mAbs, a measure is obtained of the ability of anti-KIR mAbs to influence KIR clustering or dimerization. An anti-KIR mAb that reduces FRET by HLA-Cw4-GFP to the level observed when target cells are incubated in the absence of NK cells is indicative of an mAb that pre-vents KIR clustering or dimerization.

In an alternative configuration of the same type of assay, target cells are used that express wild-type HLA-Cw4, or another HLA-C ligand of a certain KIR, which is expressed recombinantly, with GFP or YFP tags at the C-terminus, in YTS cells. Engagement of GFP and YFP-labelled KIR by HLA-C results in clustering or dimerization that lead to a FRET signal. Addition of anti-KIR mAbs that prevent clustering or dimerization of KIR will lead to reduced FRET signaling.

In an alternative assay, whether a particular anti-KIR binding agent, such as an antibody, prevents KIR dimerization is determined by testing whether the agent binds to Domains 1 or 2 of KIR. An agent identified to bind to either Domain 1 or 2 should reduce or block KIR dimerization. An exemplary assay for testing binding of an agent to Domain 1 or 2 is provided in Example 8.

Figure 1B:
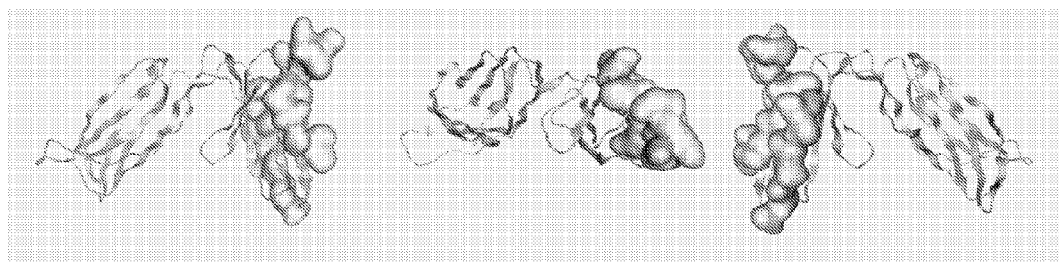
FIG. 1B illustrates the location of the interaction site associated with Domain 2 on the structure of KIR2DL1 (1 NKR.pdb) with views from the front (D1 left, D2 right), top (D1 left D2 right) and back (D2 left, D1 right) respectively.
Figure 1C:
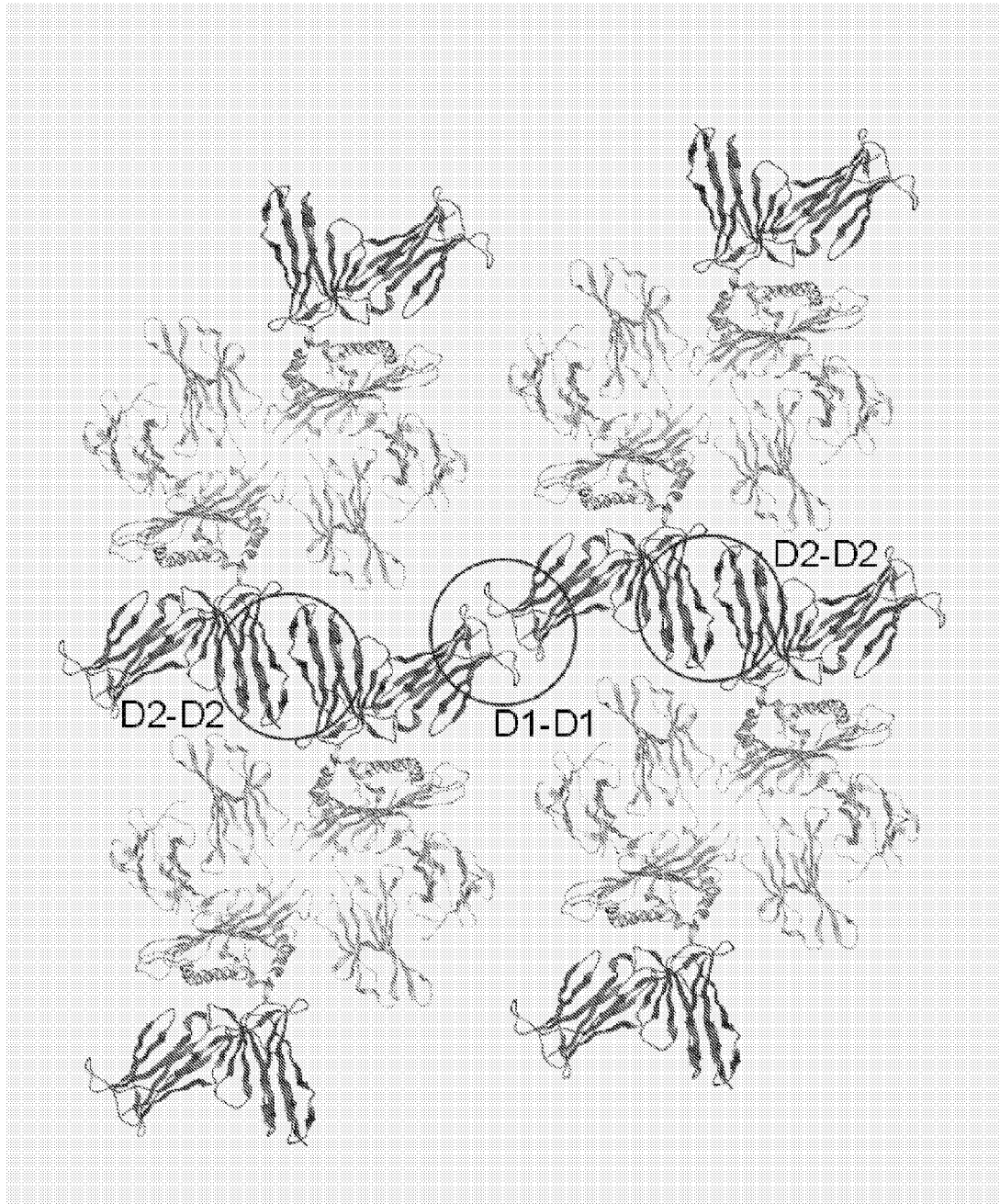
FIG. 1C shows a clustering model of KIR2DL1-HLACw4 in the interface between the NK cell and the target cell. Without being limited to theory, it is believed that upon binding of KIR2DL1 (dark grey) to HLACw4 (light grey), first a set of KIR2DL1-HLACw4 dimers are formed. The dimers are able to form D1-D1 and D2-D2 interaction as illustrated to create a clustering of the dimers in the interface between the NK cell and the target cell.

The interaction sites associated with Domain 1 or Domain 2, were identified by modelling on a specific member of the KIR family, KIR2DL1, and comprise the two conformational interaction sites as shown in FIG. 1 and in Examples 1 and 2. Referring to the amino acid sequence of the extracellular portion of KIR2DL1 (SEQ ID NO:14) and KIR2DS2 (starting at residue 22 of SEQ ID NO:6, see FIG. 3), the following interaction sites have been predicted as explained herein and in Examples 1 and 2.

Interaction site associated with domain 1:
H1, E2, H5, R6, D31, V32, M33, F34, E35, H36, H50, D57, G58, V59, V83, T84, H85, S86, Q89, L90, S91, A92.

Interaction site associated with domain 2:
P108, S109, L110, S111, A112, Q113, P114 (or L114), G115, T125, S127, S129, R131, K155, V156, N157, G158, T159, Q161, A162, D163, S192, D193, P194, L195, L196, V197, S198, V199 and T200.

Thus in one embodiment the interaction site associated with Domain 1 comprises amino acid positions H1, E2, H5, R6, D31, V32, M33, F34, E35, H36, H50, D57, G58, V59, V83, T84, H85, S86, Q89, L90, S91, A92.

In another embodiment the interaction site associated with Domain 2 comprises amino acid positions P108, S109, L110, S111, A112, Q113, P114 (or L114), G115, T125, S127, S129, R131, K155, V156, N157, G158, T159, Q161, A162, D163, S192, D193, P194, L195, L196, V197, S198, V199, and T200.

Domains in other KIRs corresponding to Domains 1 and 2 in KIR2DL1 can be predicted by sequence alignments of KIR2DL, KIR2DS, KIR3DL and KIR3DS sequences. Representative examples are shown in FIGS. 2 and 3, showing alignment of KIR2DL1, 2DL2, 2DL3, 2DL4, 2DS1, 2DS2, 2DS3, 2DS4, 2DS5 with indication ("1" for Domain 1; "2" for Domain 2) of the Domain 1 and Domain 2 interaction residues (FIG. 2), as well as alignment of 3DL1, 3DL2, 3DL3, 3DS1, 2DL1 with indication of the interaction residues associated with Domain 1 and Domain 2 (FIG. 3).

Agents that bind to such homologous sequences in other KIR family members and reduce or block dimerization are also comprised within the scope of the present invention. In the present context a "human KIR gene product" signifies a protein encoded by a KIR gene.

Modeling Approaches

When the 3 dimensional structure of a protein is known from either an X-ray experiment or homology modeling, at least 3 different methods exist to identify residues with functional significance. In the conserved site approach, sites on the protein structure are compared with a sequence alignment to identify conserved sites. In the protein-protein docking approach, a protein may be docked on itself or another protein to identify the functionally significant residues. In the crystal packing approach, X-ray crystals are investigated for how proteins pack onto other proteins of the same or different compositions in the crystal to determine functional sites.

In the conserved site approach, the molecular surface of such a protein can be traversed for potential interaction sites. Each site is defined by its location on the surface and size surrounding the location. When the atoms associated with the site have been determined, the site can be specified in terms of its residue composition. The site defined by its residues can then be compared with the residues in the same positions in a sequence alignment of a series of related proteins e.g. homologues, orthologues, analogues, or chimers and conserved sites with the same residue composition across several related proteins can be identified. Such conserved sites are associated with functional significance (del Sol M A, Pazos F, Valencia A, 2003, J. Mol. Biol. 326:1289-1302).

In the protein-protein docking approach, which has been reviewed recently (Schneidman-Duhovny D, Nussinov R, Wolfson H J, 2004, Curr. Med. Chem. 11:91-107), the two surfaces are represented by features on surfaces. Features include hydrogen bonding capabilities, charges and hydrophobicity. In a grid based methods, space is divided into cubes and each cube is given a value according to its position relative to the surface (interior, surface, exterior) and assigned the relevant feature set. Brute force matching of the surfaces by a scoring function can now be employed by searching the entire 3 translational and 3 rotational degrees of freedom. Translations are handled by Fast Fourier Transform and rotation is treated as individual calculations within a standard discretization of rotational space. From the top scoring complexes the results can be filtered and scored, by a range of methods e.g. shape complementarity, Van der Waals interactions, hydrophobicity, electrostatics, desolvation, hydrogen bonding, atomic contact energy, residue-residue pairing statistics and hydrophilic group pairing. The top-scoring complexes can be evaluated in detail and interacting residues identified.

In the crystal packing approach, X-ray crystals are investigated for how proteins pack onto itself and other proteins in the crystal not only for the symmetry reduced coordinates, but for all relevant packings within the unit-cell and its neighbor cells. In this approach, all proteins within a 3×3×3 grid of unit-cells are analyzed for their interactions, which are mapped onto a pivot table with chain number in a column and residue numbers horizontally across, and interaction counts in the cells. Sorting by the total interaction number for each chain identifies the chains with a complete set of neighbors and one of these can be selected for further analysis in a reduced structure set with only the protein and all its interacting neighbors. Each interaction can be evaluated in detail and interacting residues identified.

Residues with functional significance can now be validated by an investigation of the functional aspects by mutation analysis and serve as a target for a therapeutic agent inhibiting the functional effect.

Antibodies

Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention because they are the most common antibodies in the physiological situation and because they are most easily made in a laboratory setting. In one embodiment the antibody of this invention is a monoclonal antibody, of the IgG4 subclass, or an IgG1 or IgG2 that does not bind to Fc receptors and that does not fix complement, in order to avoid depletion of the NK cells in vivo.

Full-length antibodies comprise four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The antibodies of this invention may be produced by a variety of techniques known in the art. Typically, they are produced by immunization of a non-human animal with an immunogen comprising a KIR polypeptide, e.g. an inhibitory KIR polypeptide, preferably a KIR2DL polypeptide, more preferably a human KIR2DL polypeptide. The KIR polypeptide may comprise the full length sequence of a human KIR polypeptide, or a fragment or derivative thereof, typically an immunogenic fragment, i.e., a portion of the polypeptide comprising an epitope exposed on the surface of the cell expressing an inhibitory KIR receptor. Such fragments typically contain at least 7 consecutive amino acids of the mature polypeptide sequence, even more preferably at least 10 consecutive amino acids thereof. They are essentially derived from the extracellular domain of the receptor. Even more preferred is a human KIR2DL polypeptide which includes at least one, more preferably both, extracellular Ig domains, of the full length KIRDL polypeptide and is capable of mimicking at least one conformational epitope present in a KIR2DL receptor. In other embodiments, said polypeptide comprises at least 8 consecutive amino acids of an extracellular Ig domain of KIR2DL1 (SEQ ID NO:14).

In a most particular embodiment, the immunogen comprises a wildtype human KIR2DL polypeptide in a lipid membrane, typically at the surface of a cell. In a specific embodiment, the immunogen comprises intact NK cells, particularly intact human NK cells, optionally treated or lysed.

In preferred embodiment, the non-human animal is a mammal, such as a rodent (e.g., mouse, rat, etc.), bovine, porcine, horse, rabbit, goat, sheep, etc. Also, the non-human mammal may be genetically modified or engineered to produce "human" antibodies, such as the Xenomouse™ (Abgenix) or HuMAb-Mouse™ (Medarex).

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988)). The immunogen is then suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the pre-sent invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with inhibitory KIR receptors.

In an alternate embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., or X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in (Goding, "Monoclonal Antibodies: Principles and Practice," pp. 59-103 (Academic Press, 1986)).

The cells are allowed to grow in the selection media for sufficient time for colony formation and antibody production. This is usually between 7 and 14 days. The hybridoma colonies are then assayed for the production of antibodies that bind KIR gene products. The assay is typically a colorimetric ELISA-type assay, although several other types of assays may be employed, including immunoprecipitation, radioimmunoassay, Biacore assays, or Scintillation Proximity assays (SPA), as well known in the art. The wells positive for the desired antibody production are examined to determine if one or more distinct colonies are present. If more than one colony is present, the cells may be recloned and grown to ensure that only a single cell has given rise to the colony producing the desired antibody. Positive wells with a single apparent colony are typically re-cloned and re-assayed to insure only one monoclonal antibody is being detected and produced.

Hybridomas that are confirmed to be producing a monoclonal antibody of this invention are then grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by chromatography using protein A or protein G-Sepharose, or an anti-mouse Ig linked to a solid support such as agarose or Sepharose beads (all described, for example, in the Anti-body Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

According to an alternate embodiment, the DNA encoding an antibody of the invention is isolated from the hybridoma, placed in an appropriate expression vector for transfection into an appropriate host. The host is then used for the recombinant production of the antibody, or variants thereof, such as a humanized version of that monoclonal antibody, active fragments of the antibody or chimeric antibodies comprising the antigen recognition portion of the antibody. Particularly, the DNA used in this embodiment encodes an antibody that recognizes a determinant comprising domain 1 and/or domain 2 of KIR2DL gene products, and cause potentiation of NK cells expressing at least one of those KIR receptors.

DNA encoding the monoclonal antibodies of the invention is readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al., Curr. Opinion in Immunol., 5, pp. 256 (1993); and Pluckthun, Immunol. Revs., 130, pp. 151 (1992).

Antibodies may also be produced by selection of combinatorial libraries of immunoglobulins, as disclosed for instance in Ward et al (Nature 341 (1989) 544).

Antibody Fragments and Derivatives

Fragments and derivatives of antibodies of this invention can be produced by techniques that are known in the art. "Immunoreactive fragments" comprise a portion of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments.

For instance, Fab or F(ab')2 fragments may be produced by protease digestion of the isolated antibodies, according to conventional techniques.

Alternatively, the DNA of a hybridoma producing an antibody of this invention may be modified so as to encode for a fragment of this invention. The modified DNA is then inserted into an expression vector and used to transform or transfect an appropriate cell, which then expresses the desired fragment.

In an alternate embodiment, the DNA of a hybridoma producing an antibody of this invention can be modified prior to insertion into an expression vector, for example, by substituting the coding sequence for human heavy- and light-chain constant domains in place of the homologous non-human sequences (e.g., Morrison et al., Proc. Natl. Acad. Sci. U.S.A., 81, pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, the antibodies of the present invention may also be made into "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. U.S.A., 81, pp. 6851 (1984)).

Recombinant production of antibodies from known variable heavy (VH) and variable light (VL) chains, and human constant regions has been described by, for example, Ruker et al. (Annals of the New York Academy of Sciences. 1991; 646:212-219), who reports the expression of a human monoclonal anti-HIV-1 antibody in CHO cells; Bianchi et al. (Biotechnology and Bioengineering. 2003; 84:439-444), who describes high-level expression of fullLength antibodies using trans-complementing expression vectors, No Soo Kim et al. (Biotechnol. Prog. 2001; 17:69-75), who describes key determinants in the occurrence of clonal variation in humanized antibody expression of CHO cells during dihydrofolate reductase mediated gene amplification; King et al. (Biochemical Journal. 1992; 281:317-323), who reports expression, purification and characterization of a mouse-human chimeric antibody and chimeric Fab' fragment; WO 2003064606 which describes isolated human monoclonal antibodies comprising a human heavy and a human light chain variable regions, both comprising FR1, CDR1, FR2, CDR2, FR3, CDR3 and FR4 sequences; and WO 2003040170 which describes chimeric or human monoclonal antibodies and antigen-binding portions that specifically binds to and activates human CD40.

In an exemplary embodiment, a chimeric recombinant mAb from 1-26F117-A3 or 1-26F117-A4 VH and VL sequences, or a derivative or variant thereof, is produced. To sub-clone the antibody genes into mammalian expression vectors, primers are designed for the amplification of the variable light (VL) and variable heavy (VH) chain genes, respectively, based on the cDNAs encoding the heavy and light chain variable regions of the mAb. The variable regions are formatted by PCR to include a Kozak sequence, leader sequence and unique restriction enzyme sites. For the VL, this is achieved by designing 5' PCR primers to introduce a HindIII site, the Kozak sequence and to be homologous to the 5' end of the leader sequence of the variable light chain region. The 3' primer is homologous to the 3' end of the variable region and introduced a BsiWI site at the 3' boundary of the variable region. The VH region is generated in a similar fashion except that a NotI and a NheI site are introduced in the 5' and 3' end instead of HindIII and BsiWI, respectively.

The amplified gene products are each cloned into a commercially available or otherwise known eukaryotic expression vector containing the light and heavy chain constant regions for a human or non-human antibody, using standard techniques. One example of a commercially available vector is pASK84, available from the ATCC (American Type Culture Collection, catalog number 87094). The VL DNA fragments is digested with HindIII and BsiWI and ligated into a eukaryotic expression vector containing the beta-lactamase gene encoding resistance to ampicillin and an *E. coli* replication origin (pUC); the resulting plasmid is designated VLCL. The VH DNA fragments is digested with NotI and NheI and introduced into the VLCL vector resulting from the introduction of VL fragment as described above. The resulting plasmid contains functional expression cassettes encoding both the heavy and light chains of the antibody on the same plasmid. The ligated plasmid is used to transform *E. coli*. Plasmid DNA is prepared from these ampicillin resistant bacterial populations and used for transfection into CHO cells, or other mammalian cell lines. Transfection and cell culture can be made by standard methods, as described for example in "Molecular Cloning", Sambrook et al. The result is transfected cell lines that stably express and secrete the antibody molecule of interest, such as a chimeric version of 1-26F117 comprising its original VH and VL regions and the constant regions from a human mAb.

The entire cDNA sequences encoding the constant regions of human IgG can be found in the following GenBank entries, each of which incorporated by reference in its entirety:

Human IgG1 constant heavy chain region: GenBank accession #: J00228

Human IgG2 constant heavy chain region: GenBank accession #: J00230

Human IgG3 constant heavy chain region: GenBank accession #: X04646

Human IgG4 constant heavy chain region: GenBank accession #: K01316

Human kappa light chain constant region: GenBank accession #: J00241.

Alternatively, VH and VL regions of 1-26F117-A3 or 1-26F117-A4, or mutants or derivatives thereof, can be cloned into vectors encoding truncated constant regions in order to express antibody fragments (e.g., Fab fragments).

Isotype-switching of antibody can be made according to similar principles. For example, an antibody with the exact same specificity as 1-26F117-A3 or -A4 but of a different isotype can be obtained by sub-cloning the cDNA encoding VL and VH sequences into plasmids containing cDNA encoding the kappa light chain constant regions and a heavy constant chain region selected from IgG1 or IgG2 or IgG3 or IgG4 constant heavy chain regions. Thus, an antibody as generated can possess any isotype and the antibody can then be iso-type switched using conventional techniques in the art. Such techniques include the use of direct recombinant techniques (see, e.g., U.S. Pat. No. 4,816,397), cell-cell fusion techniques (see e.g., U.S. Pat. No. 5,916,771), and other suitable techniques known in the art. Accordingly, the effector function of antibodies provided by the invention may be "changed" with respect to the isotype of a parent antibody by isotype switching to, e.g., an IgG1, IgG2, IgG3, IgG4, IgD, IgA, IgE, or IgM antibody for various therapeutic or other uses.

According to another embodiment, the antibody of this invention is humanized. "Humanized" forms of antibodies according to this invention are specific chimeric immunoglobulins, immunoglobulin chains or fragments thereof (such as Fv, Fab, Fab', F(ab')2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize anti-body performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al., Nature, 332, pp. 323 (1988); and Presta, Curr. Op. Struct. Biol., 2, pp. 593 (1992). Accordingly, humanized versions of 1-26F117-A3 or 1-26F117-A4 comprising the VH and VL CDR regions of 1-26F117-A3 or 1-26F117-A4 and constant and framework regions from a human mAb can be made, using known constant and framework human mAb sequences and established techniques in the art, as described herein.

Methods for humanizing the antibodies of this invention are well known in the art. Generally, a humanized antibody according to the present invention has one or more amino acid residues introduced into it from the original antibody. These murine or other non-human amino acid residues are often referred to as "import" residues, which are typically taken from an "import" variable domain. Humanization can be essentially performed following the method of Winter and co-workers (Jones et al., Nature, 321, pp. 522 (1986); Riechmann et al., Nature, 332, pp. 323 (1988); Verhoeyen et al., Science, 239, pp. 1534 (1988)). Accordingly, such "humanized" antibodies are chimeric antibodies (Cabilly et al., U.S. Pat. No. 4,816,567), wherein substantially less than an intact human variable domain has been substituted by the corresponding sequence from the original antibody. In practice, humanized antibodies according to this invention are typically human antibodies in which some CDR residues and possibly some FR residues are substituted by residues from analogous sites in the original antibody.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al., J. Immunol., 151, pp. 2296 (1993); Chothia and Lesk, J. Mol. Biol., 196, pp. 901 (1987)). Another method uses a particular framework from the consensus sequence of all human antibodies of a particular subgroup of light or heavy chains. The same framework can be used for several different humanized antibodies (Carter et al., Proc. Natl. Acad. Sci. U.S.A., 89, pp. 4285 (1992); Presta et al., J. Immunol., 51, pp. 1993)).

It is further important that antibodies be humanized with retention of high affinity for multiple inhibitory KIR receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Another method of making "humanized" monoclonal antibodies is to use a XenoMouse® (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already human. The XenoMouse is described in U.S. Pat. No. 6,162, 963. An analogous method can be achieved using a HuMAb-Mouse™ (Medarex).

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

Other derivatives within the scope of this invention include functionalized antibodies, i.e., antibodies that are conjugated or covalently bound to a toxin, such as ricin, diphtheria toxin, abrin and *Pseudomonas* exotoxin; to a detectable moiety, such as a fluorescent moiety, a radioisotope or an imaging agent; a PEG-molecule; or to a solid support, such as agarose beads or the like. Methods for conjugation or covalent bonding of these other agents to antibodies are well known in the art.

Conjugation to a detectable moiety is useful when the antibody of this invention is used for diagnostic purposes. Such purposes include, but are not limited to, assaying biological samples for the presence of the NK cells bearing the KIR on their cell surface and detecting the presence of NK cells bearing the KIR in a living organism. Such assay and detection methods are also alternate embodiments of the present invention.

Conjugation of an antibody of this invention to a solid support is useful as a tool for affinity purification of NK cells bearing the KIR on their cell surface from a source, such as a biological fluid. This method of purification is another alternate embodiment of the present invention, as is the resulting purified population of NK cells.

In an alternate embodiment, the antibodies of this invention may be incorporated into liposomes ("immunoliposomes"), alone or together with another substance for targeted delivery to an animal. Such other substances include nucleic acids for the delivery of genes for gene therapy or for the delivery of antisense RNA, RNAi or siRNA for suppressing a gene in an NK cell, or toxins or drugs for the targeted killing of NK cells.

The above described method for producing an antibody or an antibody fragment that binds a determinant on a human KIR receptor gene product, wherein said antibody is capable of reducing KIR-mediated inhibition of NK cell cytotoxicity can also be applied for the isolation of other agents. In one particular embodiment the invention relates to a method for isolating an agent capable of neutralizing KIR mediated inhibition of NK cell cytotoxicity by:

a) providing a pool of test agents; and
b) selecting test agents that reduce or block dimerization of KIR under conditions conducive for dimerization (such as the presence of target cells expressing HLA-C or other KIR-ligands);
c) selecting any agent from (b) that is capable of neutralizing KIR-mediated inhibition of NK cell cytotoxicity, wherein the order of steps (b) and (c) is optionally reversed.

In another particular embodiment, the invention relates to a method for isolating an agent capable of neutralizing KIR mediated inhibition of NK cell cytotoxicity by:

a) providing a pool of test agents; and
b) selecting test agents that do not detectably and/or substantially reduce or block the binding of KIR and HLA under conditions conducive for KIR binding to HLA-C (such as the presence of target cells expressing HLA-C or other KIR-ligands);
c) selecting any agent from (b) that is capable of neutralizing KIR-mediated inhibition of NK cell cytotoxicity, wherein the order of steps (b) and (c) is optionally reversed.

Compositions and Administration

The invention also provides compositions that comprise an agent, e.g., an antibody as defined above, including fragments and derivatives thereof, in any suitable vehicle in an amount effective to detectably potentiate NK cell cytotoxicity in a patient or in a biological sample comprising NK cells. The composition further comprises a pharmaceutically acceptable carrier.

The term "biological sample" as used herein includes but is not limited to a biological fluid (for example serum, lymph, or blood), cell sample or tissue sample (for example bone marrow).

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of this invention may be employed in a method of potentiating the activity of NK cells in a patient or a biological sample. This method comprises the step of contacting said composition with said patient or biological sample. Such method will be useful for both diagnostic and therapeutic purposes.

In a particular embodiment, the invention relates to a method of reducing KIRmediated inhibition of NK cell cytotoxicity without reducing KIR-binding to its HLA-ligand, e.g., by reducing or blocking dimerization of KIR.

In a further embodiment, dimerization is blocked by binding of an agent to a determinant affecting interaction between interaction sites associated with Domain 1 or 2 of KIR2DL1, -2 or -3, or to homologous interaction sites in all KIRs, as well as potential other KIRs.

In a further embodiment, the invention relates to a method of reducing KIR-mediated inhibition of NK cell cytotoxicity using an agent, such as an antibody, which competes with an antibody comprising the VH and VL sequences of antibody 1-26F117-A3 or -A4 in binding to at least one of KIR2DL1 and KIR2DL3.

In a further embodiment, the invention relates to a method of reducing KIR-mediated inhibition of NK cell cytotoxicity using an agent, such as an antibody, which binds to the KIR2DL1 and/or KIR2DL3 epitope recognized by an antibody comprising the VH and VL sequences of antibody 1-26F117-A3 or -A4.

For use in conjunction with a biological sample, the antibody composition can be administered by simply mixing with or applying directly to the sample, depending upon the nature of the sample (fluid or solid). The biological sample may be contacted directly with the antibody in any suitable device (plate, pouch, flask, etc.). For use in conjunction with a patient, the composition must be formulated for administration to the patient.

Another object of the present invention is to provide a pharmaceutical formulation comprising an anti-KIR binding agent which is present in a concentration from 1 mg/ml to 500 mg/ml, and wherein said formulation has a pH from 2.0 to 10.0. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of the agent, and a buffer, wherein the agent is present in a concentration from 1 mg/ml or above, and wherein said formulation has a pH from about 2.0 to about 10.0.

In a another embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention, the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-76; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyranosoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, NHexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

In a further embodiment of the invention the formulation further comprises protease inhibitors such as EDTA (ethylenediamine tetraacetic acid) and benzamidineHCl, but other commercially available protease inhibitors may also be used.

The use of a protease inhibitor is particular useful in pharmaceutical compositions comprising zymogens of proteases in order to inhibit autocatalysis.

It is possible that other ingredients may be present in the pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an agent according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block copolymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the agent, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the agent in the form of a nasal or pulmonal spray. As a still further option, the pharmaceutical compositions containing the agent of the invention can also be adapted to transdermal administration, e.g. by needle-free injection or from a patch, optionally an iontophoretic patch, or transmucosal, e.g. buccal, administration.

The agent can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit. Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

$$d_a = \sqrt{\frac{\rho}{\rho_a}}\, d$$

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 µm, more preferably between 1-5 µm, and most preferably between 1-3 µm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the agent may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of a protein (e.g., an antibody) formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising an agent of the invention is stable for more than 6 weeks of usage and for more than 3 years of storage.

In another embodiment of the invention the pharmaceutical formulation comprising an agent of the invention is stable for more than 4 weeks of usage and for more than 3 years of storage.

In a further embodiment of the invention the pharmaceutical formulation comprising an agent of the invention is stable for more than 4 weeks of usage and for more than two years of storage.

In an even further embodiment of the invention the pharmaceutical formulation comprising the agent of the invention is stable for more than 2 weeks of usage and for more than two years of storage.

As described above, the compositions of the present invention may be administered, e.g., orally, parenterally, by inhalation spray, topically, rectally, nasally, buccally, vaginally or via an implanted reservoir. The term "parenteral" as used herein includes subcutaneous, intravenous, intramuscular, intraarticular, intrasynovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxy-methyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Several monoclonal antibodies have been shown to be efficient in clinical situations, such as Rituxan (Rituximab), Herceptin (Trastuzumab) or Xolair (Omalizumab), and similar administration regimens (i.e., formulations and/or doses and/or administration protocols) may be used with the antibodies of this invention. Schedules and dosages for administration can be determined in accordance with known methods for these products, for example using the manufacturers' instructions. For example, a monoclonal antibody can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for a cross-reacting KIR antibody of the invention may between about 10 mg/m$^2$ and 500 mg/m$^2$. However, it will be appreciated that these schedules are exemplary and that optimal schedule and regimen can be adapted taking into account the affinity of the antibody and the tolerability of the anti KIR antibodies that must be determined in clinical trials. Quantities and schedule of injection of anti KIR that saturate NK cells for 24 hours, 48 hours 72 hours or a week or a month will be determined considering the affinity of the antibody and the its pharmacokinetic parameters.

According to another embodiment, the antibody compositions of this invention may further comprise another therapeutic agent, including agents normally utilized for the particular therapeutic purpose for which the antibody is being administered. The additional therapeutic agent will normally be present in the composition in amounts typically used for that agent in a mono-therapy for the particular disease or condition being treated. Such therapeutic agents include, but are not limited to, therapeutic agents used in the treatment of cancers, therapeutic agents used to treat infectious disease, therapeutic agents used in other immunotherapies, cytokines (such as IL-2 or IL-15), other antibodies and fragments of other antibodies.

For example, a number of therapeutic agents are available for the treatment of cancers. The antibody compositions and methods of the present invention may be combined with any other methods generally employed in the treatment of the particular disease, particularly a tumor, cancer disease, or other disease or disorder that the patient exhibits. So long as a particular therapeutic approach is not known to be detrimental to the patient's condition in itself, and does not significantly counteract the inhibitory KIR antibody-based treatment, its combination with the present invention is contemplated.

In connection with solid tumor treatment, the present invention may be used in combination with classical approaches, such as surgery, radiotherapy, chemotherapy, and the like. The invention therefore provides combined therapies in which KIR antibodies according to the invention are used simultaneously with, before, or after surgery or radiation treatment; or are administered to patients with, before, or after conventional chemotherapeutic, radiotherapeutic or anti-angiogenic agents, or targeted immunotoxins or coaguligands.

When one or more agents are used in combination with a composition of this invention in a therapeutic regimen, there is no requirement for the combined results to be additive of the effects observed when each treatment is conducted separately. Although at least additive effects are generally desirable, any increased anti-cancer effect above one of the single therapies would be of benefit. Also, there is no particular requirement for the combined treatment to exhibit synergistic effects, although this is possible and advantageous.

To practice combined anti-cancer therapy, one would simply administer to a patient a composition of this invention in combination with another anti-cancer agent in a manner effective to result in their combined anti-cancer actions within the animal. The agents would therefore be provided in amounts effective and for periods of time effective to result in their combined presence within the tumor vasculature and their combined actions in the tumor environment. To achieve this goal, a composition of this invention and anti-cancer agents may be administered to the patient simultaneously, either in a single combined composition, or as two distinct compositions using the same or different administration routes.

Alternatively, the administration of a composition of this invention may precede, or follow, the anti-cancer agent treatment by, e.g., intervals ranging from minutes to weeks and months. One would ensure that the anti-cancer agent and the active agent in the composition of this invention exert an advantageously combined effect on the cancer. As an example, antibodies of the present invention may be administered to patients with Non-Hodgkin's Lymphoma (NHL). Such patients are typically treated with a combination of Rituximab and a combination of chemotherapy agents known as CHOP. Accordingly, anti-KIR antibodies of this invention may be used to treat NHL patients who are undergoing treatment with Rituximab and CHOP, by combining the administration of all the agents in a treatment schedule where the agents are given on the same day, or on different days, with a longer treatment-period.

Other anti-cancer agents may be given prior to, at the same time as, or following administration of a composition of this invention. However, when immunoconjugates of an antibody are used in the antibody composition of this invention, various anti-cancer agents may be simultaneously or subsequently administered.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administration of the anti-cancer agent or anti-cancer treatment and the administration of a composition of this invention. This might be advantageous in circumstances where the anti-cancer treatment was intended to substantially destroy the tumor, such as surgery or chemotherapy, and administration of a composition of this invention was intended to prevent micrometastasis or tumor re-growth.

It also is envisioned that more than one administration of either an anti-KIR agent-based composition of this invention or the anti-cancer agent will be utilized. These agents may be administered interchangeably, on alternate days or weeks; or a cycle of treatment with an anti-KIR agent composition of this invention, followed by a cycle of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within cancer cells is contemplated, such as gamma-irradiation, X-rays, UV-irradiation, microwaves and even electronic emissions and the like. The directed delivery of radioisotopes to cancer cells is also contemplated, and this may be used in connection with a targeting antibody or other targeting means.

In other aspects, immunomodulatory compounds or regimens may be administered in combination with or as part of the compositions of the present invention. Preferred examples of immunomodulatory compounds include cytokines. Various cytokines may be employed in such combined approaches. Examples of cytokines useful in the combinations contemplated by this invention include IL-1 alpha IL-1 beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNFalpha, TNF-beta, LAF, TCGF, BCGF, TRF, BAF, BDG, MP, LIF, OSM, TMF, PDGF, IFN-alpha, IFN-beta, IFN-gamma. Cytokines used in the combination treatment or compositions of this invention are administered according to standard regimens, consistent with clinical indications such as the condition of the patient and relative toxicity of the cytokine. Other immunomodulatory compounds that may be administered in combination with, or as part of, the compositions of the present invention include antibodies that bind specifically to other inhibitory receptors on lymphocytes, including without limitation antibodies such as anti-CTLA4 antibodies, or anti-CD94/NKG2A antibodies (see, for example, U.S. published patent application 20030095965). Variants and derivatives of these molecules that are known in the art also or alternatively can be used in such methods, and incorporated into compositions of the invention, as appropriate.

In certain embodiments, the non-HLA-blocking, inhibitory, optionally blocking anti-KIR antibody-comprising therapeutic compositions of the present invention may be administered in combination with, or may further comprise, a chemotherapeutic or hormonal therapy agent. A variety of hormonal therapy and chemotherapeutic agents may be used in the combined treatment methods disclosed herein. Chemotherapeutic agents contemplated as exemplary include, but are not limited to, alkylating agents, antimetabolites, cytotoxic antibiotics, vinca alkaloids, for example adriamycin, dactinomycin, mitomycin, caminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s) and derivatives and prodrugs thereof.

Hormonal agents include, but are not limited to, for example LHRH agonists such as leuprorelin, goserelin, triptorelin, and buserelin; anti-estrogens such as tamoxifen and toremifene; anti-androgens such as flutamide, nilutamide, cyproterone and bicalutamide; aromatase inhibitors such as anastrozole, exemestane, letrozole and fadrozole; and progestagens such as medroxy, chlormadinone and megestrol.

As will be understood by those of ordinary skill in the art, the appropriate doses of chemotherapeutic agents will approximate those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m2 for 5 days every three weeks for a total of three courses. Cisplatin is not absorbed orally and must therefore be delivered via injection intravenously, subcutaneously, intratumorally or intraperitoneally.

Further useful chemotherapeutic agents include compounds that interfere with DNA replication, mitosis and chromosomal segregation, and agents that disrupt the synthesis and fidelity of polynucleotide precursors. A number of exemplary chemotherapeutic agents for combined therapy are listed in Table C of U.S. Pat. No. 6,524,583, the disclosure of which agents and indications are specifically incorporated herein by reference. Each of the agents listed are exemplary and not limiting. The skilled artisan is directed to "Remington's Pharmaceutical Sciences" 15th Edition, chapter 33, in particular pages 624-652. Variation in dosage will likely occur depending on the condition being treated. The physician administering treatment will be able to determine the appropriate dose for the individual subject.

The compositions of this invention may be used in combination with any one or more anti-angiogenic therapies or may further comprise anti-angiogenic agents. Examples of such agents include neutralizing antibodies, antisense RNA, siRNA, RNAi, RNA aptamers and ribozymes each directed against VEGF or VEGF receptors (U.S. Pat. No. 6,524,583, the disclosure of which is incorporated herein by reference). Variants of VEGF with antagonistic properties may also be employed, as described in WO 98/16551, specifically incorporated herein by reference. Further exemplary anti-angiogenic agents that are useful in connection with combined therapy are listed in Table D of U.S. Pat. No. 6,524,583, the disclosure of which agents and indications are specifically incorporated herein by reference.

The compositions of this invention may also be advantageously used in combination with methods to induce apoptosis or may comprise apoptotic agents. For example, a number of oncogenes have been identified that inhibit apoptosis, or programmed cell death. Exemplary oncogenes in this category include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-x1, Mc1-1, Bak, A1, and A20. Overexpression of bcl-2 was first discovered in T cell lymphomas. The oncogene bcl-2 functions by binding and inactivating Bax, a protein in the apoptotic pathway. Inhibition of bcl-2 function prevents inactivation of Bax, and allows the apoptotic pathway to proceed. Inhibition of this class of oncogenes, e.g., using antisense nucleotide sequences, RNAi, siRNA or small molecule chemical compounds, is contemplated for use in the present invention to give enhancement of apoptosis (U.S. Pat. Nos. 5,650,491; 5,539,094; and 5,583,034; each incorporated herein by reference).

The anti-KIR agent compositions of this invention may also comprise or be used in combination with molecules that comprise a targeting portion, e.g., antibody, ligand, or conjugate thereof, directed to a specific marker on a target cell ("targeting agent"), for example a target tumor cell. Generally speaking, targeting agents for use in these additional aspects of the invention will preferably recognize accessible tumor antigens that are preferentially, or specifically, expressed in the tumor site. The targeting agents will generally bind to a surface-expressed, surface-accessible or surface-localized component of a tumor cell. The targeting agents will also preferably exhibit properties of high affinity; and will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "not exert significant side effects," as used herein, refers to the fact that a targeting agent, when administered in vivo, will produce only negligible or clinically manageable side effects, such as those normally encountered during chemotherapy.

In the treatment of tumors, a composition of this invention may additionally comprise or may be used in combination with adjunct compounds. Adjunct compounds may include by way of example anti-emetics such as serotonin antagonists and therapies such as phenothiazines, substituted benzamides, antihistamines, butyrophenones, corticosteroids, benzodiazepines and cannabinoids; bisphosphonates such as zoledronic acid and pamidronic acid; and hematopoietic growth factors such as erythropoietin and G-CSF, for example filgrastim, lenograstim and darbepoietin.

In another embodiment, two or more antibodies or other agents of this invention recognizing different epitopes or determinants may be combined in a single composition so as to reduce or neutralize the inhibitory effects of as many KIR gene products as possible. Compositions comprising combinations of cross-reactive inhibitory KIR antibodies of this invention, or fragments or derivatives thereof, will allow even wider utility because there likely exists a small percentage of the human population that may lack each of the inhibitory KIR gene products recognized by a single cross-reacting antibody. Similarly, an antibody composition of this invention may further comprise one or more cross-reactive or non-cross-reactive antibodies that block KIR-binding to HLA. Such combinations would again provide wider utility in a therapeutic setting. Accordingly, an antibody of this invention can be combined with another anti-KIR antibody blocking the HLA-binding of one or more of, e.g., KIR2DL1, KIR2DLK2, KIR2DL3, KIR3DL1, KIR3DL2, and KIR3DL3.

The invention also provides a method of potentiating NK cell activity in a patient in need thereof, comprising the step of administering a composition according to this invention to said patient. The method is more specifically directed at increasing NK cell activity in patients having a disease in which increased NK cell activity is beneficial, which involves, affects or is caused by cells susceptible to lysis by NK cells, or which is caused or characterized by insufficient NK cell activity, such as a cancer, an infectious disease or an immune disorder.

More specifically, the methods and compositions of the present invention are utilized for the treatment of a variety of cancers and other proliferative diseases including, but not limited to: carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias, promyelocytic leukemia, and myelodysplastic syndrome; tumors of mesenchymal origin, including fibrosarcoma and rhabdomyoscarcoma; other tumors, including melanoma, seminoma, terato-carcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

Preferred disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; Large granular lymphocyte leukemia (LGL) preferably of the T-cell Type; Sezary syndrome (SS); Adult T-cell leukemia lymphoma (ATLL); a/d T-NHL hepatosplenic lymphoma; Peripheral/post-thymic T cell lymphoma (pleomorphic and immunoblastic subtypes); Angio immunoblastic T-cell lymphoma; Angiocentric (nasal) T-cell lymphoma; Anaplastic (Ki 1+) large cell lymphoma; Intestinal T-cell lymphoma; T-lymphoblastic; Lymphoma/leukaemia (T-Lbly/T-ALL).

Other proliferative disorders can also be treated according to the invention, including for example hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. The KIR antibody based treatment can be used to treat or prevent infectious diseases, including preferably any infections caused by infection by viruses, bacteria, protozoa, molds or fungi. Such viral infectious organisms include, but are not limited to, hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus, echinovirus, arbovirus, huntavirus, coxsackie virus, mumps virus, measles virus, rubella virus, polio virus and human immunodeficiency virus type I or type 2 (HIV-1, HIV-2). Bacteria constitute another preferred class of infectious organisms including but are not limited to the following: *Staphylococcus; Streptococcus*, including *S. pyogenes; Enterococcl; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponerna; Camplyobacter, Pseudomonas* including *P. aeruginosa; Legionella; Neisseria* including *N. gonorrhoeae* and *N. meningitides; Flavobacterium* including *F. meningosepticum* and *F. odoraturn; Brucella; Bordetella* including *B. pertussis* and *B. bronchiseptica; Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus; Rickeftsiaceae* including *R. fickettsfi, Chlamydia* including *C. psittaci* and *C. trachornatis; Mycobacterium* including *M. tuberculosis, M. intracellulare, M. folluiturn, M. Iaprae, M. avium, M. bovis, M. africanum, M. kansasii, M. intracellulare*, and *M. lepraernurium*; and *Nocardia*. Protozoa may include but are not limited to, *leishmania, kokzidioa*, and *trypanosoma*. Parasites include but are not limited to, chlamydia and rickeftsia. A complete list of infectious diseases can be found on the website of the National Center for Infectious Disease (NCID) at the Center for Disease Control (CDC) (World-Wide Web (www) address cdc.gov/ncidod/diseases/), which list is incorporated herein by reference. All of said diseases are candidates for treatment using the inhibitory, optionally crossreacting, KIR antibodies of the invention.

Such methods may employ the agents, e.g. antibodies, fragments and derivatives of this invention, either alone or in combination with other treatments and/or therapeutic agents, such as radiotherapy, chemotherapy or gene therapy. When these methods involve additional treatments with therapeutic agents, those agents may be administered together with the antibodies of this invention as either a single dosage form or as separate, multiple dosage forms. When administered as a separate dosage form, the additional agent may be administered prior to, simultaneously with, of following administration of the antibody of this invention.

Further aspects and advantages of this invention will be disclosed in the following experimental section, which should be regarded as illustrative and not limiting the scope of this application.

EXAMPLES

Example 1

Identification of Interaction Sites Associated with Domain 1 and 2 of KIR

Using the above discussed general approaches possible domains involved in the dimerization of KIR2DL1 were discovered.

The present Example shows that transduction of negative signaling via KIR, upon binding of KIR to its HLA class I ligand, involves a ligand-binding induced, conformational reorientation of the KIR molecules allowing Domain 1-Domain 1 and Domain 2-Domain 2 interactions to form between adjacent KIRs, leading to accelerated clustering. Although it was previously known that ligand-binding leads to signaling via KIR, no mechanisms has been described that could fully explain how ligand-binding, to the extracellular part of KIR on the outside of the cell, could be transmitted to the cytoplasmic tail of KIR and lead to signaling only when ligand is bound, but not when there is no ligand-binding. The discovery of sites on KIR that allow dimerization of KIR molecules can now provide an explanation for this, and allow the development of therapeutic agents that would prevent inhibitory signaling via KIR, by targeting these sites.

Analysis

This Example uses the residue and domain nomenclature for KIR according to Fan et al., 1997, Nature vol. 389: 96-100: Domain 1 comprises residues 6-101 of KIR and Domain 2 comprises amino acids residues 105-200.

Using the conserved site approach on the structure of KIR2DL1 (1 NKR.pdb) and an alignment of KIR2DL1 (Human), KIR2DL2 (Human), KIR2DL3 (Human), KIR2DS1

(Human), KIR2DS2 (Human), KIR2DS3 (Human), KIR2DS4 (Human), KIR (Q8MK11, Rhesus monkey), KIR (Q8MK12, Rhesus monkey) the following conserved site was identified: P108, S109, L110, S111, A112, Q113, P114, G115, T125, S127, S129, T159, Q161, A162, D163, S192, L195.

Using the protein-protein docking approach where 2 KIR2DL1-HLA CW4 complexes from 1 IM9.pdb have been placed on top of the H2K dimer, suggested by Mitra et al. 2004 (Current Biology vol. 14: 718-724), identified how this KIR-HLA dimer allows cluster growth both through Domain 1-Domain 1: R6, D31, V32, M33, F34, E35, D57, G58, V59, V83, T84, H85, S86, Q89 and Domain 2-Domain 2: S109, L110, S111, A112, Q113, T125, S127, S129, R131, K155, V156, N157, G158, T159, Q161, D163, L195 interactions.

Using the crystal packing approach each protein in the X-ray structure of KIR2DS2 (1M4K.pdb) was identified as having 6 interacting neighbors, one of these is a symmetric Domain 1-Domain 1 interaction where V32, M33, F34, V83, T84, Q89, L90, S91, A92 interacts with the same residues on another protein. The C terminals are facing the same side consistent with a membrane bound protein. Since the sequence of 2DS2 is identical to 2DL2 in the interactions region the residues are consistent with the docking results. Further the location of the N-terminal is undetermined in all KIR X-ray structures which can be explained by two Zn-sites crosslinking the Domain 1-Domain 1 interaction: The 2 Zn-sites are E2(A), H5(A), D31 (A), H85(B) and H1(A), E35(B), H36(B), H50(B).

Consequently we define the interaction site associated with Domain 1: H1, E2, H5, R6, D31, V32, M33, F34, E35, H36, H50, D57, G58, V59, V83, T84, H85, S86, Q89, L90, S91, A92 and the interaction site associated with Domain 2: P108, S109, L110, S111, A112, Q113, P114, G115, T125, S127, S129, R131, K155, V156, N157, G158, T159, Q161, A162, D163, S192, L195 and claim that any therapeutic agent interacting with one or more of these residues will reduce or prevent signaling of the KIR receptor. See FIGS. 1A to 1C for illustration.

The protein data base (PDB; Protein Data Bank) referred to herein is described in: H. M. Berman, J. Westbrook, Z. Feng, G. Gilliland, T. N. Bhat, H. Weissig, I. N. Shindyalov, P. E. Bourne: The Protein Data Bank. Nucleic Acids Research, 28 pp. 235-242 (2000).

PDB identifiers are always 4 alphanumeric characters e.g. 1 NKR & 1OM3, some times referred to as 1 NKR.pdb & 1OM3.pdb.

Example 2

Crystal Structure of KIR2DL1 in complex with HuKIR1-7F9-Fab' Reveal KIR2DL1/KIR2DL1 Homodimers The crystal structure of KIR2DL1 in complex with the Fab' fragment of cross-reactive anti-KIR antibody 1-7F9 was solved and refined to 2.35 Å resolution with X-ray crystallography. The results confirmed that in the crystal structure there is a KIR2DL1-KIR2DL1 dimer interface.

Materials and Methods

Extracellular KIR2DL1 (amino acid 1-223 of SEQ ID NO:14, with residue 16 being arginine (R) and residue 114 being leucine (L), and including an additional N-terminal methionine (M) residue), and human anti-KIR Fab' of 1-7F9 (with the light chain sequence of SEQ ID NO:24 and heavy chain sequence of residues 1-221 of SEQ ID NO:25) were mixed, with a slight excess of KIR2DL1, and the complex was purified on a gel-filtration column. The complex was then concentrated to about 13.5 mg/ml. Crystals were grown with the hanging drop-technique in 10% PEG6000 and 500 mM citrate buffer with a pH of 4.2. Crystals were flash frozen in liquid N2 and crystallographic data to 2.35 Å resolution were collected at 100 K using the beam-line BL711I, MAX-lab, Lund, Sweden. Data were integrated by the XDS program (Kabsch, J. Appl. Crystallogr. 1993; 26:795-800). For structure determination molecular replacement, using the MOLREP program of the CCP4 suite (Bailey, Acta Crystallogr. Sect. D-Biol. Crystallogr. 1994; 50:760-763) and the PDB-deposited structures 1 RZJ (the Fab part1) and 1 NKR (KIR), were used. Phase improvements were made with the ARP/WARP program (Lamzin and Wilson, Acta Crystallogr. Sect. D-Biol. Crystallogr. 1993; 49:129-147) and manual modifications to the X-ray derived structure model were made with the QUANTA program (available from Accelrys Inc., San Diego, Calif., USA). Refinement was carried out in the REFMAC5 computer program of the CCP4 suite. Water molecules were added by the ARP/WARP program. The model comprised residues 6-114 and 124-200 of KIR2DL1, 1-212 of the 1-7F9 light chain and 1-136 together with 143-224 of the 1-7F9 heavy chain. In addition, 330 water molecules were placed. R- and R-free for the model were 0.191 and 0.253, respectively.

Results

Figure 4:
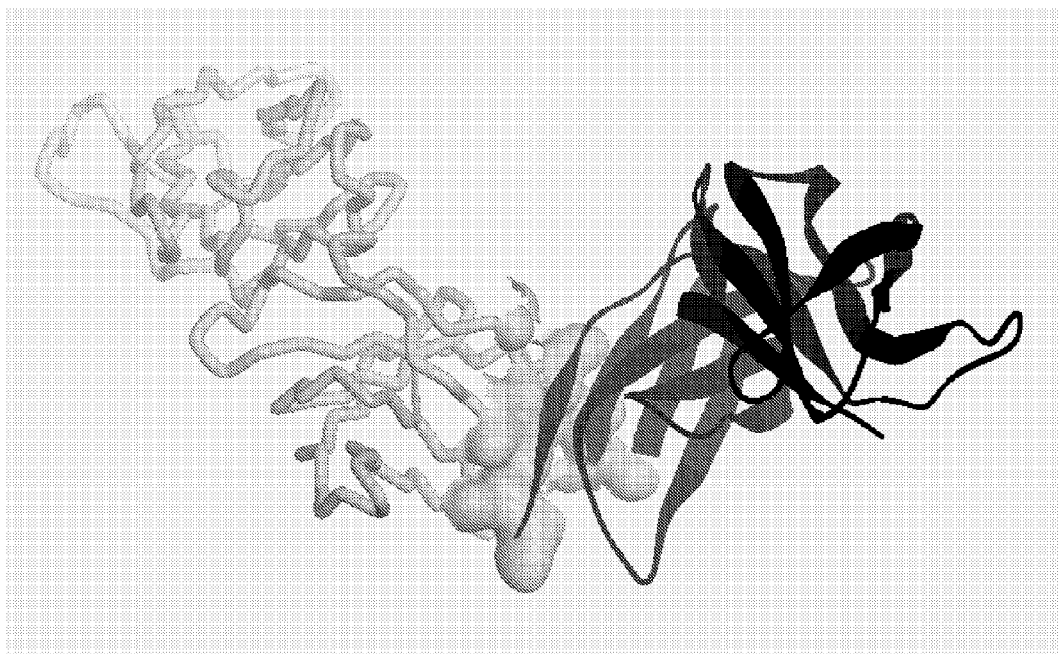
FIG. 4 shows two symmetry related KIR2DL1 molecules (X, Y Z and Y, X, 1/3-Z, respectively) in the crystal packing of KIR2DL1/1-7F9 Fab' structure (REF analysis). The first KIR2DL1 molecule is indicated in grey tube representation together with a surface representation of the residues involved in dimer interaction with the second molecule. The second KIR2DL1 molecule is indicated in black solid ribbon representation.

The contact residues between KIR2DL1 with symmetry "X, Y, Z" and "Y, X, 1/3-Z" were identified by the CONTACT computer program of the CCP4 suite using a cut-off distance of 4.0 Å. The resulting dimer interface area in Domain 2 of KIR was found to comprise the following residues of KIR2DL1 (SEQ ID NO:14): L110, S111, A112, Q113, L114, D193, P194, L195, L196, V197, S198, V199 and T200). The KIR2DL1 dimer interface, and the residues involved in hydrogen-binding, are also indicated in the amino-acid sequence of KIR2DL1 in FIG. 4. The dimer interface area was calculated by the CCP4 program AREAIMAOL to be 665 Å2. In the crystal packing, the loop of KIR2DL1 containing residues 115-123 is not ordered. The biological important interface residues can therefore also contain residues within that range.

Table 1 shows KIR2DL1-KIR2DL1 interactions in the crystal structure of KIR2DL1 in complex with 1-7F9 Fab' VL chain. A cut-off of 4.0 Å was used. The contacts were identified by the CONTACT computer program of the CCP4 suite using symmetry cards (X,Y,Z) and (Y,X,1/3-Z). In the last column "***" indicates the strong possibility of a hydrogen bond at this contact (distance<3.3 Å) as calculated by CONTACT, "*" indicates a weak possibility (distance>3.3 Å). Blank indicates that the program considered there to be no possibility of a hydrogen bond. Water molecules were ignored in the calculations.

TABLE 1

KIR2DL1-KIR2DL1 interactions

| Source atoms | | | Target atoms | | | Distance | Possible H-bond |
|---|---|---|---|---|---|---|---|
| Leu | 110A | O | Leu | 196A | CB | 3.84 | |
| Ser | 111A | CA | Leu | 196A | O | 3.38 | |
| Ser | 111A | CB | Leu | 196A | C | 3.97 | |
| | | | Leu | 196A | O | 3.53 | |
| | | | Leu | 196A | CG | 3.59 | |
| | | | Leu | 196A | CD2 | 3.65 | |
| Ser | 111A | OG | Ser | 198A | OG | 3.24 | *** |
| | | | Ser | 198A | CB | 3.92 | |
| Ser | 111A | C | Leu | 196A | O | 3.64 | |

TABLE 1-continued

KIR2DL1-KIR2DL1 interactions

| Source atoms | | | Target atoms | | | Distance | Possible H-bond |
|---|---|---|---|---|---|---|---|
| Ala | 112A | N | Leu | 196A | O | 2.90 | *** |
| Ala | 112A | CA | Leu | 196A | O | 3.89 | |
| Ala | 112A | CB | Leu | 196A | O | 3.88 | |
| Ala | 112A | O | Ser | 198A | O | 3.49 | * |
| | | | Ser | 198A | OG | 3.98 | * |
| | | | Val | 197A | CG1 | 3.35 | |
| | | | Leu | 196A | O | 3.97 | * |
| | | | Val | 197A | CA | 3.37 | |
| | | | Val | 197A | CB | 3.96 | |
| | | | Val | 197A | C | 3.68 | |
| | | | Ser | 198A | N | 3.02 | *** |
| Gln | 113A | CA | Ser | 198A | O | 3.14 | |
| | | | Ser | 198A | OG | 3.67 | |
| Gln | 113A | CB | Ser | 198A | O | 3.95 | |
| | | | Ser | 198A | OG | 3.66 | |
| Gln | 113A | CG | Ser | 198A | O | 3.68 | |
| | | | Thr | 200A | CG2 | 3.61 | |
| | | | Ser | 198A | OG | 3.44 | |
| Gln | 113A | CD | Ser | 198A | OG | 3.64 | |
| Gln | 113A | NE2 | Ser | 198A | OG | 3.00 | *** |
| Gln | 113A | C | Ser | 198A | O | 3.27 | |
| Leu | 114A | N | Ser | 198A | O | 2.47 | *** |
| | | | Ser | 198A | C | 3.65 | |
| Leu | 114A | CA | Ser | 198A | O | 3.38 | |
| Leu | 114A | CB | Val | 199A | CG1 | 3.86 | |
| Leu | 114A | CG | Thr | 200A | CG2 | 3.13 | |
| Leu | 114A | CD1 | Thr | 200A | CG2 | 3.73 | |
| Leu | 114A | CD2 | Thr | 200A | CG2 | 3.76 | |
| Asp | 193A | OD2 | Pro | 194A | CG | 3.87 | |
| Pro | 194A | CG | Asp | 193A | OD2 | 3.87 | |
| Leu | 195A | CD1 | Leu | 196A | O | 3.60 | |
| | | | Leu | 196A | N | 3.81 | |
| Leu | 196A | N | Leu | 195A | CD1 | 3.81 | |
| Leu | 196A | CB | Leu | 110A | O | 3.84 | |
| Leu | 196A | CG | Ser | 111A | CB | 3.59 | |
| Leu | 196A | CD2 | Ser | 111A | CB | 3.65 | |
| Leu | 196A | C | Ser | 111A | CB | 3.97 | |
| Leu | 196A | O | Ala | 112A | O | 3.97 | * |
| | | | Ala | 112A | CB | 3.88 | |
| | | | Ser | 111A | CA | 3.38 | |
| | | | Ser | 111A | CB | 3.53 | |
| | | | Ser | 111A | C | 3.64 | |
| | | | Ala | 112A | N | 2.90 | *** |
| | | | Ala | 112A | CA | 3.89 | |
| | | | Leu | 195A | CD1 | 3.60 | |
| Val | 197A | CA | Ala | 112A | O | 3.37 | |
| Val | 197A | CB | Ala | 112A | O | 3.96 | |
| Val | 197A | CG1 | Ala | 112A | O | 3.35 | |
| Val | 197A | C | Ala | 112A | O | 3.68 | |
| Ser | 198A | N | Ala | 112A | O | 3.02 | *** |
| Ser | 198A | CB | Ser | 111A | OG | 3.92 | |
| Ser | 198A | OG | Gln | 113A | CG | 3.44 | |
| | | | Gln | 113A | CA | 3.67 | |
| | | | Gln | 113A | CB | 3.66 | |
| | | | Gln | 113A | NE2 | 3.00 | *** |
| | | | Ala | 112A | O | 3.98 | * |
| | | | Gln | 113A | CD | 3.64 | |
| | | | Ser | 111A | OG | 3.24 | *** |
| Ser | 198A | C | Leu | 114A | N | 3.65 | |
| Ser | 198A | O | Gln | 113A | CG | 3.68 | |
| | | | Gln | 113A | CA | 3.14 | |
| | | | Gln | 113A | CB | 3.95 | |
| | | | Gln | 113A | C | 3.27 | |
| | | | Leu | 114A | N | 2.47 | *** |
| | | | Leu | 114A | CA | 3.38 | |
| | | | Ala | 112A | O | 3.49 | * |
| Val | 199A | CG1 | Leu | 114A | CB | 3.86 | |
| Thr | 200A | CG2 | Leu | 114A | CD2 | 3.76 | |
| | | | Gln | 113A | CG | 3.61 | |
| | | | Leu | 114A | CG | 3.13 | |
| | | | Leu | 114A | CD1 | 3.73 | |

Example 3

Generation of Murine Anti-KIR Antibodies

This Example describes the production and identification of anti-KIR antibodies which (1) do not interfere with HLA-C binding and (2) are capable of enhancing NK-cell cytotoxicity.

Immunization and Fusion

Normal RBF-mice were immunized three times by standard methods with 20 μg soluble KIR2DL1 protein, corresponding to the complete extracellular domain of KIR2DL1 (SEQ ID NO:14), produced in *E. coli* and refolded in vitro. Mice were boosted with 20 μg of soluble KIR2DL1 by intravenous injection, and sacrificed after three days. The spleen was removed aseptically and dispersed to a single cell suspension. Fusion of spleen cells and FOX-NY myeloma cells was performed by the electrofusion method. Cells were seeded in microtiter plates and cultured at 37° C., 5% CO2. The tissue-culture medium, containing AAT for selection, was changed three times over a two-week period.

In order to generate a monoclonal and stable hybridoma, cells were sub-cloned using limited dilution method. Cells were seeded into a 96 well plates at a density of one cell/well. After two weeks, supernatants from each well were screened in an indirect ELISA and tested for competition with 1-7F9 (see below). Cells from positive wells were then transferred to a larger culture volume, expanded and sub-cloned again until a stable and monoclonal cell line was obtained (with sub-clones identified by adding -A1, -A2, -A3, -A4 etc. to the name of the parent clone). Similar or additional tests were then performed on the subclones, as well as sequencing of monoclonal antibodies produced by selected subclones.

Primary Screening of Hybridomas

Figure 5:
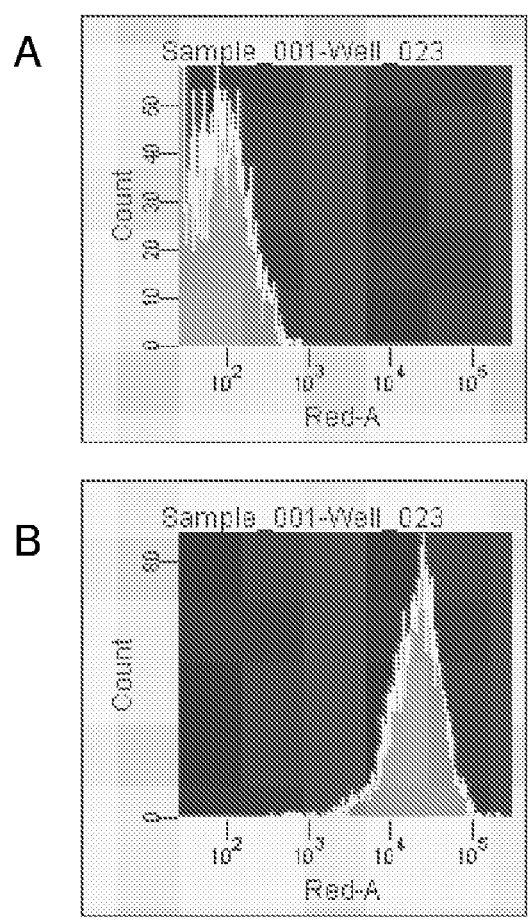
FIG. 5 shows primary screening of KIR-specific monoclonal antibodies (mAbs) by flow-cytometry. YTS (A) and YTS-2DL1 (B) cells were incubated with tissue-culture supernatants from hybridomas derived from KIR2DL1-immunized mice. Ab-binding was detected with APC-conjugated secondary Ab-fragments specific for mouse IgG, which was visualized by flow-cytometry (FACSarray). Histograms depict specific binding of anti-KIR antibody from the 1-26F117 hybridoma to KIR2DL1-expressing YTS-2DL1 cells, but not to KIR2DL1-negative YTS cells.

Hybridomas derived from KIR2DL1-immunized RBF-mice were screened for production of KIR2DL 1-specific mAb's, by testing supernatants for recognition of KIR2DL1-positive cells by flow-cytometry. Tissue-culture supernatants were incubated with YTS (KIR2DL 1-negative) and YTS-2DL1 (KIR2DL1-positive) in a 1:2 dilution. After incubation on ice for one hour, cells were washed with DMEM/2% FCS, and incubated with APC conjugated donkey anti-mouse secondary Ab-fragments, for 30' on ice. After extensive washing with PBS, Ab-binding to living cells was analyzed using a FACSarray (BD Biosciences). MAb's were designated 'KIR2DL1-positive' when mouse mAb's in the hybridoma tissue-culture supernatants bound YTS-2DL1, but not YTS cells (see FIG. 5).

In addition, the tissue-culture supernatants were tested for KIR2DL1 and -3 cross-reactive (or "panKIR") mAbs in an indirect ELISA-assay, by testing recognition of the extracellular domains of KIR2DL1 and -3. For this, Nunc immunoplates were coated with 0.5 μg/ml of goat anti-mouse IgG-specific Ab's (Caltech, Ca) in PBS and incubated overnight at 4° C. Plates were blocked with PBS with 0.05% Tween-20 for 15 min and were washed with PBS/0.05% Tween-20. Culture supernatants from the hybridoma cells were added and the plates were incubated for 1 hour at room temperature. After another wash, soluble biotinylated KIR2DL1 or KIR2DL3 was added at a concentration of 1 μg/ml, and incubated for one hour. After washing, 100 μl of a Streptavidin-HRPO solution was added. After another hour of incubation, plates were washed and developed with TMB-substate (Kem-EN-Tec), as described by the manufacturer. Absorbance at 450 nm was measured on an ELISA-reader, which was directly coupled to 96-wells plates.

From the primary screening, clones were identified as producing cross-reactive mAbs, including a clone designated 1-26F117. These were further tested in BiaCore assays, NK-cytotoxicity assays and KIR-ligand binding-assays (see below).

Example 4

Competition with 1-7F9 for Binding to KIR2DL1 and -3

To determine whether selected mouse cross-reactive mAb's bound KIR2DL1 and -3 on epitopes different from the human mAb 1-7F9, their capacity to compete the binding of 1-7F9 to KIR2DL1 and/or -3 was measured by surface plasmon resonance analysis. This was performed on a Biacore 3000 instrument (Biacore AB, Uppsala, Sweden). Identical amounts of purified 1-7F9 were immobilized in all four flow-cells on a CM5 sensorchip (Biacore AB, Uppsala, Sweden) using standard amine-coupling kit (Biacore AB). Purified recombinant KIR2DL3 in HBS-EP buffer (10 mM HEPES, 150 mM NaCl, 3 mM EDTA, 0.005% Polysorbat 20 (v/v)) was injected in a concentration of 10 µg/ml into flow-cell 1 and 3, for one minute at a flow rate of 10 µl/min. Subsequently, purified recombinant KIR2DL1 in HBS-EP buffer was injected in a concentration of 10 µg/ml into flow-cell 2 and 4, for one minute at flow rate 10 µl/min. Following injection of KIR2DL1 and KIR2DL3, the first sample of hybridoma tissue-culture supernatant diluted 1:1.5 in HBS-EP buffer was injected into flow-cell 1 and 2, for one minute at a flow rate of 10 µl/min. Subsequently, the second sample was injected into flow-cell 3 and 4 under similar conditions. Samples were scored positive for binding when RU response>20. Finally, regeneration of the sensor-chip was performed by injection of 10 mM glycine-HCl pH 1.8, for 15 seconds, at a flow rate of 30 µl/min.

In the assay, 1-26F117 was found not to compete with 1-7F9 for binding to KIR2DL1 and -3, indicating that this antibody bind KIR-molecules at an epitope distinct from that of 1-7F9.

Example 5

NK-Cytotoxicity Assays

The capacity of selected cross-reactive mAbs to inhibit the function of KIR was tested in NK-cytotoxicity assays. YTS-2DL1 cells were pre-incubated with tissue-culture supernatants from hybridomas producing selected mAbs, for 30 min in a 1:2 dilution. Subsequently, $^{51}$Cr-labelled LCL 721.221-Cw4 cells, expressing the KIR2DL1-ligand HLA-Cw4, were added at an E:T-ratio of 6:1. After incubation for 4 hours at 37° C. in a humified $CO_2$-incubator, the release of $^{51}$Cr into the tissue-culture medium was measured in a γ-radiation counter. Specific killing of target-cells in a sample was determined by calculating the percentage of $^{51}$Cr measured in the tissue-culture medium compared to the maximal $^{51}$Cr release from Triton X-100 lysed cells. Samples were analyzed in triplicates.

Figure 6:
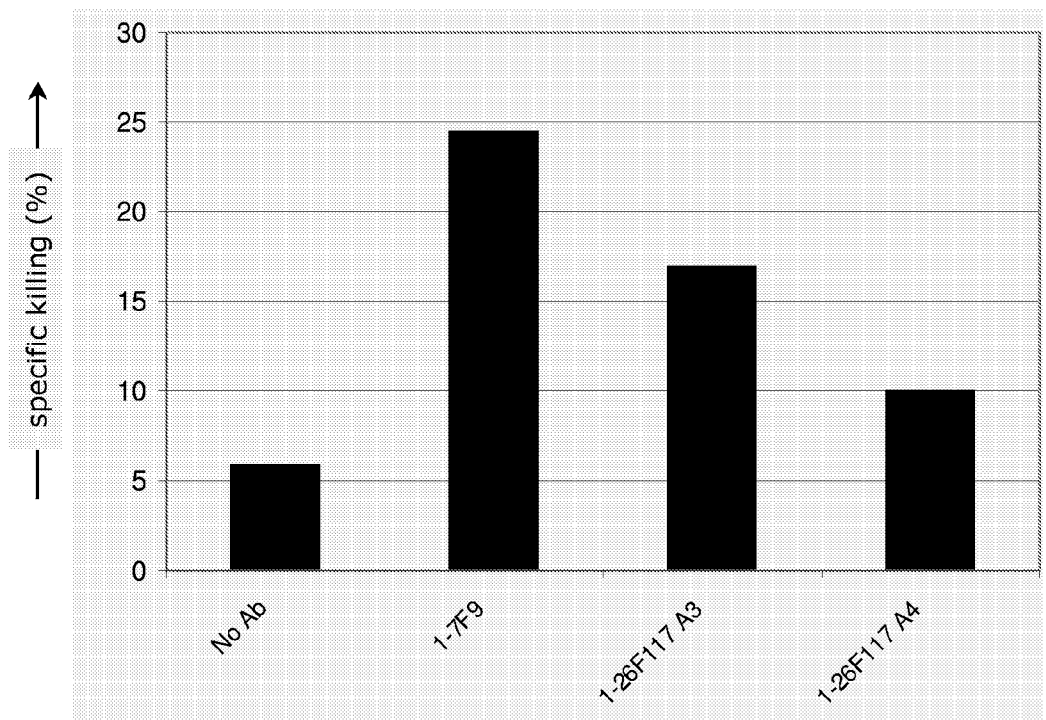
FIG. 6 shows lysis of LCL 721.221-Cw4 target cells by YTS-2DL1 NK cells in the absence or presence of anti-KIR mAbs, as indicated. KIR2DL1-specific YTS-2DL1 cells were pre-incubated with tissue-culture supernatants from selected sub-cloned hybridomas producing mAbs recognizing at least KIR2DL1 and -3. The capacity of these cells to kill $^{51}$Cr-labelled LCL 721.221-Cw4 cells was then measured in a $^{51}$Cr-release cytotoxicity assay (E:T ratio=6:1). In the absence of anti-KIR antibodies, ~5% of target cells were killed, whereas the cross-reactive human mAb 1-7F9 induced about 25% specific killing. Newly identified cross-reactive mAbs 1-26F117-A3 and -A4 specifically induced killing, showing that these are KIR-inhibitory mAbs, capable of reducing inhibition of KIR-mediated NK cell cytotoxicity.

In the presence of the reference mAb, 1-7F9 (20 µg/ml), YTS-2DL1 killed 24% of LCL 721.221-Cw4 cells in this assay, compared to ~5% in the absence of any anti-KIR mAb. Murine test mAbs were designated KIR-blocking when they could induce killing of target-cells at least 1.5-fold of killing in the absence of mAbs, i.e., when killing in the absence of a mAb is normalized to 1, killing in the presence of a KIR-blocking mAb is at least 1.5. As shown in FIG. 6, antibody 1-26F117 induced killing of LCL 721.221-Cw4 cells by YTS-2DL13.7- and near 2-fold over killing in the absence of mAb's, for 1-26F117-A3 and 1-26F117-A4, respectively.

Example 6

KIR2DL1-Fc Ligand-Binding Competition Assays

To determine whether the anti-KIR mAbs that blocked KIR signaling (as determined in Example 5), such as 1-26F117-A3 and 1-26F117-A4, could induce NK-lysis by preventing binding of KIR to its HLA-ligand, the capacity of these mAbs to prevent the interaction between KIR2DL1 and HLA-Cw4 was measured. For this, soluble KIR2DL1-Fc protein was produced as described (Wagtmann et al., Immunity 1995; 3(6):801-9), except that the human Fc was replaced with murine IgG1 Fc. Soluble KIR-Fc binds to cells expressing the specific HLA-C allotypes that are recognized by KIR2DL1, and this binding can be visualized by flow-cytometry using a secondary fluorochrome-conjugated Ab specific for the murine Fc part of the KIR-Fc protein. For example, KIR2DL1-Fc binds to cells transfected with HLA-Cw*0402 (LCL 721.221-Cw4 transfectants) (Litwin et al., J Exp Med. 1993; 178:1321-36) but not to untransfected LCL 721.221 cells.

KIR2DL1-Fc was pre-incubated with 1-26F117-A3 or 1-26F117-A4 hybridoma supernatant in similar amounts used to induce NK-lysis, for 30', on ice. Subsequently, 0.5× $10^4$ LCL 721.221-Cw4 cells were added to the incubation mixture in DMEM/2% FCS, which was further incubated for 60', on ice. After washing in DMEM/2% FCS, reaction-mixtures were incubated with a 1:1 mixture of secondary Ab-fragments against mouse-IgG (PE-conjugated) and against human IgG (APC-conjugated). After incubation on ice for 30', cells were washed several times with PBS, and binding of KIR2DL1-hFc and anti-KIR mAbs analyzed by flow-cytometry (FACSarray).

In this assay, mAbs 1-26F117-A3 and 1-26F117-A4 did not prevent the interaction between KIR2DL1-hFc and LCL 721.221-Cw4 cells, showing that 1-26F117-A3 and -A4 block KIR-signaling without preventing KIR binding to HLA-ligands. This was underscored by the fact that 1-26F117-A3 and 1-26F117-A4 bound via KIR2DL1-hFc to LCL 721.221-Cw4 cells, resulting in double positive stained cells in the FACS dot-plots (see FIG. 7B). As a control, in the same type of assay performed with different concentrations of the known mAb DF200, KIR2DL1-hFc was prevented from binding to LCL 721.221-Cw4 cells in a DF200 dose-dependent fashion, but not when KIR2DL1-hFc was pre-incubated with the known KIR2DL2-specific mAb GL183 (FIG. 7A).

Figure 8:
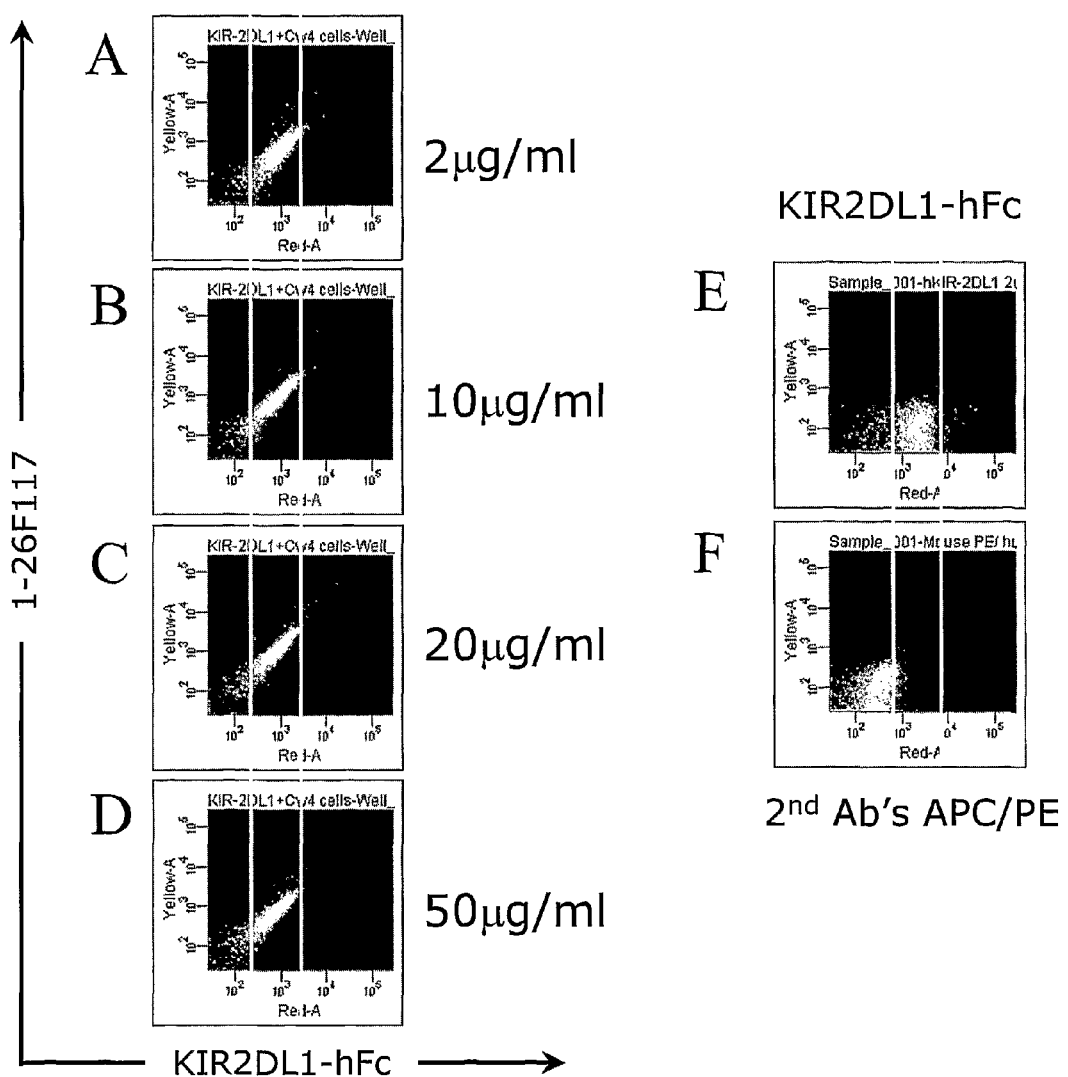
FIG. 8 shows the results of a similar experiment as in FIG. 7, with increasing concentrations of purified 1-26F117. The results confirm that the antibodies produced by clone 1-26F117 did not affect KIR/HLA-Cw4 interactions. (A) 2 µg/ml. (B) 10 µg/ml. (C) 20 µg/ml. (D) 50 µg/ml. (E) Binding of KIR2DL1-hFc in the absence of MAb's (control). (F) Background binding of secondary antibodies in the absence of KIR2DL1-hFc and primary mAbs.

In a similar assay, in which KIR2DL1-hFc was pre-incubated with different concentrations (2-50 µg/ml) of purified 1-26F117, it was confirmed that this clone did not produce antibodies preventing KIR2DL1 binding to HLA-Cw4 (see FIG. 8). Thus, the 1-26F117 clone produces antibodies blocking KIR-signaling without affecting KIR-ligand interactions.

Example 7

KIR2DL1-Fc Ligand-Binding Competition Assay

The capacity of anti-KIR mAbs 1-7F9, 1-4F1, and DF200 to block the interaction between HLA-C and KIR-molecules was assessed by competing the binding of soluble, recombinant KIR-Fc fusion proteins to cells expressing HLA-C.

To test whether anti-KIR mAbs could prevent this interaction between KIR2DL1-Fc and HLA-Cw4, KIR2DL1-Fc proteins were pre-incubated with increasing concentrations of anti-KIR mAbs, and then added to LCL 721.221-Cw4 cells, incubated at 4° C., washed, incubated with an APC-conjugated anti-murine IgG1 Fc, washed, and analyzed by flow cytometry on a FACScalibur, or a FACScanto (Beckton Dickinson), by standard methods.

DF200, 1-7F9 and 1-4F1 prevented the binding of KIR2DL1-Fc to the cells expressing HLA-Cw4, showing that these mAbs block the interaction between KIR2DL1 and HLACw4.

Example 8

Testing of Domain-1 or -2 Binding

This Example describes how to determine whether selected antibodies or other agents bind to Domain 1 or Domain 2 of a KIR.

The binding of anti-KIR antibodies or other agent to a recombinant, truncated form of KIR, consisting of the extracellular Domain 2 of KIR linked to an Fc-fragment, is measured. This construct is made by deleting the nucleotides encoding Domain 1 from the construct encoding KIR2DL1-Fc, transfecting the resulting construct (designated KIR2DL1-D2-Fc) into COS cells or HEK293, and purifying the KIR2DL1-D2-Fc protein on Protein A, as described for the intact KIR2DL1-Fc (see Examples 6 and 7, and Wagtmann et al. 1995, supra).

The binding of anti-KIR agents to purified KIR2DL1-D2-Fc is measured by surface plasmon resonance analysis. This is performed on a Biacore 3000 instrument (Biacore AB, Uppsala, Sweden). Identical amounts of purified KIR2DL1-D2-Fc are immobilized in all four flow-cells on a CM5 sensorchip (Biacore AB, Uppsala, Sweden) using standard amine-coupling kit (Biacore AB). Purified recombinant KIR2DL1-D2-Fc in HBS-EP buffer (10 mM HEPES, 150 mM NaCl, 3 mM EDTA, 0.005% Polysorbat 20 (v/v)) is injected in a concentration of 10 µg/ml into the flow-cells, for one minute at a flow rate of 10 µl/min. Following injection of KIR2DL1-D2-Fc, hybridoma tissue-culture supernatants diluted 1:1.5 in HBS-EP buffer are injected into separate flow-cells, for one minute at a flow rate of 10 µl/min. Samples are scored positive for binding when RU response>20. Finally, regeneration of the sensor-chip is performed by injection of 10 mM glycine-HCl pH 1.8, for 15 seconds, at a flow rate of 30 µl/min. Hybridoma supernatants that do bind to KIR2DL1-D2-Fc are thereby shown to contain mAbs that bind to Domain 2 of KIR, whereas those that don't are designated as containing mAbs that either bind Domain 1 or that bind to complex epitopes spanning both Domain 1 and Domain 2.

A similar assay can be made using a KIR2DL1-D1-Fc construct to determine whether anti-KIR antibodies or other KIR-binding agents bind Domain 1.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. An isolated monoclonal antibody or antigen binding fragment thereof that binds to an extracellular portion of an inhibitory human Killer IgG-like Receptor 2DL polypeptide KIR2DL1, KIR2DL2 and/or KIR2DL3, wherein the isolated monoclonal antibody or antigen binding fragment thereof:
   (i) reduces KIR2DL1, KIR2DL2 and/or KIR2DL3-mediated inhibition of NK cell cytotoxicity, and
   (ii) does not detectably reduce binding between said KIR2DL1, KIR2DL2 and/or KIR2DL3 and an HLA class I ligand of said KIR2DL1, KIR2DL2 and/or KIR2DL3.

2. The isolated antibody or antigen binding fragment thereof of claim 1, wherein the isolated antibody or antigen binding fragment thereof is a Fab fragment, a Fab' fragment, a Fab'-SH fragment, a F(ab')2 fragment, or a multispecific antibody.

3. The isolated antibody or antigen binding fragment thereof of claim 1, wherein the isolated antibody or antigen binding fragment thereof is a cross-reactive anti-KIR antibody or an antigen binding fragment thereof.

4. The isolated antibody or antigen binding fragment thereof of claim 3, wherein the isolated antibody or antigen binding fragment thereof binds to each of KIR2DL1 and KIR2DL3.

5. The isolated antibody or antigen binding fragment thereof of claim 4, wherein the isolated antibody or antigen binding fragment thereof competes with an antibody comprising a VH polypeptide having the amino acid sequence set forth in SEQ ID NO:17 and a VL polypeptide having the amino acid sequence set forth in SEQ ID NO:18 for binding to at least one of KIR2DL1 and KIR2DL3.

6. The isolated antibody or antigen binding fragment thereof of claim 5, wherein the isolated antibody or antigen binding fragment thereof comprises the same six complementarity determining regions (CDR's) as an antibody that comprises the VH and VL polypeptides in SEQ ID NO:17 and SEQ ID NO:18.

7. A pharmaceutical composition comprising the isolated antibody or antigen binding fragment thereof according to claim 1 in an amount effective to detectably potentiate NK cell cytotoxicity in a patient, and one or more pharmaceutically acceptable carriers or diluents.

8. The pharmaceutical formulation of claim 7, further comprising a therapeutic agent selected from an immunomodulatory agent, a hormonal agent, a chemotherapeutic agent, an anti-angiogenic agent, an apoptotic agent, and an antibody that blocks HLA-binding to an inhibitory KIR receptor.

9. The pharmaceutical composition of claim 7, wherein the isolated antibody or antigen binding fragment thereof is a cross-reactive anti-KIR2DL antibody or a fragment thereof.

10. The pharmaceutical composition of claim 9, wherein the isolated antibody or antigen binding fragment thereof binds to each of KIR2DL1 and KIR2DL3.

11. The pharmaceutical composition of claim 9, wherein the isolated antibody or antigen binding fragment is an antibody or antibody fragment that competes with an antibody comprising variable regions having the amino acid sequences set forth in SEQ ID NO:17 and SEQ ID NO:18 for binding to at least one of KIR2DL1 and KIR2DL3.

12. The pharmaceutical composition of claim 9, wherein the isolated antibody or antigen binding fragment is an antibody or antibody fragment comprising variable regions having the amino acid sequences set forth in SEQ ID NO:17 and SEQ ID NO:18.

13. An isolated human, chimeric or humanized antibody or antigen binding fragment thereof according to claim 1, wherein said isolated antibody or antigen binding fragment thereof is an isolated antibody or antigen binding fragment that competes with an antibody comprising variable regions having the amino acid sequences set forth in SEQ ID NO:17 and SEQ ID NO:18 for binding to at least one of KIR2DL1 and KIR2DL3.

14. The isolated chimeric or humanized or antigen binding fragment thereof according to claim 13, wherein said isolated chimeric or humanized or antigen binding fragment is an antibody or antigen binding fragment comprising the CDR H1 region corresponding to residues 31-35 of SEQ ID NO:17, the CDR H2 corresponding to residues 50-66 of SEQ ID NO:17, the CDR H3 corresponding to residues 99-108 of SEQ ID NO:17; the CDR L1 corresponding to residues 24-34 of SEQ ID NO:18; the CDR L2 corresponding to residues 50-56 of SEQ ID NO:18, and the CDR L3 corresponding to residues 89-97 of SEQ ID NO:18.

15. An isolated human, chimeric or humanized antibody or antigen binding fragment thereof that binds to an extracellular portion of an inhibitory human Killer IgG-like Receptor 2DL polypeptide KIR2DL1, KIR2DL2 and/or KIR2DL3, wherein the isolated human, chimeric or humanized antibody or antigen binding fragment thereof:
   (i) reduces KIR2DL1, KIR2DL2 and/or KIR2DL3-mediated inhibition of NK cell cytotoxicity, and
   (ii) does not detectably reduce binding been replaced with between said KIR2DL1, KIR2DL2 and/or KIR2DL3 and an HLA class I ligand of said KIR2DL1, KIR2DL2 and/or KIR2DL3.

16. The isolated human, chimeric or humanized antibody or antigen binding fragment thereof of claim 15, wherein the isolated human, chimeric or humanized antibody or antigen binding fragment thereof is a Fab fragment, a Fab' fragment, a Fab'-SH fragment, a F(ab')2 fragment, or a multispecific antibody.

17. The isolated human, chimeric or humanized antibody or antigen binding fragment thereof of claim 15, wherein the isolated human, chimeric or humanized antibody or antigen binding fragment thereof is a cross-reactive anti-KM antibody or an antigen binding fragment thereof.

18. The isolated human, chimeric or humanized antibody or antigen binding fragment of claim 17, wherein the isolated human, chimeric or humanized antibody or antigen binding fragment thereof binds to each of KIR2DL1 and KIR2DL3.

19. The isolated human, chimeric or humanized antibody or antigen binding fragment thereof of claim 18, wherein the isolated human, chimeric or humanized antibody or antigen binding fragment thereof competes with an antibody comprising the a VH polypeptide having the amino acid sequence set forth in SEQ ID NO:17 and a VL polypeptide having the amino acid sequence set forth in SEQ ID NO:18 for binding to at least one of KIR2DL1 and KIR2DL3.

20. The isolated chimeric or humanized antibody or antigen binding fragment thereof of claim 19, wherein the isolated chimeric or humanized, chimeric or humanized antibody or antigen binding fragment thereof, comprises a VH polypeptide having the amino acid sequence set forth in SEQ ID NO:17 and a VL polypeptide having the amino acid sequence set forth in SEQ ID NO:18.

21. The isolated chimeric or humanized antibody or antigen binding fragment thereof of claim 19, wherein the isolated chimeric or humanized antibody or antigen binding fragment thereof comprises the same six complementarity determining regions (CDR's) as an antibody that comprises the VH and VL polypeptides in SEQ ID NO:17 and SEQ ID NO:18.

22. A pharmaceutical composition comprising the isolated human, chimeric or humanized antibody or antigen binding fragment thereof according to claim 15 in an amount effective to detectably potentiate NK cell cytotoxicity in a patient, and one or more pharmaceutically acceptable carriers or diluents.

23. The pharmaceutical formulation of claim 22, further comprising a therapeutic agent selected from an immunomodulatory agent, a hormonal agent, a chemotherapeutic agent, an anti-angiogenic agent, an apoptotic agent, and an antibody that blocks HLA-binding to an inhibitory KIR receptor.

24. The pharmaceutical composition of claim 22, wherein the isolated human, chimeric or humanized antibody or antigen binding fragment thereof is a cross-reactive anti-KIR2DL antibody or a fragment thereof.

25. The pharmaceutical composition of claim 24, wherein the isolated human, chimeric or humanized antibody or antigen binding fragment thereof binds to each of KIR2DL1 and KIR2DL3.

26. The pharmaceutical composition of claim 24, wherein the isolated human, chimeric or humanized antibody or antigen binding fragment is an antibody or antibody fragment competing with an antibody comprising variable regions having the amino acid sequences set forth in SEQ ID NO:17 and SEQ ID NO:18 for binding to at least one of KIR2DL1 and KIR2DL3.

27. The pharmaceutical composition of claim 24, wherein the isolated chimeric or humanized antibody or antigen binding fragment is an antibody or antibody fragment comprising variable regions having the amino acid sequences set forth in SEQ ID NO:17 and SEQ ID NO:18.

28. An isolated antibody or antigen binding fragment thereof according to claim 15, wherein said isolated human, chimeric or humanized antibody or antigen binding fragment thereof is an isolated antibody or antigen binding fragment competes with an antibody comprising variable regions having the amino acid sequences set forth in SEQ ID NO:17 and SEQ ID NO:18 for binding to at least one of KIR2DL1 and KIR2DL3.

29. The isolated, chimeric or humanized antibody or antigen binding fragment thereof according to claim 28, wherein said isolated chimeric or humanized antibody or antigen binding fragment is an antibody or antigen binding fragment comprising the CDR H1 region corresponding to residues 31-35 of SEQ ID NO:17, the CDR H2 corresponding to residues 50-66 of SEQ ID NO:17, the CDR H3 corresponding to residues 99-108 of SEQ ID NO:17; the CDR L1 corresponding to residues 24-34 of SEQ ID NO:18; the CDR L2 corresponding to residues 50-56 of SEQ ID NO:18, and the CDR L3 corresponding to residues 89-97 of SEQ ID NO:18.

30. The isolated chimeric or humanized antibody or antigen binding fragment thereof according to claim 29, wherein said isolated chimeric or humanized antibody or antigen binding fragment is an antibody or antigen binding fragment comprising variable regions having the amino acid sequences set forth in SEQ ID NO:17 and SEQ ID NO:18.

* * * * *

UNITED STATES PATENT AND TRADEMARK OFFICE
CERTIFICATE OF CORRECTION

PATENT NO. : 8,222,376 B2  
APPLICATION NO. : 11/813402  
DATED : July 17, 2012  
INVENTOR(S) : Soren Berg Padkaer It is certified that error appears in the above-identified patent and that said Letters Patent is hereby corrected as shown below:

Title Page, item (57);

Col. 2 (Abstract) line 5 of Abstract, after "signaling via KIR," delete "5".

In the Claims:

Col. 100, claim 15, line 53, after "binding" delete "been replaced with".

Col. 100, claim 17, line 66, delete "anti-KM" and insert -- anti-KIR --, therefor.

Col. 101, claim 19, line 9, delete "the a" and insert -- the --, therefor.

Signed and Sealed this  
Fourteenth Day of May, 2013

Teresa Stanek Rea  
*Acting Director of the United States Patent and Trademark Office*

SEQUENCE LISTING

```
<160> NUMBER OF SEQ ID NOS: 25

<210> SEQ ID NO 1
<211> LENGTH: 348
<212> TYPE: PRT
<213> ORGANISM: Homo sapiens

<400> SEQUENCE: 1
```

Met Ser Leu Leu Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Met Phe Asn Asp Thr Leu Arg Leu Ile Gly Glu His His Asp Gly Val
65                  70                  75                  80

Ser Lys Ala Asn Phe Ser Ile Ser Arg Met Thr Gln Asp Leu Ala Gly
                85                  90                  95

Thr Tyr Arg Cys Tyr Gly Ser Val Thr His Ser Pro Tyr Gln Val Ser
            100                 105                 110

Ala Pro Ser Asp Pro Leu Asp Ile Val Ile Gly Leu Tyr Glu Lys
        115                 120                 125

Pro Ser Leu Ser Ala Gln Pro Gly Pro Thr Val Leu Ala Gly Glu Asn
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe His Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Ile Leu Ile Gly Thr Ser Val Val Ile Ile Leu
                245                 250                 255

Phe Ile Leu Leu Phe Phe Leu Leu His Arg Trp Cys Ser Asn Lys Lys
            260                 265                 270

Asn Ala Ala Val Met Asp Gln Glu Ser Ala Gly Asn Arg Thr Ala Asn
        275                 280                 285

Ser Glu Asp Ser Asp Glu Gln Asp Pro Gln Glu Val Thr Tyr Thr Gln
    290                 295                 300

Leu Asn His Cys Val Phe Thr Gln Arg Lys Ile Thr Arg Pro Ser Gln
305                 310                 315                 320

Arg Pro Lys Thr Pro Pro Thr Asp Ile Ile Val Tyr Thr Glu Leu Pro
                325                 330                 335

Asn Ala Glu Ser Arg Ser Lys Val Val Ser Cys Pro
        340                 345

<210> SEQ ID NO 2
<211> LENGTH: 348
<212> TYPE: PRT
<213> ORGANISM: Homo sapiens

<400> SEQUENCE: 2

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

```
Ala His Pro Gly Arg Leu Val Lys Ser Glu Glu Thr Val Ile Leu Gln
         35                  40                  45

Cys Trp Ser Asp Val Arg Phe Glu His Phe Leu Leu His Arg Glu Gly
 50                  55                  60

Lys Phe Lys Asp Thr Leu His Leu Ile Gly Glu His His Asp Gly Val
 65                  70                  75                  80

Ser Lys Ala Asn Phe Ser Ile Gly Pro Met Met Gln Asp Leu Ala Gly
             85                  90                  95

Thr Tyr Arg Cys Tyr Gly Ser Val Thr His Ser Pro Tyr Gln Leu Ser
        100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Cys Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Ile Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Ile Leu Ile Gly Thr Ser Val Val Ile Ile Leu
                245                 250                 255

Phe Ile Leu Leu Phe Phe Leu Leu His Arg Trp Cys Ser Asn Lys Lys
            260                 265                 270

Asn Ala Ala Val Met Asp Gln Glu Ser Ala Gly Asn Arg Thr Ala Asn
        275                 280                 285

Ser Glu Asp Ser Asp Glu Gln Asp Pro Gln Glu Val Thr Tyr Thr Gln
    290                 295                 300

Leu Asn His Cys Val Phe Thr Gln Arg Lys Ile Thr Arg Pro Ser Gln
305                 310                 315                 320

Arg Pro Lys Thr Pro Pro Thr Asp Ile Ile Val Tyr Ala Glu Leu Pro
                325                 330                 335

Asn Ala Glu Ser Arg Ser Lys Val Val Ser Cys Pro
            340                 345

<210> SEQ ID NO 3
<211> LENGTH: 341
<212> TYPE: PRT
<213> ORGANISM: Homo sapiens

<400> SEQUENCE: 3

Met Ser Leu Met Val Val Ser Met Val Cys Val Gly Phe Phe Leu Leu
 1               5                  10                  15

Gln Gly Ala Trp Pro His Glu Gly Val His Arg Lys Pro Ser Leu Leu
             20                  25                  30

Ala His Pro Gly Pro Leu Val Lys Ser Glu Glu Thr Val Ile Leu Gln
         35                  40                  45

Cys Trp Ser Asp Val Arg Phe Gln His Phe Leu Leu His Arg Glu Gly
 50                  55                  60
```

Lys Phe Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Thr Gly Asn Pro
210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Ile Ile Leu
                245                 250                 255

Phe Ile Leu Leu Leu Phe Phe Leu Leu His Arg Trp Cys Cys Asn Lys
            260                 265                 270

Lys Asn Ala Val Val Met Asp Gln Glu Pro Ala Gly Asn Arg Thr Val
        275                 280                 285

Asn Arg Glu Asp Ser Asp Glu Gln Asp Pro Gln Glu Val Thr Tyr Ala
290                 295                 300

Gln Leu Asn His Cys Val Phe Thr Gln Arg Lys Ile Thr Arg Pro Ser
305                 310                 315                 320

Gln Arg Pro Lys Thr Pro Pro Thr Asp Ile Ile Val Tyr Thr Glu Leu
                325                 330                 335

Pro Asn Ala Glu Pro
            340

<210> SEQ ID NO 4
<211> LENGTH: 377
<212> TYPE: PRT
<213> ORGANISM: Homo sapiens

<400> SEQUENCE: 4

Met Ser Met Ser Pro Thr Val Ile Ile Leu Ala Cys Leu Gly Phe Phe
1               5                   10                  15

Leu Asp Gln Ser Val Trp Ala His Val Gly Gly Gln Asp Lys Pro Phe
            20                  25                  30

Cys Ser Ala Trp Pro Ser Ala Val Val Pro Gln Gly Gly His Val Thr
        35                  40                  45

Leu Arg Cys His Tyr Arg Arg Gly Phe Asn Ile Phe Thr Leu Tyr Lys
    50                  55                  60

Lys Asp Gly Val Pro Val Pro Glu Leu Tyr Asn Arg Ile Phe Trp Asn
65                  70                  75                  80

Ser Phe Leu Ile Ser Pro Leu Thr Pro Ala His Ala Gly Thr Tyr Arg
                85                  90                  95

```
Cys Arg Gly Phe His Pro His Ser Pro Thr Glu Trp Ser Ala Pro Ser
            100                 105                 110

Asn Pro Leu Val Ile Met Val Thr Gly Leu Tyr Glu Lys Pro Ser Leu
            115                 120                 125

Thr Ala Arg Pro Gly Pro Thr Val Arg Thr Gly Glu Asn Val Thr Leu
130                 135                 140

Ser Cys Ser Ser Gln Ser Ser Phe Asp Ile Tyr His Leu Ser Arg Glu
145                 150                 155                 160

Gly Glu Ala His Glu Leu Arg Leu Pro Ala Val Pro Ser Ile Asn Gly
                165                 170                 175

Thr Phe Gln Ala Asp Phe Pro Leu Gly Pro Ala Thr His Gly Glu Thr
            180                 185                 190

Tyr Arg Cys Phe Gly Ser Phe His Gly Ser Pro Tyr Glu Trp Ser Asp
            195                 200                 205

Ala Ser Asp Pro Leu Pro Val Ser Val Thr Gly Asn Pro Ser Ser Ser
210                 215                 220

Trp Pro Ser Pro Thr Glu Pro Ser Phe Lys Thr Gly Ile Ala Arg His
225                 230                 235                 240

Leu His Ala Val Ile Arg Tyr Ser Val Ala Ile Ile Leu Phe Thr Ile
                245                 250                 255

Leu Pro Phe Phe Leu Leu His Arg Trp Cys Ser Lys Lys Lys Asp Ala
            260                 265                 270

Ala Val Met Asn Gln Glu Pro Ala Gly His Arg Thr Val Asn Arg Glu
            275                 280                 285

Asp Ser Asp Glu Gln Asp Pro Gln Glu Val Thr Tyr Ala Gln Leu Asp
290                 295                 300

His Cys Ile Phe Thr Gln Arg Lys Ile Thr Gly Pro Ser Gln Arg Ser
305                 310                 315                 320

Lys Arg Pro Ser Thr Asp Thr Ser Val Cys Ile Glu Leu Pro Asn Ala
                325                 330                 335

Glu Pro Arg Ala Leu Ser Pro Ala His Glu His His Ser Gln Ala Leu
            340                 345                 350

Met Gly Ser Ser Arg Glu Thr Thr Ala Leu Ser Gln Thr Gln Leu Ala
            355                 360                 365

Ser Ser His Val Pro Ala Ala Gly Ile
            370                 375

<210> SEQ ID NO 5
<211> LENGTH: 304
<212> TYPE: PRT
<213> ORGANISM: Homo sapiens

<400> SEQUENCE: 5

Met Ser Leu Thr Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Met Phe Glu His Phe Leu Leu His Arg Glu Gly
50                  55                  60

Met Phe Asn Asp Thr Leu Arg Leu Ile Gly Glu His His Asp Gly Val
65                  70                  75                  80

Ser Lys Ala Asn Phe Ser Ile Ser Arg Met Arg Gln Asp Leu Ala Gly
                85                  90                  95
```

-continued

Thr Tyr Arg Cys Tyr Gly Ser Val Thr His Ser Pro Tyr Gln Leu Ser
            100                 105                 110

Ala Pro Ser Asp Pro Leu Asp Ile Val Ile Gly Leu Tyr Glu Lys
        115                 120                 125

Pro Ser Leu Ser Ala Gln Pro Gly Pro Thr Val Leu Ala Gly Glu Asn
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Thr Lys
                165                 170                 175

Val Asn Gly Thr Phe Gln Ala Asn Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Lys Ser Ser Asp Pro Leu Leu Val Ser Val Thr Gly Asn Pro
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asp Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300

<210> SEQ ID NO 6
<211> LENGTH: 304
<212> TYPE: PRT
<213> ORGANISM: Homo sapiens

<400> SEQUENCE: 6

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Arg Phe Glu His Phe Leu Leu His Arg Glu Gly
    50                  55                  60

Lys Tyr Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Phe Ser Ala Gly Pro Lys
                165                 170                 175

```
Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Thr Gly Asn Pro
210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asn Lys
                260                 265                 270

Lys Asn Ala Ala Val Met Asp Gln Glu Pro Ala Gly Asn Arg Thr Val
                275                 280                 285

Asn Ser Glu Asp Ser Asp Glu Gln Asp His Gln Glu Val Ser Tyr Ala
                290                 295                 300

<210> SEQ ID NO 7
<211> LENGTH: 304
<212> TYPE: PRT
<213> ORGANISM: Homo sapiens

<400> SEQUENCE: 7

Met Ser Leu Met Val Ile Ser Met Ala Cys Val Gly Phe Phe Trp Leu
1               5                   10                  15

Gln Gly Ala Trp Pro His Glu Gly Phe Arg Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Thr Phe Asn Asp Thr Leu Arg Leu Ile Gly Glu His Ile Asp Gly Val
65                  70                  75                  80

Ser Lys Ala Asn Phe Ser Ile Gly Arg Met Arg Gln Asp Leu Ala Gly
                85                  90                  95

Thr Tyr Arg Cys Tyr Gly Ser Val Pro His Ser Pro Tyr Gln Phe Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Trp Ser Ser Tyr Asp Met Tyr His Leu
145                 150                 155                 160

Ser Thr Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr Gln
                180                 185                 190

Gly Gly Thr Tyr Arg Cys Phe Gly Ser Phe His Asp Ser Pro Tyr Glu
            195                 200                 205

Trp Ser Lys Ser Ser Asp Pro Leu Leu Val Ser Val Thr Gly Asn Pro
        210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Leu Pro
                245                 250                 255
```

Phe Thr Ile Leu Leu Phe Phe Leu Leu His Arg Trp Cys Ser Asp Lys
            260                 265                 270

Lys Asn Ala Ser Val Met Asp Gln Gly Pro Ala Gly Asn Arg Thr Val
        275                 280                 285

Asn Arg Glu Asp Ser Asp Glu Gln Asp His Gln Glu Val Ser Tyr Ala
    290                 295                 300

<210> SEQ ID NO 8
<211> LENGTH: 304
<212> TYPE: PRT
<213> ORGANISM: Homo sapiens

<400> SEQUENCE: 8

Met Ser Leu Met Val Ile Ile Met Ala Cys Val Gly Phe Phe Leu Leu
1               5                   10                  15

Gln Gly Ala Trp Pro Gln Glu Gly Val His Arg Lys Pro Ser Phe Leu
            20                  25                  30

Ala Leu Pro Gly His Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Lys Phe Asn Asn Thr Leu His Leu Ile Gly Glu His His Asp Gly Val
65                  70                  75                  80

Ser Lys Ala Asn Phe Ser Ile Gly Pro Met Met Pro Val Leu Ala Gly
                85                  90                  95

Thr Tyr Arg Cys Tyr Gly Ser Val Pro His Ser Pro Tyr Gln Leu Ser
            100                 105                 110

Ala Pro Ser Asp Pro Leu Asp Met Val Ile Ile Gly Leu Tyr Glu Lys
        115                 120                 125

Pro Ser Leu Ser Ala Gln Pro Gly Pro Thr Val Gln Ala Gly Glu Asn
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Val Arg Ser
                165                 170                 175

Ile Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ala Pro Tyr Glu
        195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asp Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300

<210> SEQ ID NO 9
<211> LENGTH: 304
<212> TYPE: PRT
<213> ORGANISM: Homo sapiens

<400> SEQUENCE: 9

```
Met Leu Leu Met Val Ile Ser Met Ala Cys Val Ala Phe Phe Leu Leu
1               5                   10                  15

Gln Gly Ala Trp Pro His Glu Gly Phe Arg Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Met Phe Glu His Phe Leu Leu His Arg Glu Gly
    50                  55                  60

Thr Phe Asn His Thr Leu Arg Leu Ile Gly Glu His Ile Asp Gly Val
65                  70                  75                  80

Ser Lys Gly Asn Phe Ser Ile Gly Arg Met Thr Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Pro Ala Gln Pro Gly Pro Thr Val Leu Ala Gly Glu Ser
130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Leu Pro Ala Gly Pro Lys
                165                 170                 175

Val Asn Arg Thr Phe Gln Ala Asp Ser Pro Leu Asp Pro Ala Thr His
            180                 185                 190

Gly Gly Ala Tyr Arg Cys Phe Gly Ser Phe Arg Asp Ser Pro Tyr Glu
        195                 200                 205

Trp Ser Lys Ser Ser Asp Pro Leu Leu Val Ser Val Thr Gly Asn Ser
    210                 215                 220

Ser Asn Ser Trp Pro Ser Pro Thr Glu Pro Ser Ser Glu Thr Gly Asn
225                 230                 235                 240

Pro Arg His Leu His Val Leu Ile Gly Thr Ser Val Val Lys Leu Pro
                245                 250                 255

Phe Thr Ile Leu Leu Phe Phe Leu Leu His Arg Trp Cys Ser Asn Lys
            260                 265                 270

Lys Asn Ala Ser Val Met Asp Gln Gly Pro Ala Gly Asn Arg Thr Val
        275                 280                 285

Asn Arg Glu Asp Ser Asp Glu Gln Asp His Gln Glu Val Ser Tyr Ala
290                 295                 300
```

<210> SEQ ID NO 10
<211> LENGTH: 444
<212> TYPE: PRT
<213> ORGANISM: Homo sapiens

<400> SEQUENCE: 10

```
Met Ser Leu Met Val Val Ser Met Ala Cys Val Gly Leu Phe Leu Val
1               5                   10                  15

Gln Arg Ala Gly Pro His Met Gly Gly Gln Asp Lys Pro Phe Leu Ser
            20                  25                  30

Ala Trp Pro Ser Ala Val Val Pro Arg Gly Gly His Val Thr Leu Arg
        35                  40                  45

Cys His Tyr Arg His Arg Phe Asn Asn Phe Met Leu Tyr Lys Glu Asp
    50                  55                  60
```

```
Arg Ile His Ile Pro Ile Phe His Gly Arg Ile Phe Gln Glu Ser Phe
 65                  70                  75                  80

Asn Met Ser Pro Val Thr Thr Ala His Ala Gly Asn Tyr Thr Cys Arg
                 85                  90                  95

Gly Ser His Pro His Ser Pro Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Val Lys Ser Gly Glu Arg Val Ile Leu Gln Cys
    130                 135                 140

Trp Ser Asp Ile Met Phe Glu His Phe Phe Leu His Lys Glu Gly Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Pro Met Met Leu Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Pro Tyr Glu Lys Pro
    210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
                245                 250                 255

Arg Glu Gly Gly Ala His Glu Arg Arg Leu Pro Ala Val Arg Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg His Ser Pro Tyr Glu Trp
    290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Pro
                325                 330                 335

Arg His Leu His Ile Leu Ile Gly Thr Ser Val Val Ile Ile Leu Phe
            340                 345                 350

Ile Leu Leu Leu Phe Phe Leu Leu His Leu Trp Cys Ser Asn Lys Lys
        355                 360                 365

Asn Ala Ala Val Met Asp Gln Glu Pro Ala Gly Asn Arg Thr Ala Asn
    370                 375                 380

Ser Glu Asp Ser Asp Glu Gln Asp Pro Glu Glu Val Thr Tyr Ala Gln
385                 390                 395                 400

Leu Asp His Cys Val Phe Thr Gln Arg Lys Ile Thr Arg Pro Ser Gln
                405                 410                 415

Arg Pro Lys Thr Pro Pro Thr Asp Thr Ile Leu Tyr Thr Glu Leu Pro
            420                 425                 430

Asn Ala Lys Pro Arg Ser Lys Val Val Ser Cys Pro
        435                 440

<210> SEQ ID NO 11
<211> LENGTH: 455
<212> TYPE: PRT
<213> ORGANISM: Homo sapiens

<400> SEQUENCE: 11
```

```
Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
            35                  40                  45

Cys His Tyr Arg Arg Gly Phe Asn Asn Phe Met Leu Tyr Lys Glu Asp
            50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
            115                 120                 125

His Pro Gly Pro Leu Leu Lys Ser Gly Glu Thr Val Ile Leu Gln Cys
    130                 135                 140

Trp Ser Asp Val Met Phe Glu His Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
            245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
            275                 280                 285

Gly Thr Tyr Arg Cys Phe Gly Ser Phe Arg Ala Leu Pro Cys Val Trp
            290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
            370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430
```

```
Asn Ala Glu Pro Arg Ser Lys Val Val Ser Cys Pro Arg Ala Pro Gln
            435                 440                 445

Ser Gly Leu Glu Gly Val Phe
    450                 455

<210> SEQ ID NO 12
<211> LENGTH: 410
<212> TYPE: PRT
<213> ORGANISM: Homo sapiens

<400> SEQUENCE: 12

Met Ser Leu Met Val Val Ser Met Ala Cys Val Gly Phe Phe Leu Leu
1               5                   10                  15

Glu Gly Pro Trp Pro His Val Gly Gly Gln Asp Lys Pro Phe Leu Ser
                20                  25                  30

Ala Trp Pro Gly Thr Val Val Ser Glu Gly Gln His Val Thr Leu Gln
            35                  40                  45

Cys Arg Ser Arg Leu Gly Phe Asn Glu Phe Ser Leu Ser Lys Glu Asp
    50                  55                  60

Gly Met Pro Val Pro Glu Leu Tyr Asn Arg Ile Phe Arg Asn Ser Phe
65                  70                  75                  80

Leu Met Gly Pro Val Thr Pro Ala His Ala Gly Thr Tyr Arg Cys Cys
                85                  90                  95

Ser Ser His Pro His Ser Pro Thr Gly Trp Ser Ala Pro Ser Asn Pro
                100                 105                 110

Val Val Ile Met Val Thr Gly Val His Arg Lys Pro Ser Leu Leu Ala
                115                 120                 125

His Pro Gly Pro Leu Val Lys Ser Gly Glu Thr Val Ile Leu Gln Cys
130                 135                 140

Trp Ser Asp Val Arg Phe Glu Arg Phe Leu Leu His Arg Glu Gly Ile
145                 150                 155                 160

Thr Glu Asp Pro Leu Arg Leu Ile Gly Gln Leu His Asp Ala Gly Ser
                165                 170                 175

Gln Val Asn Tyr Ser Met Gly Pro Met Thr Pro Ala Leu Ala Gly Thr
                180                 185                 190

Tyr Arg Cys Phe Gly Ser Val Thr His Leu Pro Tyr Glu Leu Ser Ala
                195                 200                 205

Pro Ser Asp Pro Leu Asp Ile Val Val Gly Leu Tyr Gly Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Arg Ser Leu Phe Asp Ile Tyr His Leu Ser
                245                 250                 255

Arg Glu Ala Glu Ala Gly Glu Leu Arg Leu Thr Ala Val Leu Arg Val
                260                 265                 270

Asn Gly Thr Phe Gln Ala Asn Phe Pro Leu Gly Pro Val Thr His Gly
                275                 280                 285

Gly Asn Tyr Arg Cys Phe Gly Ser Phe Arg Ala Leu Pro His Ala Trp
                290                 295                 300

Ser Asp Pro Ser Asp Pro Leu Pro Val Ser Val Thr Gly Asn Ser Arg
305                 310                 315                 320

Tyr Leu His Ala Leu Ile Gly Thr Ser Val Val Ile Ile Pro Phe Ala
                325                 330                 335

Ile Leu Leu Phe Phe Leu Leu His Arg Trp Cys Ala Asn Lys Lys Asn
                340                 345                 350
```

```
Ala Val Val Met Asp Gln Glu Pro Ala Gly Asn Arg Thr Val Asn Arg
            355                 360                 365

Glu Asp Ser Asp Glu Gln Asp Pro Gln Glu Val Thr Tyr Ala Gln Leu
        370                 375                 380

Asn His Cys Val Phe Thr Gln Arg Lys Ile Thr Arg Pro Ser Gln Arg
385                 390                 395                 400

Pro Lys Thr Pro Pro Thr Asp Thr Ser Val
            405                 410

<210> SEQ ID NO 13
<211> LENGTH: 387
<212> TYPE: PRT
<213> ORGANISM: Homo sapiens

<400> SEQUENCE: 13

Met Ser Leu Met Val Ser Met Ala Cys Val Gly Leu Phe Leu Val
1               5                   10                  15

Gln Arg Ala Gly Pro His Met Gly Gly Gln Asp Lys Pro Phe Leu Ser
            20                  25                  30

Ala Trp Pro Ser Ala Val Val Pro Arg Gly Gly His Val Thr Leu Arg
            35                  40                  45

Cys His Tyr Arg His Arg Phe Asn Asn Phe Met Leu Tyr Lys Glu Asp
        50                  55                  60

Arg Ile His Val Pro Ile Phe His Gly Arg Ile Phe Gln Glu Gly Phe
65                  70                  75                  80

Asn Met Ser Pro Val Thr Thr Ala His Ala Gly Asn Tyr Thr Cys Arg
            85                  90                  95

Gly Ser His Pro His Ser Pro Thr Gly Trp Ser Ala Pro Ser Asn Pro
            100                 105                 110

Met Val Ile Met Val Thr Gly Asn His Arg Lys Pro Ser Leu Leu Ala
            115                 120                 125

His Pro Gly Pro Leu Val Lys Ser Gly Glu Arg Val Ile Leu Gln Cys
        130                 135                 140

Trp Ser Asp Ile Met Phe Glu His Phe Leu His Lys Glu Trp Ile
145                 150                 155                 160

Ser Lys Asp Pro Ser Arg Leu Val Gly Gln Ile His Asp Gly Val Ser
            165                 170                 175

Lys Ala Asn Phe Ser Ile Gly Ser Met Met Arg Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Leu Tyr Glu Lys Pro
    210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
            245                 250                 255

Arg Glu Gly Gly Ala His Glu Arg Arg Leu Pro Ala Val Arg Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg His Ser Pro Tyr Glu Trp
    290                 295                 300

Ser Asp Pro Ser Asp Pro Leu Leu Val Ser Val Thr Gly Asn Pro Ser
305                 310                 315                 320
```

```
Ser Ser Trp Pro Ser Pro Thr Glu Pro Ser Ser Lys Ser Gly Asn Leu
            325                 330                 335

Arg His Leu His Ile Leu Ile Gly Thr Ser Val Val Lys Ile Pro Phe
            340                 345                 350

Thr Ile Leu Leu Phe Phe Leu Leu His Arg Trp Cys Ser Asn Lys Lys
            355                 360                 365

Asn Ala Ala Val Met Asp Gln Glu Pro Ala Gly Asn Arg Ser Glu Gln
            370                 375                 380

Arg Gly Phe
385

<210> SEQ ID NO 14
<211> LENGTH: 224
<212> TYPE: PRT
<213> ORGANISM: Homo sapiens
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid

<400> SEQUENCE: 14

His Glu Gly Val His Arg Lys Pro Ser Leu Leu Ala His Pro Gly Xaa
1               5                   10                  15

Leu Val Lys Ser Glu Glu Thr Val Ile Leu Gln Cys Trp Ser Asp Val
            20                  25                  30

Met Phe Glu His Phe Leu Leu His Arg Glu Gly Met Phe Asn Asp Thr
        35                  40                  45

Leu Arg Leu Ile Gly Glu His His Asp Gly Val Ser Lys Ala Asn Phe
    50                  55                  60

Ser Ile Ser Arg Met Thr Gln Asp Leu Ala Gly Thr Tyr Arg Cys Tyr
65                  70                  75                  80

Gly Ser Val Thr His Ser Pro Tyr Gln Val Ser Ala Pro Ser Asp Pro
                85                  90                  95

Leu Asp Ile Val Ile Ile Gly Leu Tyr Glu Lys Pro Ser Leu Ser Ala
            100                 105                 110

Gln Xaa Gly Pro Thr Val Leu Ala Gly Glu Asn Val Thr Leu Ser Cys
        115                 120                 125

Ser Ser Arg Ser Ser Tyr Asp Met Tyr His Leu Ser Arg Glu Gly Glu
    130                 135                 140

Ala His Glu Arg Arg Leu Pro Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe His Asp Ser Pro Tyr Glu Trp Ser Lys Ser Ser
            180                 185                 190

Asp Pro Leu Leu Val Ser Val Thr Gly Asn Pro Ser Asn Ser Trp Pro
        195                 200                 205

Ser Pro Thr Glu Pro Ser Ser Lys Thr Gly Asn Pro Arg His Leu His
    210                 215                 220

<210> SEQ ID NO 15
<211> LENGTH: 224
<212> TYPE: PRT
<213> ORGANISM: Homo sapiens
```

-continued

<400> SEQUENCE: 15

```
His Glu Gly Val His Arg Lys Pro Ser Leu Leu Ala His Pro Gly Arg
1               5                   10                  15

Leu Val Lys Ser Glu Glu Thr Val Ile Leu Gln Cys Trp Ser Asp Val
            20                  25                  30

Arg Phe Glu His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60

Ser Ile Gly Pro Met Met Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
                100                 105                 110

Gln Pro Gly Pro Thr Val Leu Ala Gly Glu Ser Val Thr Leu Ser Cys
            115                 120                 125

Ser Ser Arg Ser Ser Tyr Asp Met Tyr His Leu Ser Arg Glu Gly Glu
        130                 135                 140

Ala His Glu Cys Arg Phe Ser Ala Gly Pro Lys Val Asn Gly Thr Phe
145                 150                 155                 160

Gln Ala Asp Phe Pro Leu Gly Pro Ala Thr His Gly Gly Thr Tyr Arg
                165                 170                 175

Cys Phe Gly Ser Phe Arg Asp Ser Pro Tyr Glu Trp Ser Asn Ser Ser
            180                 185                 190

Asp Pro Leu Leu Val Ser Val Ile Gly Asn Pro Ser Asn Ser Trp Pro
        195                 200                 205

Ser Pro Thr Glu Pro Ser Ser Lys Thr Gly Asn Pro Arg His Leu His
    210                 215                 220
```

<210> SEQ ID NO 16
<211> LENGTH: 224
<212> TYPE: PRT
<213> ORGANISM: Homo sapiens

<400> SEQUENCE: 16

```
His Glu Gly Val His Arg Lys Pro Ser Leu Leu Ala His Pro Gly Pro
1               5                   10                  15

Leu Val Lys Ser Glu Glu Thr Val Ile Leu Gln Cys Trp Ser Asp Val
            20                  25                  30

Arg Phe Gln His Phe Leu Leu His Arg Glu Gly Lys Phe Lys Asp Thr
        35                  40                  45

Leu His Leu Ile Gly Glu His His Asp Gly Val Ser Lys Ala Asn Phe
    50                  55                  60

Ser Ile Gly Pro Met Met Gln Asp Leu Ala Gly Thr Tyr Arg Cys Tyr
65                  70                  75                  80

Gly Ser Val Thr His Ser Pro Tyr Gln Leu Ser Ala Pro Ser Asp Pro
                85                  90                  95

Leu Asp Ile Val Ile Thr Gly Leu Tyr Glu Lys Pro Ser Leu Ser Ala
                100                 105                 110

Gln Pro Gly Pro Thr Val Leu Ala Gly Glu Ser Val Thr Leu Ser Cys
            115                 120                 125

Ser Ser Arg Ser Ser Tyr Asp Met Tyr His Leu Ser Arg Glu Gly Glu
        130                 135                 140

Ala His Glu Arg Arg Phe Ser Ala Gly Pro Lys Val Asn Gly Thr Phe
```

```
                145                 150                 155                 160
Gln Ala Asp Phe Pro Leu Gly Pro Ala Thr His Gly Gly Thr Tyr Arg
                    165                 170                 175

Cys Phe Gly Ser Phe Arg Asp Ser Pro Tyr Glu Trp Ser Asn Ser Ser
                180                 185                 190

Asp Pro Leu Leu Val Ser Val Thr Gly Asn Pro Ser Asn Ser Trp Pro
            195                 200                 205

Ser Pro Thr Glu Pro Ser Ser Glu Thr Gly Asn Pro Arg His Leu His
        210                 215                 220

<210> SEQ ID NO 17
<211> LENGTH: 119
<212> TYPE: PRT
<213> ORGANISM: Mus musculus

<400> SEQUENCE: 17

Glu Val Gln Leu Gln Gln Ser Gly Pro Glu Leu Val Lys Pro Gly Ala
1               5                   10                  15

Ser Val Lys Ile Ser Cys Lys Ala Ser Asp Tyr Ser Phe Thr Gly Tyr
                20                  25                  30

Phe Met Asn Trp Val Met Gln Ser Gln Glu Lys Ser Leu Glu Trp Ile
            35                  40                  45

Gly Arg Ile Asn Pro Phe Asn Gly Asp Ala Phe Tyr Asn Gln Lys Phe
        50                  55                  60

Lys Gly Lys Ala Thr Leu Thr Val Asp Lys Ser Ser Asn Thr Ala His
65                  70                  75                  80

Met Glu Leu Arg Ser Leu Thr Ser Glu Asp Ser Ala Val Tyr Tyr Cys
                85                  90                  95

Ala Arg Leu Asp Tyr Arg Gly Tyr Phe Phe Asp Tyr Trp Gly Gln Gly
                100                 105                 110

Thr Thr Leu Thr Val Ser Ser
            115

<210> SEQ ID NO 18
<211> LENGTH: 108
<212> TYPE: PRT
<213> ORGANISM: Mus musculus

<400> SEQUENCE: 18

Asp Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Ser Ala
                20                  25                  30

Val Gly Trp Tyr Gln Gln Lys Pro Gly Gln Ser Pro Lys Leu Leu Ile
            35                  40                  45

Tyr Ser Ala Ser Thr Arg Tyr Thr Gly Val Pro Asp Arg Phe Thr Gly
        50                  55                  60

Ser Gly Ser Gly Thr Asp Phe Thr Leu Thr Ile Thr Asn Met Gln Ser
65                  70                  75                  80

Asp Asp Leu Ala Asp Tyr Phe Cys His Gln Tyr Ser Arg Tyr Pro Leu
                85                  90                  95

Ser Phe Gly Ser Gly Thr Lys Leu Glu Met Lys Arg
                100                 105

<210> SEQ ID NO 19
<211> LENGTH: 357
<212> TYPE: DNA
<213> ORGANISM: Mus musculus
```

<400> SEQUENCE: 19

```
gaggttcagc tgcagcagtc tggacctgag ctggtgaagc ctggggcttc agtgaagata      60
tcctgtaagg cttctgatta ctcatttact ggctacttta tgaactgggt gatgcagagc     120
caagaaaaga gccttgagtg gattggacgt attaatcctt caatggtga tgctttctac      180
aaccagaagt tcaagggcaa ggccacattg actgtggaca atcctctaa cacagcccac      240
atggagctcc ggagcctgac atctgaggac tctgcagtct attattgtgc aagattggat    300
taccgcggct acttctttga ctactggggc caaggcacca cgctcacagt ctcatca        357
```

<210> SEQ ID NO 20
<211> LENGTH: 324
<212> TYPE: DNA
<213> ORGANISM: Mus musculus

<400> SEQUENCE: 20

```
gacattgtga tgacccagtc tcaaaaattc atgtccacaa cagtaggaga cagggtcagc      60
atcacctgca aggccagtca gagtgtgggt agcgctgtag ctggtatca acagaaacca     120
ggacaatctc ctaaaactact gatttactca gcatccactc ggtacactgg agtccctgat    180
cgcttcacag gcagtggatc tgggacagat ttcactctca ccattaccaa tatgcagtct    240
gatgacctgg cagattattt ctgtcaccaa tatagcagat atcctctctc gttcggctcg    300
gggacaaagt tggaaatgaa acgg                                            324
```

<210> SEQ ID NO 21
<211> LENGTH: 114
<212> TYPE: PRT
<213> ORGANISM: Mus musculus

<400> SEQUENCE: 21

```
Gln Val Gln Leu Lys Glu Ser Gly Pro Gly Leu Val Ala Pro Ser Gln
  1               5                  10                  15
Ser Leu Ser Ile Thr Cys Thr Val Ser Gly Phe Ser Leu Thr Asp Tyr
             20                  25                  30
Gly Val Ser Trp Val Arg Gln Pro Pro Gly Lys Gly Leu Glu Trp Leu
         35                  40                  45
Gly Leu Ile Trp Gly Asp Gly Arg Thr Asn Tyr His Ser Ala Leu Ile
     50                  55                  60
Ser Arg Leu Ser Ile Ser Lys Asp Asn Ser Lys Ser Gln Val Phe Leu
 65                  70                  75                  80
Lys Leu Asn Ser Leu Gln Ile Asp Asp Thr Ala Thr Tyr Tyr Cys Ala
                 85                  90                  95
Arg Arg Gly Ala Met Asp Tyr Trp Gly Gln Gly Thr Ser Val Thr Val
            100                 105                 110
Ser Ser
```

<210> SEQ ID NO 22
<211> LENGTH: 342
<212> TYPE: DNA
<213> ORGANISM: Mus musculus

<400> SEQUENCE: 22

```
caggtgcagc tgaaggagtc aggacctggc ctggtggcgc cctcacagag cctgtccatc      60
acatgcactg tctcagggtt ctcactaacc gactatggtg taagctgggt tcgccagcct    120
ccaggaaagg gtctggagtg gctgggacta atatggggtg acgggcgcac aaattatcat    180
```

```
tcagctctca tatccagact gagcatcagc aaggataact ccaagagcca agttttctta    240
aaactgaaca gtctgcaaat tgatgacaca gccacatact actgtgccag aagggg tgct   300 atggactact ggggtcaagg aacctcggtc accgtctcct ca                      342
```

<210> SEQ ID NO 23
<211> LENGTH: 324
<212> TYPE: DNA
<213> ORGANISM: Mus musculus

<400> SEQUENCE: 23

```
gacattgtga tgacccagtc tcaaaaattc atgtccacaa cagtaggaga cagggtcagc     60
atcacctgca aggccagtca gagtgtgggt agcgctgtag gctggtatca acagaaacca    120
ggacaatctc ctaaaactac tgatttactca gcatccactc ggtacactgg agtccctgat   180
cgcttcacag gcagtggatc tgggacagat ttcactctca ccattaccaa tatgcagtct   240
gatgacctgg ctgattattt ctgtcaccaa tatagcagat atcctctctc gttcggctcg   300
gggacaaagt tggaaatgaa acgg                                          324
```

<210> SEQ ID NO 24
<211> LENGTH: 214
<212> TYPE: PRT
<213> ORGANISM: Homo sapiens

<400> SEQUENCE: 24

```
Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 25
<211> LENGTH: 450
<212> TYPE: PRT

<213> ORGANISM: Homo sapiens

<400> SEQUENCE: 25

```
Gln Val Gln Leu Val Gln Ser Gly Ala Glu Val Lys Pro Gly Ser
1               5                  10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
```

```
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```